US00RE51131E

(19) United States
(12) Reissued Patent
Tanner et al.

(10) Patent Number: US RE51,131 E
(45) Date of Reissued Patent: Nov. 24, 2026

(54) BARLEY WITH VERY LOW LEVELS OF HORDEINS

(71) Applicants: Commonwealth Scientific and Industrial Research Organisation, Acton (AU); Grains Research and Development Corporation, Barton (AU)

(72) Inventors: Gregory John Tanner, Elwood (AU); Crispin Alexander Howitt, Evatt (AU); Michelle Lisa Colgrave, Everton Hills (AU); Malcolm James Blundell, Gordon (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU)

(21) Appl. No.: 18/072,306

(22) Filed: Nov. 30, 2022

Related U.S. Patent Documents

Reissue of:
(64) Patent No.: 10,849,345
Issued: Dec. 1, 2020
Appl. No.: 14/897,616
PCT Filed: Jun. 13, 2014
PCT No.: PCT/AU2014/000619
§ 371 (c)(1),
(2) Date: Dec. 10, 2015
PCT Pub. No.: WO2014/197943
PCT Pub. Date: Dec. 18, 2014

(30) Foreign Application Priority Data

Jun. 13, 2013 (AU) ..... 2013902140
Jul. 11, 2013 (AU) ..... 2013902565

(51) Int. Cl.
*A23L 7/10* (2016.01)

(52) U.S. Cl.
CPC ..... *A23L 7/198* (2016.08)

(58) Field of Classification Search
CPC .. A23L 7/198; A23L 7/20; A01H 5/10; A01H 6/4624; A21D 13/02; A21D 13/047; A21D 13/066; A21D 13/04; C12Q 2600/156; C12Q 1/6895; C12C 2200/01; C12C 12/00
See application file for complete search history.

(56) References Cited

FOREIGN PATENT DOCUMENTS

WO WO-2009021285 A1 * 2/2009 ..... A01H 5/10

OTHER PUBLICATIONS

Brennan CS et al. "The Production and Characterization of Hor3 Null Lines of Barley Provides New Information on the Relationship of D Hordein to Malting Performance." J Cereal Sci 28: 291-299. (Year: 1998).*
Tanner GJ et al. "Creation of the first ultra-low gluten barley (*Hordeum vulgare* L.) for coeliac and gluten-intolerant populations." Plant Biotech. J. 14: 1139-1150. (Year: 2016).*
English translation of Jan. 18, 2021 4th Examination Report that issued in connection with corresponding Mexican Patent Application No. MX/a/2015/017009.
English translation of Mar. 31, 2021 Notice of Preliminary Rejection issued in connection with Korean Patent Application No. 10-2016-7000061.
Jun. 8, 2021 Examiner's Opinion issued in connection with Brazilian Patent Application No. BR112015031257-8 and English translation thereof.
Jun. 7, 2021 First Examination Report issued in connection with Japanese Patent Application No. 2020-047974 and English translation thereo.
Tanner et al. (2013). Measuring hordein (gluten) in beer—a comparison of Elisa and mass spectrometry. PLoS One, 8(2), e56452.
Jul. 27, 2021 Response filed to the First Examination Report in connection with the corresponding Indian Patent Application 11002/DELNP/2015.
Jul. 23, 2021 Form 3 Submission filed in connection with the corresponding Indian Patent Application 11002/DELNP/2015.
Nov. 16, 2021 Final Decision Rejection notice which issued in connection with the corresponding Chilean Patent Application 201503590 and English translation thereof.
Dec. 6, 2021 Rejection Decision issued in connection with the corresponding Brazilian Patent Application BR1120150312578 and English translation thereof.
Dec. 25, 2022 Notice of Final Rejection issued in connection with the corresponding South Korean Patent Application 10-2016-7000061 and English translation thereof.
Apr. 25, 2022 Second Office Action issued in connection with the corresponding Japanese Patent Application 2020-47974 and English translation thereof.
Jul. 31, 2023 Examination Report issued in connection with European Patent Application No. 14810699.0.
Feb. 9, 2024 Response to Jul. 31, 2023 Examination Report issued in connection with European Patent Application No. 14810699.0.
Sep. 11, 2024 Examination Report issued in connection with European Patent Application No. issued in connection with European Patent Application No. 14810699.0.

* cited by examiner

*Primary Examiner* — Lora E Barnhart Driscoll
(74) *Attorney, Agent, or Firm* — Gary J. Gershik

(57) ABSTRACT

The present invention relates to methods of producing a food or malt-based beverage suitable for consumption by a subject with Coeliac's disease. In particular, the present invention relates to methods of producing a food or malt-based beverage with very low levels of hordeins. Also provided are barley plants which produce grain that can be used in the methods of the invention.

37 Claims, 14 Drawing Sheets

Figure 1:
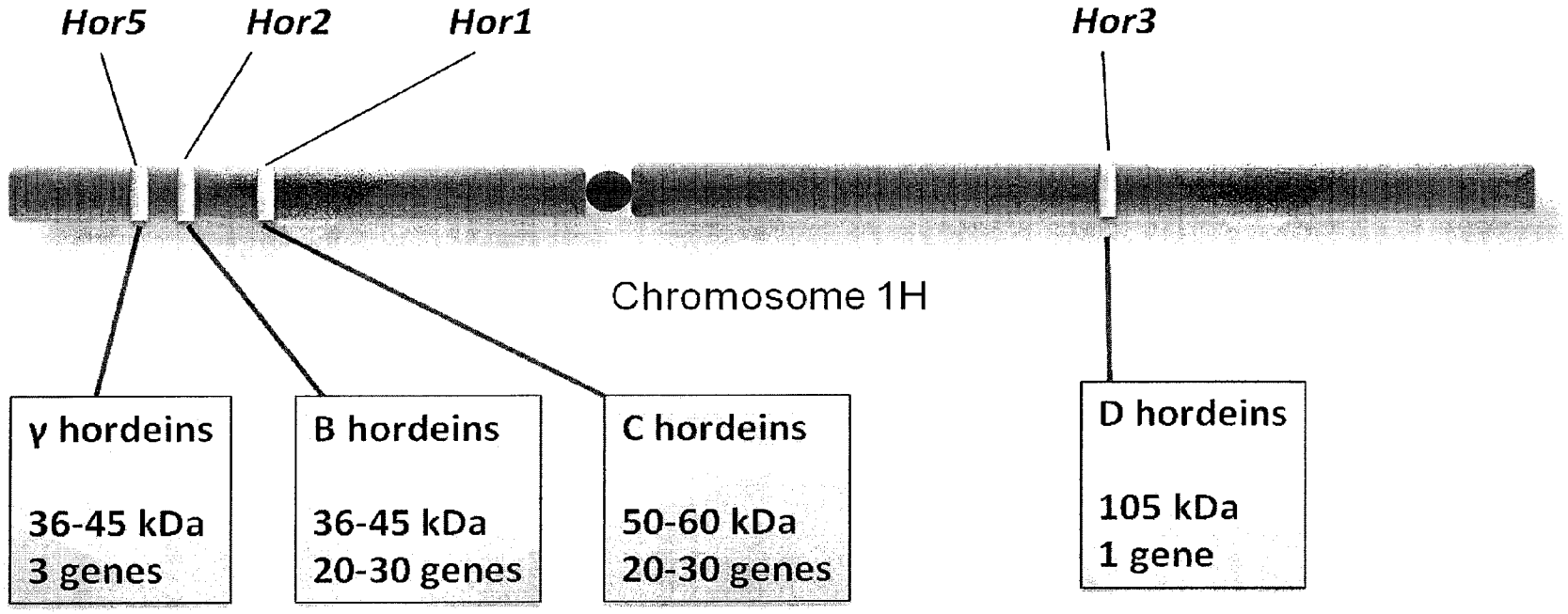

Specification includes a Sequence Listing.

Serial No. : 14/897,616
Filed : December 10, 2015
Exhibit A of Amendment in Response to July 7, 2017 Office Action and Petition for Two-Month Extension of Time

```
                    10        20        30        40        50        60        70        80
            ....|....|....|....|....|....|....|....|....|....|....|....|....|....|....|....|
Sloop con   MAKRLVLFVAVIVALVALTTAEREINGNNIFLDSRSRQLQCERELQESSLEACRRVVDQQLVGQLPWSTGLQMQCCQQLR
D-null con  MAKRLVLFVAVIVALVALTTAEPEINGNNIFLDSRSGQLQCERELQESSLEACRRVVDQQLVGQLPWSTGLQMQCCQQLR

                    90       100       110       120       130       140       150       160
            ....|....|....|....|....|....|....|....|....|....|....|....|....|....|....|....|
Sloop con   DVSPECRPVALSQVVRQYEQQTEVPSKGGSFYPGGTAPPLQQGGWWGTSVKWYYPDQTSSQQSWQGQQGYHQSVTSSQQP
D-null con  DVSPECRPVALSQVVRQYEQQTEVPSKGGSFYPGGTAPPLQQGGWWGTSVKWYYPDQTSSQQSWQGQQG*

                   170       180       190       200       210       220       230       240
            ....|....|....|....|....|....|....|....|....|....|....|....|....|....|....|....|
Sloop con   GQGQQGSYPGSTFPQQPGQGQQPGQRQPWSYPSATFPQQPGQ~~GQGQQGYYPGATSLLQPGQGQQGPYQSATSPQQPGQ

                   250       260       270       280       290       300       310       320
            ....|....|....|....|....|....|....|....|....|....|....|....|....|....|....|....|
Sloop con   GQGHQETYQFATSPHQPGQWQQPGQGQQGYYPSVTSPQQSGQGQTGYPSTTSPQQSGQGQQLGQGQQPGQGQQGYPSATF

                   330       340       350       360       370       380       390       400
            ....|....|....|....|....|....|....|....|....|....|....|....|....|....|....|....|
Sloop con   PQQPGQWQQGSYPSTTSPQQSGQGQQGYNPSGTSTQQPGQVQQLGQGQQGYYPIATSPQQPGQGQQLGQGQQPGHGQQLV

                   410       420       430       440       450       460       470       480
            ....|....|....|....|....|....|....|....|....|....|....|....|....|....|....|....|
Sloop con   QGQQQGQGQQGHYPSMTSPHQTGQGQKGYYPSAISPQQSGQGQQGYQPSGASSQGSVQGACQHSTSSPQQQAQGCQASSP

                   490       500       510       520       530       540       550       560
            ....|....|....|....|....|....|....|....|....|....|....|....|....|....|....|....|
Sloop con   KQGLGSLYYPSGAYTQQKPGQGYNPGGTSPLHQQGGGFGGGLTTEQPQGGKQPFHCQQTTVSPHQGQQTTVSPHQGQQTT

                   570       580       590       600       610       620       630       640
            ....|....|....|....|....|....|....|....|....|....|....|....|....|....|....|....|
Sloop con   VSPHQGQQTTVSPHQGQQTTVSPHQGQQTTVSPHQGQQTTVSPHPGQQTTVSPHQGQQTTVSPHPGQQTTVSPHQGQQTT

                   650       660       670       680       690       700       710       720
            ....|....|....|....|....|....|....|....|....|....|....|....|....|....|....|....|
Sloop con   VSPHQGQQTTVSPHQGQQTTVSPHQGQQTTVSPHQGQQPGEQPCGFPGQQTTVSLHHGQQSNELYYGSPYHVSVEQPSAS

                   730       740       750
            ....|....|....|....|....|....|.
Sloop con   LKVAKAQQLAAQLPAMCRLEGGGGLLASQ*
```

Figure 3

```
                  10        20        30        40        50        60        70
          ....|....|....|....|....|....|....|....|....|....|....|....|....|....|
Sloop con GACACATATTCTGCCAAAACCCCAGAACAATAATCACTTCTCGTAGATGAAGAGAACAGACCAAGATACA
D-null con ..............................................................

                  80        90       100       110       120       130       140
          ....|....|....|....|....|....|....|....|....|....|....|....|....|....|
Sloop con AACGTCCACGCTTCAGCAAACAGTACCCCAGAACTAGGATTAAGCCGATTACGCGGCTTTAGCAGACCGT
D-null con ..............................................................

                 150       160       170       180       190       200       210
          ....|....|....|....|....|....|....|....|....|....|....|....|....|....|
Sloop con CCAAAAAAACTGTTTTGCAAAGCTCCAATTCCTCCTTGCTTATCCAATTTCTTTTGTGTTGGCAAACTGC
D-null con ..............................................................

                 220       230       240       250       260       270       280
          ....|....|....|....|....|....|....|....|....|....|....|....|....|....|
Sloop con ACTTGTCCAACCGATTTTGTTCTTCCCGTGTTTCTTCTTAGGCTAACTAACACAGCCGTGCACATAGCCA
D-null con ....C.....................A.......................................

                 290       300       310       320       330       340       350
          ....|....|....|....|....|....|....|....|....|....|....|....|....|....|
Sloop con TGGTCCGGAATCTTCACCTCGTCCCTATAAAAGCCCAGCCAATCTCCACAATCTCATCATCACCGAGAAC
D-null con ..........C...................................................

                 360       370       380       390       400       410       420
          ....|....|....|....|....|....|....|....|....|....|....|....|....|....|
Sloop con ACCGAGAACCACAAAACTAGAGATCAATTCATTGACAGTCCACCGAGATGGCTAAGCGGCTGGTCCTCTT

                                                          M  A  K  R  L  V  L  F
D-null con ..........................................................
                                                          M  A  K  R  L  V  L  F

                 430       440       450       460       470       480       490
          ....|....|....|....|....|....|....|....|....|....|....|....|....|....|
Sloop con TGTGGCGGTAATCGTCGCCCTCGTGGCTCTCACCACCGCTGAACGTGAGATCAATGGGAACAACATTTTC

           V  A  V  I  V  A  L  V  A  L  T  T  A  E  R  E  I  N  G  N  N  I  F
D-null con ..........................................C.......................
           V  A  V  I  V  A  L  V  A  L  T  T  A  E  P  E  I  N  G  N  N  I  F

                 500       510       520       530       540       550       560
          ....|....|....|....|....|....|....|....|....|....|....|....|....|....|
Sloop con CTTGATAGCCGCTCTAGGCAGCTACAGTGTGAGCGCGAGCTCCAGGAGAGCTCGCTCGAGGCGTGCCGGC
          L  D  S  R  S  R  Q  L  Q  C  E  R  E  L  Q  E  S  S  L  E  A  C  R  R
D-null con ...............G..............................................
          L  D  S  R  S  G  Q  L  Q  C  E  R  E  L  Q  E  S  S  L  E  A  C  R  R

                 570       580       590       600       610       620       630
          ....|....|....|....|....|....|....|....|....|....|....|....|....|....|
Sloop con GGGTCGTGGACCAACAGCTGGTTGGCCAGCTGCCATGGAGCACGGGGCTCCAGATGCAGTGCTGCCAGCA
           V  V  D  Q  Q  L  V  G  Q  L  P  W  S  T  G  L  Q  M  Q  C  C  Q  Q
D-null con ..........................................................
           V  V  D  Q  Q  L  V  G  Q  L  P  W  S  T  G  L  Q  M  Q  C  C  Q  Q

                 640       650       660       670       680       690       700
          ....|....|....|....|....|....|....|....|....|....|....|....|....|....|
Sloop con GCTTCGGGACGTCAGCCCCGAGTGCCGCCCCGTCGCCCTCAGCCAGGTCGTGAGGCAATACGAGCAGCAA
                                                                 5' D null marker
           L  R  D  V  S  P  E  C  R  P  V  A  L  S  Q  V  V  R  Q  Y  E  Q  Q
D-null con ..........................................................
           L  R  D  V  S  P  E  C  R  P  V  A  L  S  Q  V  V  R  Q  Y  E  Q  Q
```

Figure 4

```
                710       720       730       740       750       760       770
            ....|....|....|....|....|....|....|....|....|....|....|....|....|
Sloop con   ACCGAGGTGCCATCCAAGGGAGGATCCTTCTACCCGGGCGGGACCGCACCGCCGCTGCAGCAAGGAGGAT
            T  E  V  P  S  K  G  G  S  F  Y  P  G  G  T  A  P  P  L  Q  Q  G  G  W
D-null con  ....................................................................
            T  E  V  P  S  K  G  G  S  F  Y  P  G  G  T  A  P  P  L  Q  Q  G  G  W

                780       790       800       810       820       830       840
            ....|....|....|....|....|....|....|....|....|....|....|....|....|
Sloop con   GGTGGGGAACCTCTGTAAAATGGTACTACCCAGACCAAACTTCTTCGCAACAGTCATGGCAAGGGCAACA
             W  G  T  S  V  K  W  Y  Y  P  D  Q  T  S  S  Q  Q  S  W  Q  G  Q  Q
D-null con  ....................................................................
             W  G  T  S  V  K  W  Y  Y  P  D  Q  T  S  S  Q  Q  S  W  Q  G  Q  Q

                850       860       870       880       890       900       910
            ....|....|....|....|....|....|....|....|....|....|....|....|....|
Sloop con   AGGGTACCACCAAAGCGTAACTTCTTCCCAGCAGCCAGGACAAGGGCAGCAAGGGTCCTACCCAGGTTCA
              KpnI
             G  Y  H  Q  S  V  T  S  S  Q  Q  P  G  Q  G  Q  Q  G  S  Y  P  G  S
D-null con  ......G.............................................................
             G  *

                920       930       940       950       960       970       980
            ....|....|....|....|....|....|....|....|....|....|....|....|....|
Sloop con   ACTTTCCCGCAGCAGCCAGGACAAGGACAACAACCAGGACAGAGGCAGCCATGGTCCTATCCAAGTGCAA
                                      3' D null marker
            T  F  P  Q  Q  P  G  Q  G  Q  Q  P  G  Q  R  Q  P  W  S  Y  P  S  A  T
D-null con  ....................................................................

                990       1000      1010      1020      1030      1040      1050
            ....|....|....|....|....|....|....|....|....|....|....|....|....|
Sloop con   CTTTCCCACAACAGCCAGGGC------AAGGGCAAGGGCAACAAGGGTACTACCCAGGCGCAACTTCCCT
             F  P  Q  Q  P  G  Q        G  Q  G  Q  Q  G  Y  Y  P  G  A  T  S  L
D-null con  ....................AAGGGC......................................

                1060      1070      1080      1090      1100      1110      1120
            ....|....|....|....|....|....|....|....|....|....|....|....|....|
Sloop con   GCTGCAGCCAGGACAAGGGCAACAAGGGCCCTACCAGAGTGCAACTTCTCCACAGCAGCCAGGACAAGGA
             L  Q  P  G  Q  G  Q  Q  G  P  Y  Q  S  A  T  S  P  Q  Q  P  G  Q  G
D-null con  ...................................A...............................

                1130      1140      1150      1160      1170      1180      1190
            ....|....|....|....|....|....|....|....|....|....|....|....|....|
Sloop con   CAGGGACACCAAGAGACCTATCAATTTGCAACTTCCCCGCATCAGCCAGGACAATGGCAACAACCAGGAC
            Q  G  H  Q  E  T  Y  Q  F  A  T  S  P  H  Q  P  G  Q  W  Q  Q  P  G  Q
D-null con  ........A......C......C.A...........................................

                1200      1210      1220      1230      1240      1250      1260
            ....|....|....|....|....|....|....|....|....|....|....|....|....|
Sloop con   AAGGGCAACAAGGGTACTACCCAAGTGTAACTTCTCCACAACAGTCGGGACAAGGGCAAACAGGGTACCC
             G  Q  Q  G  Y  Y  P  S  V  T  S  P  Q  Q  S  G  Q  G  Q  T  G  Y  P
D-null con  ...........................................................CA.......

                1270      1280      1290      1300      1310      1320      1330
            ....|....|....|....|....|....|....|....|....|....|....|....|....|
Sloop con   AAGTACAACTTCTCCACAACAATCGGGGCAAGGGCAACAGCTGGGACAAGGGCAACAACCAGGACAAGGG
             S  T  T  S  P  Q  Q  S  G  Q  G  Q  Q  L  G  Q  G  Q  Q  P  G  Q  G
D-null con  ....................................................................

                1340      1350      1360      1370      1380      1390      1400
            ....|....|....|....|....|....|....|....|....|....|....|....|....|
Sloop con   CAACAAGGGTACCCAAGTGCAACTTTTCCACAACAGCCAGGACAATGGCAACAAGGGTCCTACCCAAGTA
            Q  Q  G  Y  P  S  A  T  F  P  Q  Q  P  G  Q  W  Q  Q  G  S  Y  P  S  T
D-null con  ....................................................................
```

Figure 4 (continued)

```
                1410      1420      1430      1440      1450      1460      1470
          ....|....|....|....|....|....|....|....|....|....|....|....|....|....|
Sloop con CAACTTCTCCGCAGCAGTCAGGACAAGGGCAACAAGGGTACAACCCAAGTGGAACTTCTACGCAGCAGCC
           T  S  P  Q  Q  S  G  Q  G  Q  Q  G  Y  N  P  S  G  T  S  T  Q  Q  P
D-null con ....................................................................

                1480      1490      1500      1510      1520      1530      1540
          ....|....|....|....|....|....|....|....|....|....|....|....|....|....|
Sloop con GGGACAAGTGCAACAGTTGGGACAAGGGCAACAAGGGTACTACCCAATTGCAACTTCTCCGCAGCAGCCA
           G  Q  V  Q  Q  L  G  Q  G  Q  Q  G  Y  Y  P  I  A  T  S  P  Q  Q  P
D-null con ....................................................................

                1550      1560      1570      1580      1590      1600      1610
          ....|....|....|....|....|....|....|....|....|....|....|....|....|....|
Sloop con GGACAAGGGCAACAGCTAGGACAAGGGCAACAACCAGGACATGGGCAACAGCTAGTGCAAGGGCAACAAC
          G  Q  G  Q  Q  L  G  Q  G  Q  Q  P  G  H  G  Q  Q  L  V  Q  G  Q  Q  Q
D-null con ....................................................................

                1620      1630      1640      1650      1660      1670      1680
          ....|....|....|....|....|....|....|....|....|....|....|....|....|....|
Sloop con AAGGACAAGGGCAACAAGGACACTACCCAAGTATGACTTCTCCGCACCAAACAGGACAAGGGCAAAAAGG
           G  Q  G  Q  Q  G  H  Y  P  S  M  T  S  P  H  Q  T  G  Q  G  Q  K  G
D-null con ....................................................................

                1690      1700      1710      1720      1730      1740      1750
          ....|....|....|....|....|....|....|....|....|....|....|....|....|....|
Sloop con ATACTACCCAAGTGCAATTTCTCCGCAGCAGTCAGGACAAGGACAACAAGGATACCAGCCTAGTGGAGCT
           Y  Y  P  S  A  I  S  P  Q  Q  S  G  Q  G  Q  Q  G  Y  Q  P  S  G  A
D-null con ....................................................................

                1760      1770      1780      1790      1800      1810      1820
          ....|....|....|....|....|....|....|....|....|....|....|....|....|....|
Sloop con TCTTCACAGGGGTCGGTGCAAGGGGCGTGCCAGCACAGCACATCTTCTCCGCAGCAGCAAGCACAAGGGT
          S  S  Q  G  S  V  Q  G  A  C  Q  H  S  T  S  S  P  Q  Q  Q  A  Q  G  C
D-null con ............................A...........................................

                1830      1840      1850      1860      1870      1880      1890
....|....|....|....|....|....|....|....|....|....|....|....|....|....|
Sloop con GCCAAGCTTCTTCACCAAAGCAAGGGCTAGGGTCGTTGTACTACCCGAGTGGAGCTTATACACAACAGAA
           Q  A  S  S  P  K  Q  G  L  G  S  L  Y  Y  P  S  G  A  Y  T  Q  Q  K
D-null con ....................................................................

                1900      1910      1920      1930      1940      1950      1960
          ....|....|....|....|....|....|....|....|....|....|....|....|....|....|
Sloop con ACCAGGGCAAGGGTACAACCCAGGTGGAACTTCTCCGCTGCACCAGCAAGGGGGAGGGTTCGGCGGCGGG
           P  G  Q  G  Y  N  P  G  G  T  S  P  L  H  Q  Q  G  G  G  F  G  G  G
D-null con ....................................................................

                1970      1980      1990      2000      2010      2020      2030
          ....|....|....|....|....|....|....|....|....|....|....|....|....|....|
Sloop con TTAACGACGGAGCAACCGCAGGGAGGAAAGCAGCCATTCCATTGCCAGCAAACCACTGTCTCCCCTCACC
          L  T  T  E  Q  P  Q  G  G  K  Q  P  F  H  C  Q  Q  T  T  V  S  P  H  Q
D-null con ....................................................................

                2040      2050      2060      2070      2080      2090      2100
          ....|....|....|....|....|....|....|....|....|....|....|....|....|....|
Sloop con AGGGTCAGCAAACCACTGTTTCCCCTCATCAGGGTCAGCAAACCACTGTCTCCCCTCATCAGGGTCAGCA
           G  Q  Q  T  T  V  S  P  H  Q  G  Q  Q  T  T  V  S  P  H  Q  G  Q  Q
D-null con ...................C............................................
```

Figure 4 (continued)

```
                2110      2120      2130      2140      2150      2160      2170
          ....|....|....|....|....|....|....|....|....|....|....|....|....|....|
Sloop con AACCACTGTCTCCCCTCACCAGGGTCAGCAAACCACCGTCTCCCCTCACCAGGGTCAGCAAACCACCGTC
           T  T  V  S  P  H  Q  G  Q  Q  T  T  V  S  P  H  Q  G  Q  Q  T  T  V
D-null con ..........................----------------------------------------

                2180      2190      2200      2210      2220      2230      2240
          ....|....|....|....|....|....|....|....|....|....|....|....|....|....|
Sloop con TCCCCTCATCAGGGTCAGCAAACCACTGTCTCCCCTCATCCGGGTCAGCAAACCACTGTCTCCCCTCATC
          S  P  H  Q  G  Q  Q  T  T  V  S  P  H  P  G  Q  Q  T  T  V  S  P  H  Q
D-null con ----------------------------------------------------------------------

                2250      2260      2270      2280      2290      2300      2310
          ....|....|....|....|....|....|....|....|....|....|....|....|....|....|
Sloop con AGGGTCAGCAAACCACTGTCTCCCCTCATCCGGGTCAGCAAACCACTGTCTCCCCTCATCAGGGTCAGCA
            G  Q  Q  T  T  V  S  P  H  P  G  Q  Q  T  T  V  S  P  H  Q  G  Q  Q
D-null con ---------.........................................................

                2320      2330      2340      2350      2360      2370      2380
          ....|....|....|....|....|....|....|....|....|....|....|....|....|....|
Sloop con AACCACTGTCTCCCCTCATCAGGGTCAGCAAACCACCGTCTCCCCTCATCAGGGTCAGCAAACCACCGTC
           T  T  V  S  P  H  Q  G  Q  Q  T  T  V  S  P  H  Q  G  Q  Q  T  T  V
D-null con ....................C............................................

                2390      2400      2410      2420      2430      2440      2450
          ....|....|....|....|....|....|....|....|....|....|....|....|....|....|
Sloop con TCCCCTCATCAGGGTCAGCAAACCACCGTCTCCCCTCATCAGGGTCAGCAGCCCGGCGAGCAGCCTTGCG
          S  P  H  Q  G  Q  Q  T  T  V  S  P  H  Q  G  Q  Q  P  G  E  Q  P  C  G
D-null con ....................................C.............................

                2460      2470      2480      2490      2500      2510      2520
          ....|....|....|....|....|....|....|....|....|....|....|....|....|....|
Sloop con GTTTCCCTGGCCAGCAAACCACCGTGTCTCTGCACCATGGTCAGCAGTCCAACGAGTTGTACTACGGCAG
            F  P  G  Q  Q  T  T  V  S  L  H  H  G  Q  Q  S  N  E  L  Y  Y  G  S
D-null con ....................................................................

                2530      2540      2550      2560      2570      2580      2590
          ....|....|....|....|....|....|....|....|....|....|....|....|....|....|
Sloop con CCCATACCATGTTAGCGTGGAGCAGCCGTCGGCCAGCCTAAAGGTAGCAAAGGCGCAGCAGCTCGCGGCG
           P  Y  H  V  S  V  E  Q  P  S  A  S  L  K  V  A  K  A  Q  Q  L  A  A
D-null con ...............................................................A

                2600      2610      2620      2630      2640      2650      2660
          ....|....|....|....|....|....|....|....|....|....|....|....|....|....|
Sloop con CAGCTGCCGGCAATGTGTCGGCTGGAGGGCGGCGGCGGCCTGTTGGCCAGCCAGTAGTAGAACTCTGGCA
          Q  L  P  A  M  C  R  L  E  G  G  G  G  L  L  A  S  Q  *
D-null con ....................................................................

                2670      2680      2690      2700      2710      2720      2730
          ....|....|....|....|....|....|....|....|....|....|....|....|....|....|
Sloop con GCTCGCATGGTGCTTGGGCATGCATGCATCTTAGCTATACAATAAACGTGACGTGTGCTTGCAGTTTTTC
D-null con ............................C...........................................

                2740      2750      2760      2770      2780      2790      2800
          ....|....|....|....|....|....|....|....|....|....|....|....|....|....|
Sloop con ATGTAACTAGGGTAAAACCCAACAATAATGCAAAACGGAAAGCTTCTCCATCCAAAAAAAGAACAAAACT
D-null con ....................................................................

                2810      2820      2830      2840
          ....|....|....|....|....|....|....|....|....
Sloop con GGTGCTATATATAGTATGCGCTACATGTCTCAGCTCATTGTCAG
D-null con ..........................................
```

Figure 4 (continued)

Figure 8:
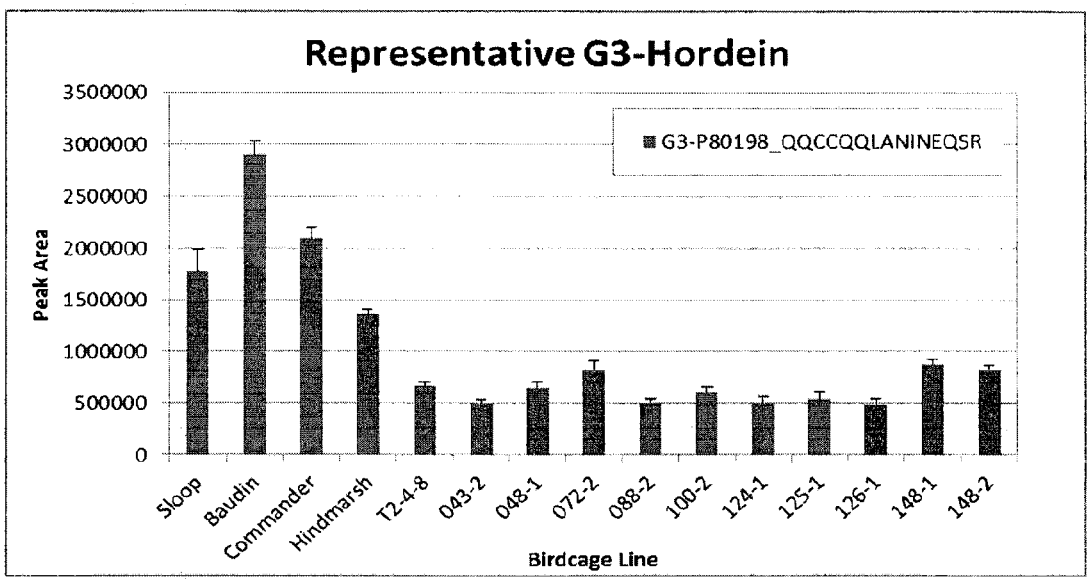

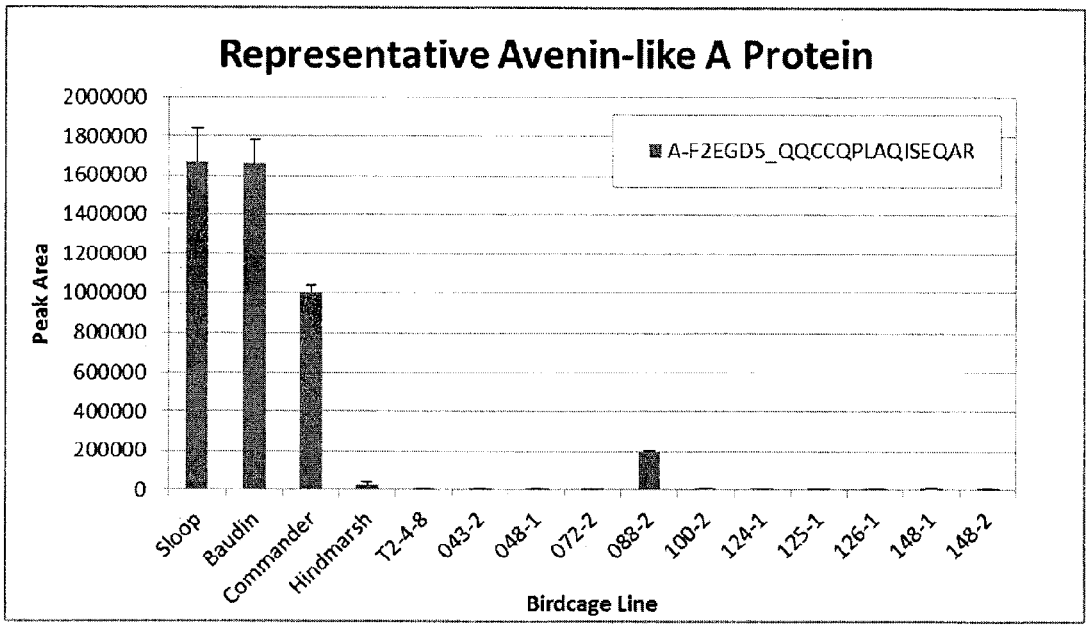
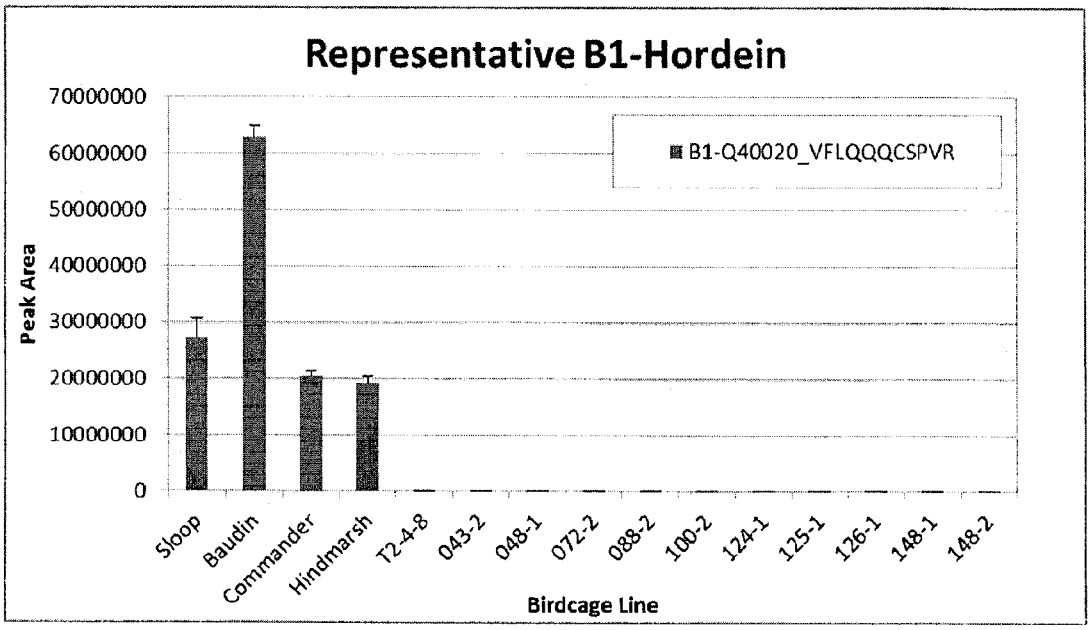
Figure 8

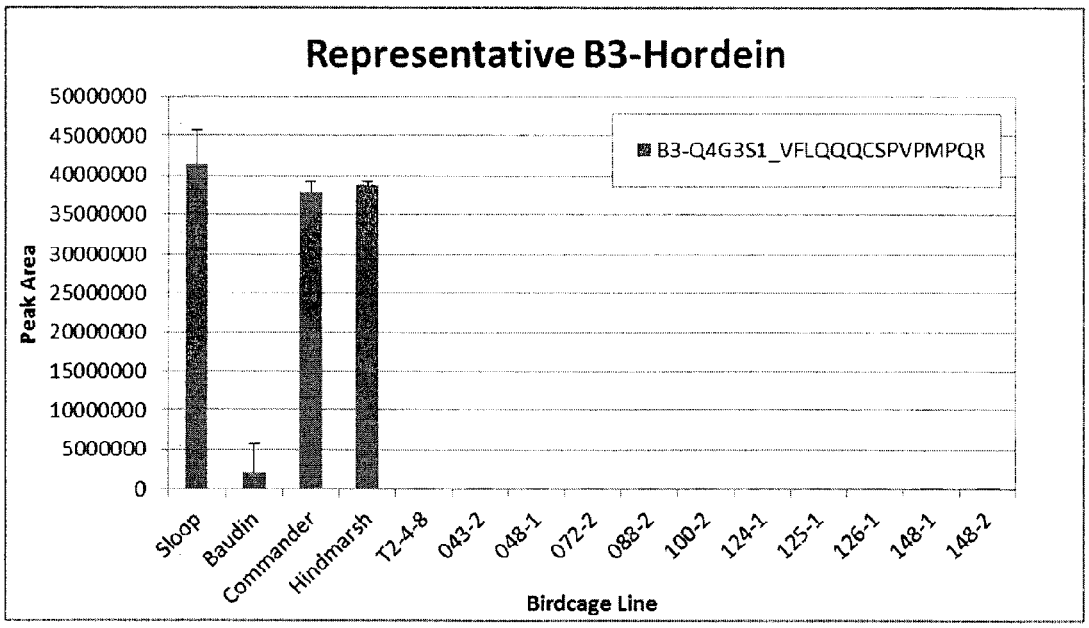
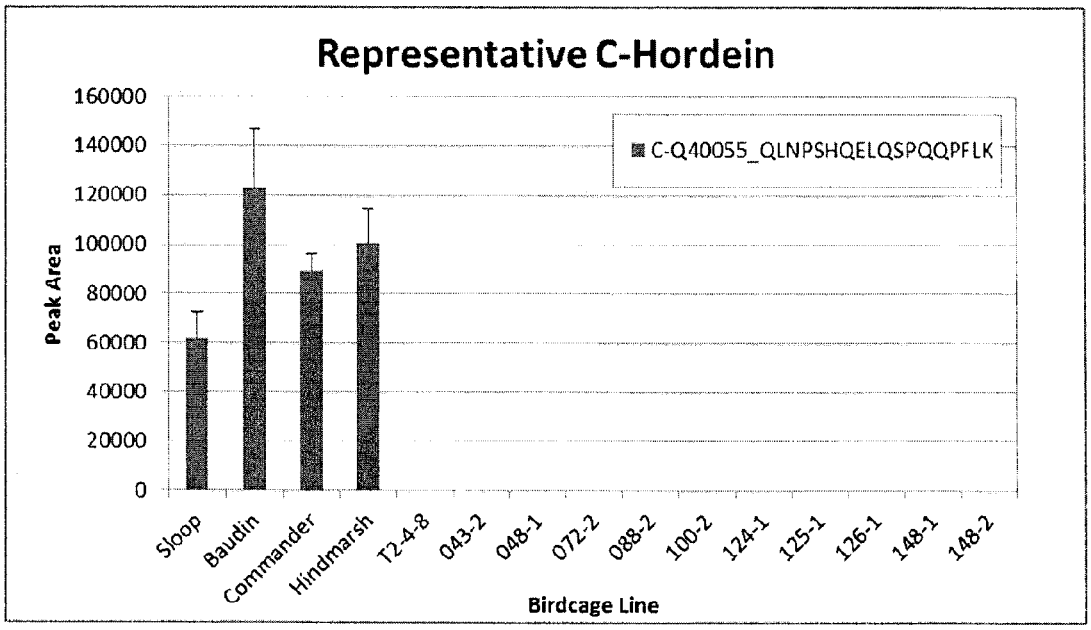
Figure 8 (continued)

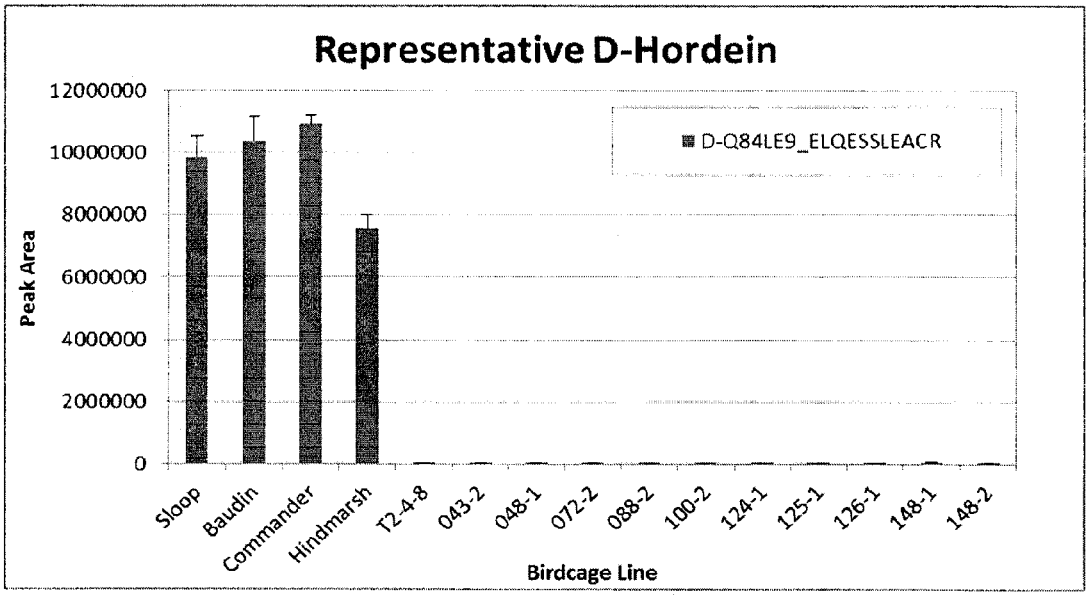
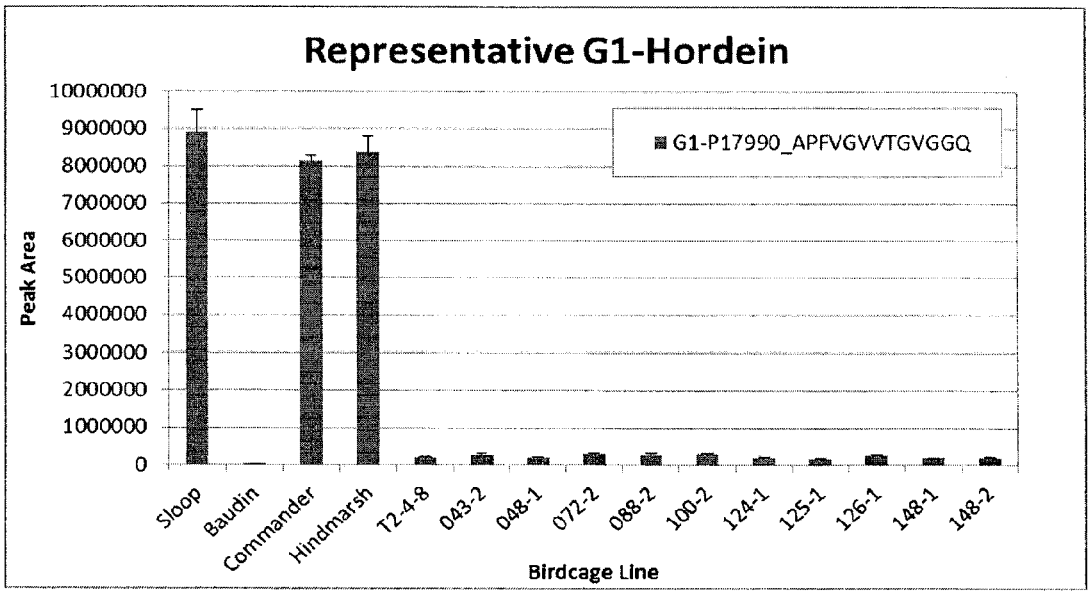
Figure 8 (continued)

BARLEY WITH VERY LOW LEVELS OF HORDEINS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application is a § 371 national stage of PCT International Application No. PCT/AU2014/000619, filed Jun. 13, 2014, claiming priority of Australian Patent Application No. 2013902565, filed Jul. 11, 2013 and Australian Patent Application No. 2013902140, filed Jun. 13, 2013, the contents of each of which are hereby incorporated by reference in their entirety.

REFERENCE TO A SEQUENCE LISTING

This application incorporates-by-reference nucleotide and/or amino acid sequences which are present in the file named "[151210_88101_Sequence_Listing_JAM.txt] *221220_88101-Reissue_SequenceListing_DH.xml*," which is [48.6] *88* kilobytes in size, and which was created [Dec. 4, 2015] *Dec. 19, 2022* in the IBM-PC machine format, having an operating system compatibility with MS-Windows, which is contained in the [text] *xml* file filed [Dec. 10, 2015] *Dec. 20, 2022* as part of this application.

FIELD OF THE INVENTION

The present invention relates to methods of producing a food or malt-based beverage suitable for consumption by a subject with Coeliac's disease. In particular, the present invention relates to methods of producing a food or malt-based beverage with very low levels of hordeins. Also provided are barley plants which produce grain that can be used in the methods of the invention.

BACKGROUND OF THE INVENTION

Coeliac disease (CD) is a T-cell mediated enteropathy triggered by the consumption of prolamins from grains such as wheat, barley and rye. Clinical symptoms of CD include fatigue, diarrhoea, abdominal distension, weight loss, anemia and neurological disorders (Green et al., 2006). CD has been associated with increased rates of intestinal malignancy, such as 10-fold increased risk of intestinal cancer, a 3- to 6-fold increase in the risk of non-Hodgkin lymphoma and a 28-fold increased risk of intestinal T-cell lymphoma (Green et al., 2009) as well as increased rates of anemia, osteoporosis, neurologic deficits, and additional autoimmune disorders such as diabetes (Skovbjerg et al., 2005). In the case of the most studied prolamin, α-gliadin, toxicity is largely mediated by a single glutamine in a single peptide (Anderson et al., 2000; Shan et al., 2002) that produces a destructive cascade of reactions that eventually damage the small intestinal villi, reducing nutrient absorption and impacting on health. Coeliac toxic epitopes for all known prolamin proteins from wheat, barley and rye have now been extensively mapped using unbiased T-cell populations isolated from the peripheral blood of HLA-DQ2$^{+}$ coeliacs following short-term dietary challenge with wheat, barley and rye (Tye-Din et al., 2010). Surprisingly, only three highly immunogenic peptides, derived from α-gliadin (ELQPFPQPELPYPQPQ, SEQ ID NO: 1), ω-gliadin/C-hordein (EQPFPQPEQPFPWQP, SEQ ID NO: 2), and B-hordein (EPEQPIPEQPQPYPQQ, SEQ ID NO: 3), could account for 90% of the coeliac-specific response, elicited by the full complement of wheat, barley and rye proteins.

The only current treatment for CD is lifelong avoidance of dietary gluten, which consists of a family of similar proteins found in wheat (gliadins, glutenins), rye (secalins), barley (hordeins), and oats (avenins). However, such diets are costly (Lee et al., 2007) and associated with low fibre and high sugar intakes (Kupper et al., 2005; Wild et al., 2010; Ohlund et al., 2010), which in themselves are health risks. Avoidance of dietary gluten leads to a normalization of health statistics in most, but not all coeliacs (Lanzini et al., 2009; Rubio-Tapia et al., 2010). Approximately 1% of most populations world-wide suffer from coeliac disease, however, up to 50% of adults remain undiagnosed or do not display overt symptoms (Catassi et al., 1994; Fowell et al., 2006).

The major families of seed proteins in the cereals of the Triciceae are the albumins, globulins and the gluten-like proteins, collectively called prolamins (Shewry and Tatham, 1990). The albumins and globulins are widely distributed amongst flowering plants, but the prolamins are restricted to the grasses, particularly the sub-family Pooideae (Hausch et al., 2002). Prolamins, so named because they contain a high proportion of the amino acids proline and glutamine, resist proteolysis during digestion (Hausch et al., 2002). The α-gliadin gene was the first prolamin gene to be cloned and much is now known about the role of this protein in coeliac disease (Kasarda et al., 1984). The toxicity of this prolamin is focused on a single peptide 57-QLQPFPQPQLPYPQPQS-73 (SEQ ID NO: 4) with the glutamine residue Q65 being the key amino acid. Mutation of this single glutamine to, for example, a lysine, abolishes the coeliac toxicity of this prolamin (Anderson et al., 2000). Partially hydrolyzed peptides cross the epithelium and access the lamina propria by an unknown mechanism; here Q65 is de-amidated by tissue transglutaminase (tTG) to E65 (glutamate), increasing the immuno-stimulatory potential of the peptide (Skovbjerg et al., 2004). The negative charge facilitates binding of the peptide to DQ2 (or less commonly DQ8) receptors on the surface of Antigen Presenting Cells, allowing presentation of the peptides to particular gluten-specific, DQ2-restricted, CD4+ T-cells, which are targeted to the intestine. Thus activated, the CD4-T cells undergo clonal expansion and in turn assist the expansion of gluten-specific- and TG2-specific-B-cells with the resultant production of anti-TG2 and anti-gluten antibodies characteristic of coeliac disease. A cell-mediated Th1 response also occurs, through the secretion of inflammatory cytokines (Tjon et al., 2010). Thus, a simple protein interaction, facilitated by the introduction of a single negatively charged residue, initiates a series of specific and targeted cascades, ultimately leading to destruction of the intestinal villi.

Barley (Hordeum vulgare L.) is a widely grown cereal used to produce malt for the brewing and food industry. Malted barley is the main ingredient in beer, supplying the carbohydrate source for fermentation. Unfortunately for coeliacs, barley beer also contains a low, but coeliac-toxic level of hordein (gluten) (Dostalek et al., 2006). The hordeins account for half of the barley grain protein (Moravcova et al., 2009), and are composed of four multi-gene families: the B-hordeins (30-45 kDa; 70% of hordein content) and the C-hordeins (45-75 kDa; 20% of hordein content) dominate the grain hordein, while the D- (105 kDa) and γ-hordeins (35-40 kDa) are minor components (Shewry et al., 1999). Malted sorghum, millet, and buckwheat are used as gluten-free alternatives for beer production (Wijngaard et al., 2007), however, it is difficult to reproduce the quality and the low cost production of barley beer with these grains.

The WHO standard definition for gluten-free foods adopted by the Codex Alimentarius in 2008 requires that food prepared from cereals such as wheat and barley must contain less than 20 mg/kg (20 ppm) gluten to be labeled "gluten-free". An accurate quantitative method to assess the gluten content of food and beverages using mass spectrometry was reported by Colgrave et al. (2012).

WO2009/021285 described the production of barley grain which was reduced in hordein content to less than 10% of the wild-type level, particularly in the hordeins B and C. However, there remains a need for grains with much lower levels of hordeins for the production of food and beverages that can be consumed by people with CD.

There is therefore a need for barley with substantially lower levels of CD-inducing hordeins which could be used in food and drink products for CD-susceptible subjects.

SUMMARY OF THE INVENTION

The present inventors have produced barley grain with very low levels of hordeins. This grain can be used for the production of a wide variety of foods and malt based beverages which can be consumed by subjects who suffer from coeliac disease.

In a first aspect, the present invention provides a method of producing a food or malt-based beverage ingredient, or a food or a malt-based beverage, the method comprising (i) processing barley grain to produce malt, wort, flour or wholemeal, and/or (ii) mixing barley grain, or malt, wort, flour or wholemeal produced from said grain, with at least one other food or beverage ingredient, wherein the barley grain, malt, wort, flour or wholemeal comprises about 50 ppm or less hordeins, thereby producing the food or malt-based beverage ingredient, food or malt-based beverage.

In an embodiment, the grain, malt, wort, flour or wholemeal comprises about 20 ppm or less, about 10 ppm or less, about 5 ppm or less, about 0.05 ppm to about 50 ppm, or about 0.05 ppm to about 20 ppm, about 0.05 ppm to about 10 ppm, about 0.05 ppm to about 5 ppm, about 0.1 ppm to about 5 ppm, about 3.9 ppm, or about 1.5 ppm, hordeins.

In another embodiment, the average weight of the grain is at least about 35 mg, at least about 39 mg, at least about 41 mg, at least about 47 mg, about 35 mg to about 60 mg, about 40 mg to about 60 mg, about 45 mg to about 60 mg, about 39.1 mg, about 41.8 mg or about 47.2 mg.

In a further embodiment, the grain, malt, wort, flour or wholemeal comprises 20 ppm or less hordeins, and the average weight of the grain is about 40 mg to about 60 mg. In another embodiment, the grain, malt, wort, flour or wholemeal comprises 20 ppm or less hordeins, and the average weight of the grain is about 45 mg to about 60 mg. The specific mention of these combinations does not exclude other combinations of these features.

In a further embodiment, at least about 80%, at least about 90%, at least about 95%, about 80% to about 98%, or about 80% to about 93%, of the grain do not pass through a 2.8 mm sieve.

In a further embodiment, the grain, malt, wort, flour or wholemeal comprises 20 ppm or less hordeins, the average weight of the grain is about 40 mg to about 60 mg, and at least about 80% of the grain do not pass through a 2.8 mm sieve. In another embodiment, the grain, malt, wort, flour or wholemeal comprises 20 ppm or less hordeins, the average weight of the grain is about 45 mg to about 60 mg, and at least about 80% of the grain do not pass through a 2.8 mm sieve. The specific mention of these combinations does not exclude other combinations of these features.

In yet a further embodiment, the grain is from a plant which has a harvest index of at least 40%, about 40% to about 60%, about 40% to about 55%, or about 40% to about 50%. In a preferred embodiment, the grain is from a plant which has a harvest index of about 40% to about 50%

In another embodiment, the grain has a length to thickness ratio of less than about 5, less than about 4, less than about 3.8, about 2 to about 5, or about 2.5 to about 3.8.

In a further embodiment, the flour or wholemeal produced from the grain comprises about 10 ppm or less, about 5 ppm or less, about 0.05 ppm to about 10 ppm, or about 0.05 ppm to about 5 ppm, about 3.9 ppm, or about 1.5 ppm, hordeins.

In an embodiment, the malt or wort produced from the grain comprises less than about 50 ppm, or less than about 20 ppm, hordeins.

In a further embodiment, the grain, or malt, wort, flour or wholemeal produced from said grain, has a level of less than 10%, less than 5% or less than 2% of a wild-type level, or is lacking, one or more than one or all of:

i) B-hordeins comprising a sequence of amino acids provided as SEQ ID NO:53, ii) B-hordeins comprising a sequence of amino acids provided as SEQ ID NO:54, iii) C-hordeins comprising a sequence of amino acids provided as SEQ ID NO:55, and iv) D-hordeins comprising a sequence of amino acids provided as SEQ ID NO:56, wherein each of the levels of less than 10%, less than 5% or less than 2% is relative to a wild-type barley grain, or malt, wort, flour or wholemeal produced from said grain, of the barley variety Bomi, Sloop, Baudin, Yagan, Hindmarsh, or Commander.

In an embodiment, the B-hordeins are at least B1-hordein (for example comprising an amino acid sequence provided as SEQ ID NO: 78) and B3-hordein (for example comprising an amino acid sequence provided as SEQ ID NO: 79). In a further example, the C-hordeins comprise an amino acid sequence provided as SEQ ID NO: 80. In yet another example, the D-hordeins comprise an amino acid sequence provided as SEQ ID NO: 76.

In an embodiment, the grain, or malt, wort, flour or wholemeal produced from said grain, further has a level of less than 10%, less than 5% or less than 2% of a wild-type level, or is further lacking;

i) γ-hordeins comprising a sequence of amino acids provided as SEQ ID NO: 57, and/or ii) avenin-like A proteins comprising a sequence of amino acids provided as SEQ ID NO: 52, wherein each of the levels of less than 10%, less than 5% or less than 2% is relative to a wild-type barley grain, or malt, wort, flour or wholemeal produced from said grain, of the barley variety Bomi, Sloop, Baudin, Yagan, Hindmarsh, or Commander. In an example, the γ-hordeins comprise an amino acid sequence provided as SEQ ID NO: 81. In yet another example, the avenin-like A proteins comprise an amino acid sequence provided as SEQ ID NO: 84.

Preferably in the above embodiment the γ-hordeins are γ1-hordeins and γ2-hordeins.

In an embodiment, the grain is homozygous for an allele of the Hor2 locus where most or all of the B-hordein encoding genes have been deleted, or wherein the malt, wort, flour or wholemeal produced from said grain comprises DNA which comprises the allele of the Hor2 locus where most or all of the B-hordein encoding genes have been deleted.

In another embodiment, the grain is homozygous for a null allele of the gene encoding D-hordein at the Hor3 locus, or wherein the malt, wort, flour or wholemeal produced from said grain comprises DNA which comprises the null allele of the gene encoding D-hordein, the null allele preferably comprising a stop codon, splice site mutation, frame-shift mutation, insertion, deletion or encoding a truncated D-hordein, or where most or all of the D-hordein encoding gene has been deleted.

In a further embodiment, the truncated D-hordein has a stop codon at the triplet encoding amino acid number 150.

In another embodiment, the grain is homozygous for an allele at the Lys3 locus of barley which results in the grain lacking C-hordeins, or wherein the malt, wort, flour or wholemeal produced from said grain comprises DNA which comprises the allele at the Lys3 locus.

In a further embodiment, the grain, malt, wort, flour or wholemeal comprises about 1% or less, about 0.01% or less, about 0.007% or less, about 0.0027% or less, about 0.001% to about 1%, about 0.001% to about 0.01%, about 0.007%, or about 0.0027%, of the level of hordeins when compared to grain from a corresponding wild-type barley plant or malt, wort, flour or wholemeal produced in the same manner from grain from a corresponding wild-type barley plant.

In yet another embodiment, the grain is from a plant which has at least 60%, at least 80%, at least 90%, about 60% to 100%, about 70% to 100%, about 80% to 100%, about 60%, about 70%, about 80%, or about 90% of the grain yield of the wild-type barley plant.

In another embodiment, the average weight of the grain is at least about 70%, at least about 80%, at least about 90%, at least about 95%, or about 100%, of grain of the wild-type barley plant.

In yet a further embodiment, the grain, or malt, wort, flour or wholemeal produced from said grain, comprises about 10% or less, about 5% or less, about 2% or less, about 0.1% to about 10%, or about 0.1% to about 10%, of one or more than one or all of the following when compared to the corresponding wild-type barley plant;

i) B-hordeins comprising a sequence of amino acids provided as SEQ ID NO:53, ii) B-hordeins comprising a sequence of amino acids provided as SEQ ID NO:54, iii) C-hordeins comprising a sequence of amino acids provided as SEQ ID NO:55, and iv) D-hordeins comprising a sequence of amino acids provided as SEQ ID NO:56.

In another embodiment, the grain, or malt, wort, flour or wholemeal produced from said grain, further comprises about 10% or less, about 5% or less, about 1% or less, about 0.1% to about 10%, or about 0.1% to about 10%, of the following when compared to the corresponding wild-type barley plant;

i) γ-hordeins comprising a sequence of amino acids provided as SEQ ID NO:57, and/or ii) avenin-like A proteins comprising a sequence of amino acids provided as SEQ ID NO:52.

In another embodiment, the grain, or malt, wort, flour or wholemeal produced from said grain, further comprises a γ3-hordein, in an amount about 60% or less when compared to the amount in the corresponding wild-type barley plant, the γ3-hordein comprising amino acids whose sequence is provided as SEQ ID NO:58, such as a γ3-hordein comprising amino acids whose sequence is provided as SEQ ID NO:83.

Examples of a wild-type barley plant include, but are not limited to, Bomi, Sloop, Baudin, Yagan, Hindmarsh, or Commander.

In another embodiment, the starch content of the grain is at least about 50% (w/w). More preferably, the starch content of the grain is about 50% to about 70% (w/w).

In a further embodiment, the coeliac toxicity of flour produced from the grain is less than about 5%, or less than about 1%, of flour produced from grain of a corresponding wild-type barley plant.

In a further embodiment, the average grain weight is at least 1.05 fold, at least 1.1 fold, or 1.05 to 1.3 fold, higher than a grain which is i) homozygous for an allele of the Hor2 locus where most or all of the B-hordein encoding genes have been deleted, ii) homozygous for an allele at the Lys3 locus of barley which results in the grain lacking C hordeins, and iii) homozygous for a wild type allele of D hordein encoding a full-length protein.

In yet a further embodiment, the grain is from a plant which has a grain yield which is least 1.20 fold, or at least 1.35 fold, or 1.2 to 1.5 fold, or 1.2 to 2.0 fold higher than the grain yield from a plant which is i) homozygous for an allele of the Hor2 locus where most or all of the B-hordein encoding genes have been deleted, ii) homozygous for an allele at the Lys3 locus of barley which results in the grain lacking C hordeins, and iii) homozygous for a wild type allele of D hordein encoding a full-length protein.

For example, with regard to the two above embodiments, the grain with the features defined in i) to iii) may be G1* grain described in WO 2009/021285.

In another embodiment, at least about 50%, at least about 60%, at least about 70%, at least about 80%, at least about 90%, or at least about 95%, of the genome of the barley grain is identical to the genome of a barley wild type cultivar such as, but not limited to, Sloop, Hindmarsh, Oxford or Maratime.

In an embodiment, the grain is from a non-transgenic plant.

In an alternate embodiment, the grain is from a transgenic plant.

In a further embodiment, the plant comprises a transgene which encodes a polynucleotide which down-regulates the production of at least one hordein in the grain. Preferably, the polynucleotide of this embodiment is an antisense polynucleotide, a sense polynucleotide, a catalytic polynucleotide, an artificial microRNA or a duplex RNA molecule which down-regulates expression of one or preferably more genes encoding hordeins.

In another embodiment, the method comprises producing flour or wholemeal from the grain.

In a further embodiment, the method comprises producing malt from the grain.

In an embodiment, the malt-based beverage is beer and the method comprises germinating the grain or cracked grain derived therefrom. In an embodiment, the method further comprises fractionating dried germinated grain into two or more of an endosperm fraction, an endothelial layer fraction, a husk fraction, an acrospire fraction, and a malt rootlets fraction; and combining and blending predetermined amounts of two or more of the fractions.

In an embodiment, at least about 50% of the grain germinates within 3 days following imbibition.

In a further embodiment, the food ingredient or malt-based beverage ingredient is flour, starch, malt, or wort, or wherein the food is leavened or unleavened breads, pasta, noodles, breakfast cereals, snack foods, cakes, pastries or foods containing flour-based sauces.

In an embodiment, the malt-based beverage is beer or whiskey.

In an embodiment, the food or malt-based beverage is for human consumption.

In a further embodiment, following consumption of the food or drink at least one symptom of coeliac's disease is not developed by a subject with said disease.

In another aspect, the present invention provides a barley plant which produces grain comprising about 50 ppm or less hordeins.

Also provided is grain of a barley plant of the invention.

Grain of the invention and/or grain of a barley plant of the invention may comprise one or more of the features defined above.

In an embodiment, the barley grain is capable of producing a barley plant of the invention In an embodiment, the grain has been processed so that it is unable to germinate. In an embodiment, the grain is hull-less.

In another aspect, the present invention provides a method of producing barley grain, the method comprising;

a) growing a barley plant of the invention, b) harvesting the grain, and c) optionally processing the grain.

In an embodiment, the method comprises growing at least 10,000 plants in a field in an area of at least one hectare.

In another aspect, the present invention provides a method of producing flour, wholemeal, starch, malt, wort or other product obtained from grain, the method comprising;

a) obtaining grain of the invention, and b) processing the grain to produce the flour, wholemeal, starch, malt, wort or other product.

Also provided is a product produced from a barley plant of the invention, or grain of the invention.

In one embodiment, the product is a food ingredient, malt-based beverage ingredient, food product or malt-based beverage product.

In an embodiment, the malt-based beverage product is beer or whiskey.

In a further embodiment, the product is a non-food product. Examples include, but are not limited to, films, coatings, adhesives, building materials and packaging materials.

Also provided is a food or malt-based beverage produced using a method of the invention.

In another aspect, provided is beer comprising one or more barley grain proteins and less than 0.9 ppm hordeins.

In an embodiment, the beer comprises at least about 2%, at least about 3%, at least about 4%, or at least about 5%, ethanol.

In another aspect, the present invention provides flour or wholemeal comprising one or more barley grain proteins and less than about 50 ppm, or less than about 20 ppm, hordeins.

In another aspect, the present invention provides malt or wort comprising one or more barley grain proteins and less than about 50 ppm, or less than about 20 ppm, hordeins.

In a further aspect, the present invention provides a method of identifying an allele of a barley D hordein gene which encodes a truncated D hordein, the method comprising i) obtaining a sample comprising nucleic acids from a barley plant, and ii) analysing the sample for the presence or absence of a guanine residue at position 450 of the open reading frame encoding D hordein, wherein the presence of the guanine indicates the D hordein gene encodes a truncated D hordein.

In an embodiment, step b) comprises amplifying genomic DNA using the primers GGCAATACGAGCAGCAAAC (SEQ ID NO: 66) and CCTCTGTCCTGGTTGTTGTC (SEQ ID NO: 67), or a variant of one or both thereof, and contacting products of the amplification with the restriction enzyme KpnI, wherein the absence of cleavage indicates the D hordein gene encodes a truncated D hordein.

In a further aspect, the present invention provides a method of avoiding or reducing the incidence or severity of coeliac's disease in a subject, the method comprising orally administering to the subject a food or malt-based beverage of the invention, or a grain of the invention, wherein the reduction of the incidence or severity of coeliac's disease is relative to when the subject is orally administered the same amount of a corresponding food or malt-based beverage made from wild-type barley grain.

Also provided is the use of a food or malt-based beverage of the invention, or a grain of the invention, for the manufacture of a food or beverage for orally administering to a subject to avoid or reduce the incidence or severity of coeliac's disease.

In a further aspect, the present invention provides a method for identifying barley grain which can be used to produce a food and/or malt-based beverage for consumption by a subject with coeliac's disease comprising a) obtaining one or more of the following materials;

i) a sample from a plant capable of producing said grain, ii) the grain, iii) malt produced from the grain, and/or iv) an extract of said grain, b) analysing the material from step a) for the levels of B, C and D hordeins, peptides derived from B, C and D hordeins, and/or for alleles of B, C and D hordein genes, c) selecting grain which comprises about 50 ppm or less hordeins for producing a food and/or malt-based beverage for consumption by a subject with coeliac's disease.

In an embodiment, the material from step a) comprises genomic DNA and step b) comprises identifying the absence or presence of alleles of genes encoding one or more or all of;

i) B-hordeins comprising a sequence of amino acids provided as SEQ ID NO:53, ii) B-hordeins comprising a sequence of amino acids provided as SEQ ID NO:54, iii) C-hordeins comprising a sequence of amino acids provided as SEQ ID NO:55, and iv) D-hordeins comprising a sequence of amino acids provided as SEQ ID NO:56, wherein the absence of the alleles identifies grain which comprises about 50 ppm or less hordeins.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionallyequivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Schematic representation of barley chromosome 1.

Figure 2:
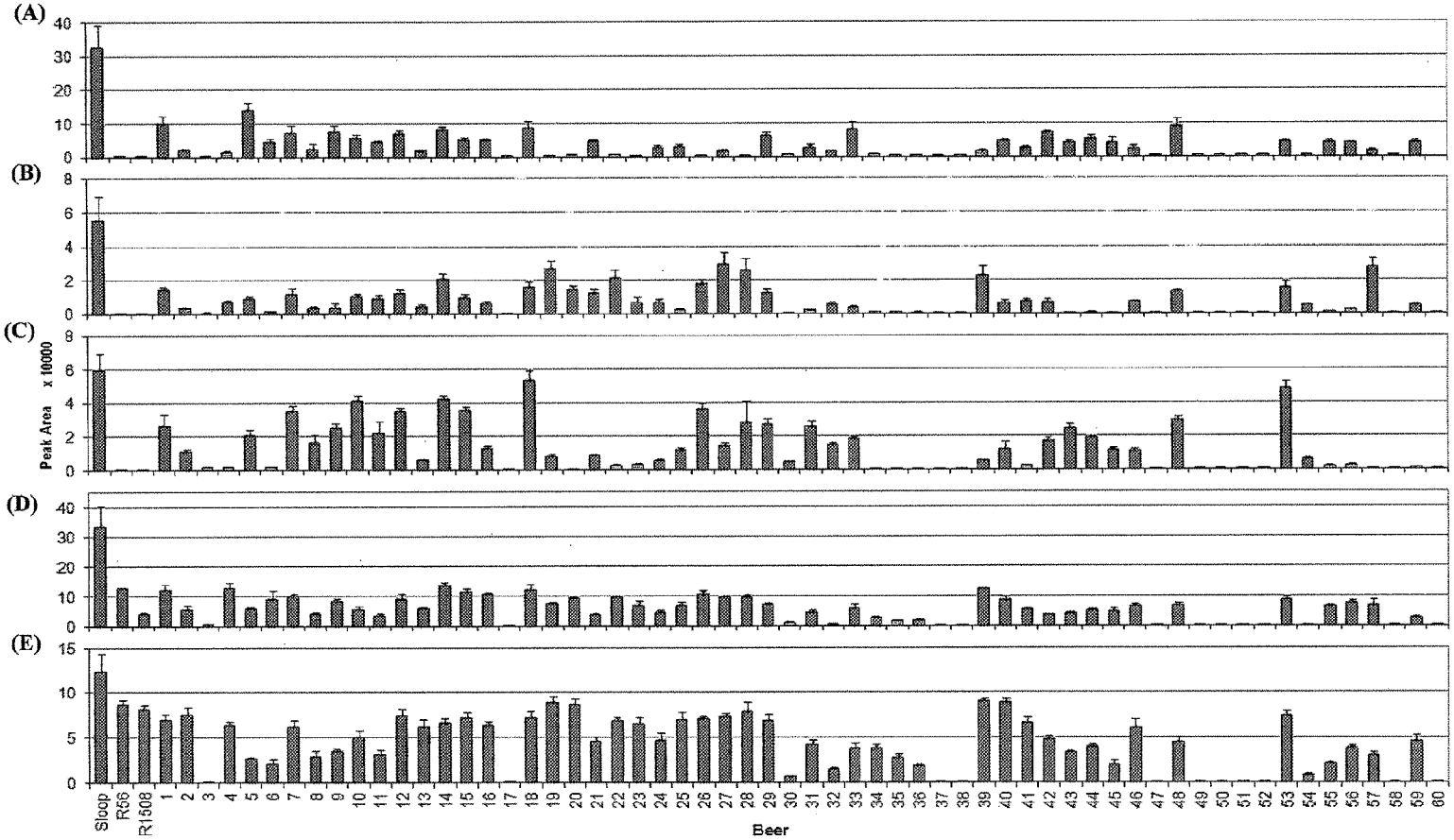

FIG. 2. Relative hordein quantitation in beers. The peak area of selected peptides representing the most abundant hordeins or related polypeptides detected in beer (A) QQCCQPLAQISEQAR (SEQ ID NO: 5) representing avenin-like A protein; (B) VFLQQQCSPVR (SEQ ID NO: 53) representing B1-hordein; (C) VFLQQQCSPVPMPQR (SEQ ID NO: 54) representing B3-hordein; (D) ELQESSLEACR (SEQ ID NO: 56) representing D-hordein; and (E) QQCCQQLANINEQSR (SEQ ID NO: 58) representing γ-hordein-3. These representative peptides were used to illustrate the relative amount of the major hordein proteins in wild-type (Sloop) and two hordein deletion beers made from Risø 56 and Risø 1508, respectively, and in 60 commercial beers. The small peak area seen for the gluten free beers 17, 47, 49-52, 54 was due to a low level of noise in the signal, and not due to detection of hordein.

FIG. 3. Comparison of D hordein amino acid sequences from Sloop (wild type) (*SEQ ID NO: 74*) and Ethiopia R118 (null) (*SEQ ID NO: 75*).

FIG. 4. Comparison of D hordein amino acid and coding nucleotides sequences from Sloop (wild type) (*SEQ ID NOs: 74 and 72, respectively*) and Ethiopia R118 (null) (*SEQ ID NOs 75 and 73, respectively*). The position of the primers for the detection of each allele (*SEQ ID NOs: 66 and 67*) is shown along with the KpnI cleavage site only present in the wild type sequence.

Figure 5:
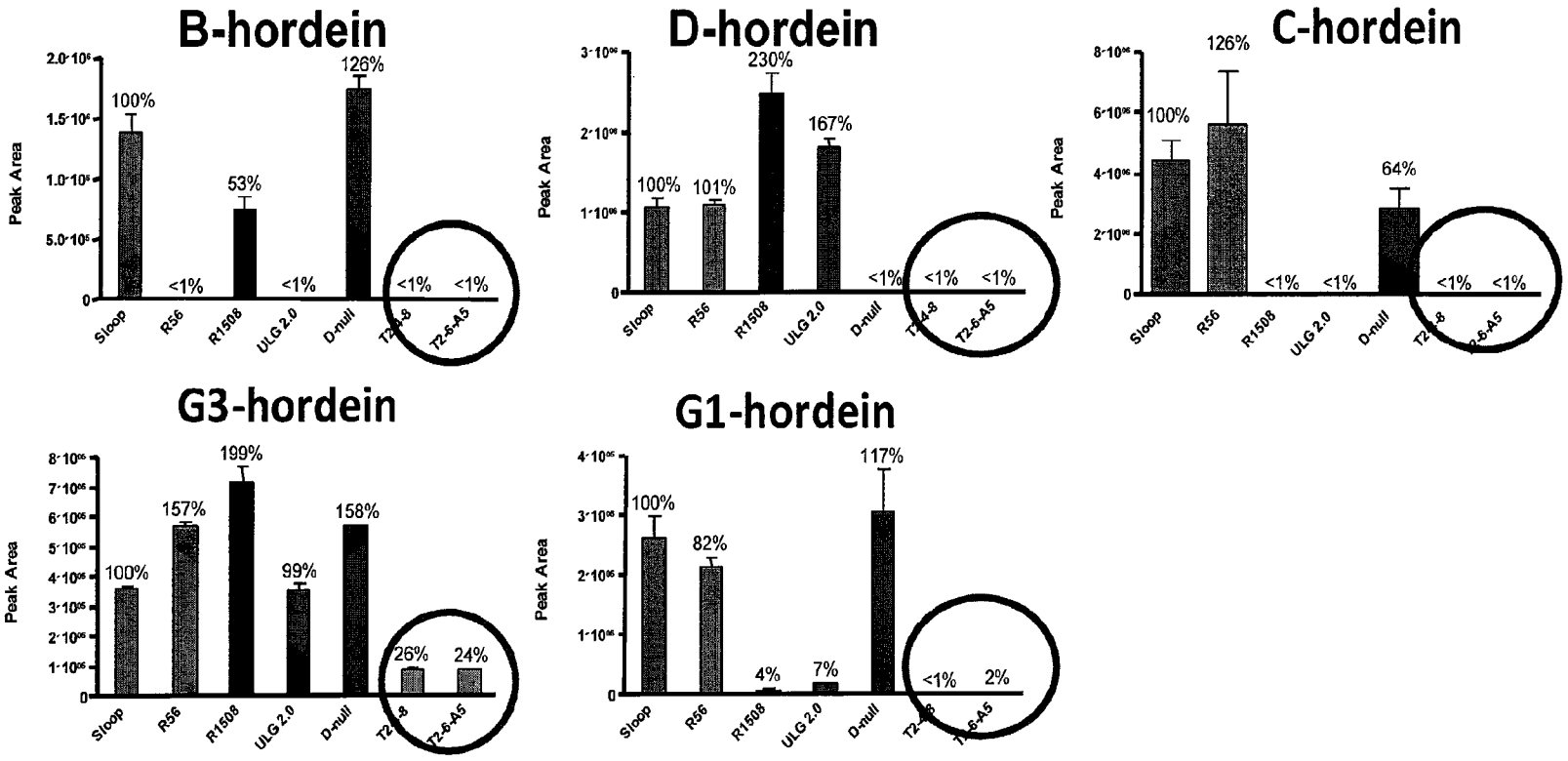

FIG. 5. Determination of hordein content of ULG3.0 lines by MRM MS by peak area, and indicating percentage relative to Sloop (100%).

Figure 6:
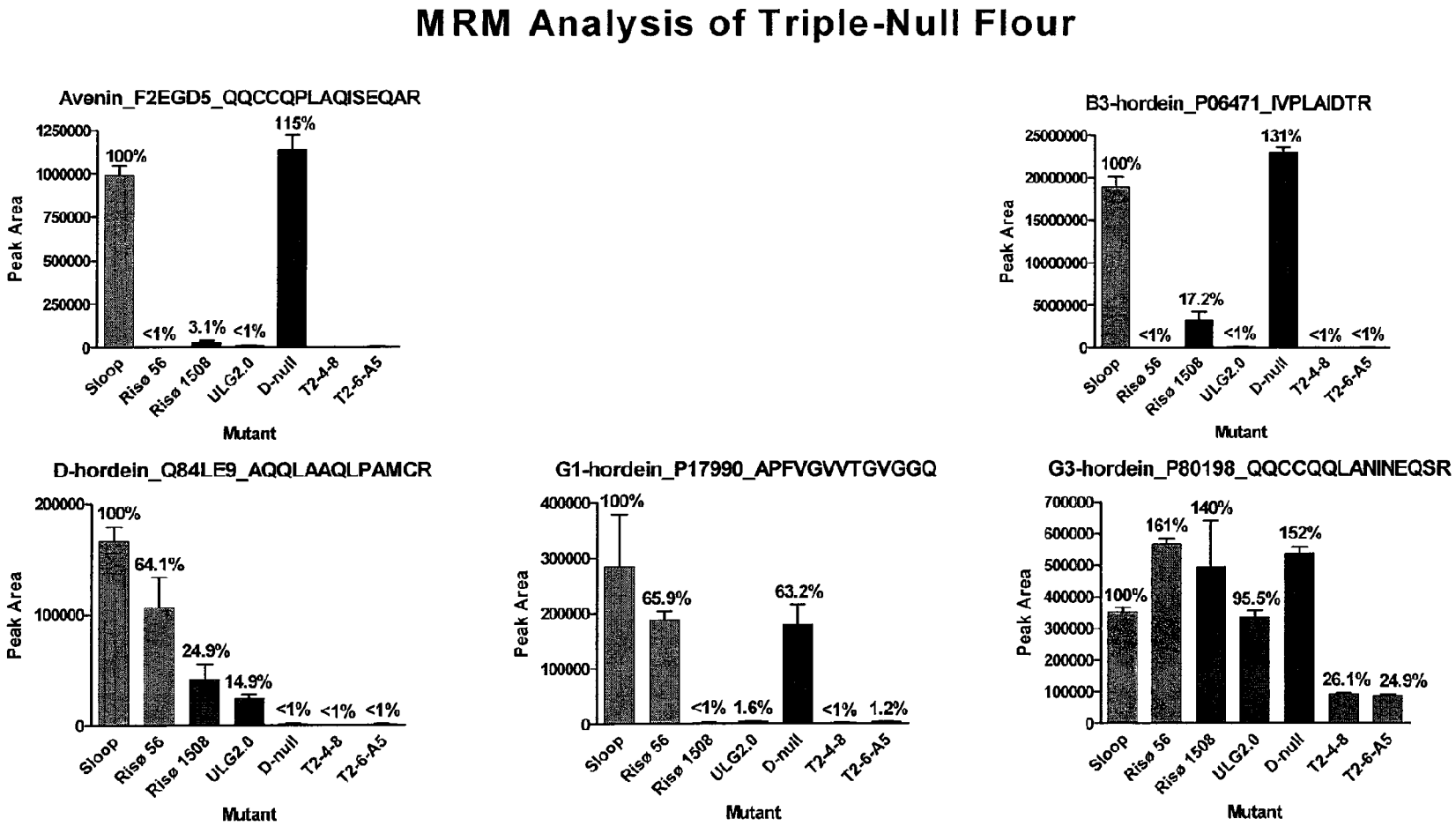

FIG. 6. Determination of hordein content of ULG3.0 lines by MRM MS by peak area, and indicating percentage relative to Sloop (100%).

Figure 7:
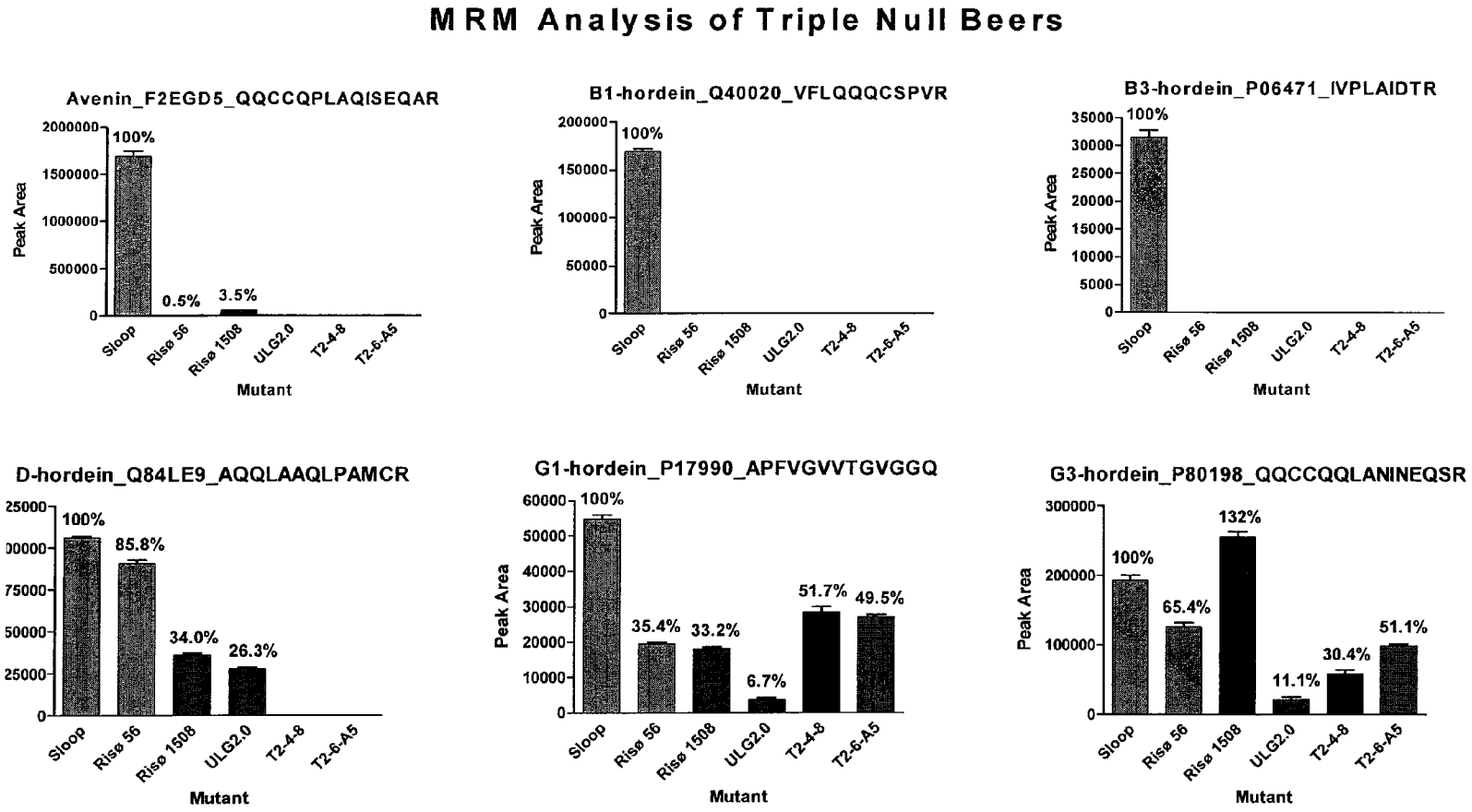

FIG. 7. Determination of hordein content of ULG3.0 beer by MRM MS as peak area for defined peptides. Peak areas are shown, and the percentage relative to Sloop (100%).

FIG. 8. Detection of hordeins and hordein-like proteins by MRM MS in flour from ULG3.0 (T2-4-8) and ULG3.2 candidate lines, compared to wild-type varieties Sloop, Baudin, Commander and Hindmarsh. Each graph shows the mean +/− SD for the summed peak area (3 MRM transitions) for a representative peptide from each hordein family. In each case the peptide (sequence as listed in graph) maps to either an avenin-like A protein, B1-, B3-, C-, D-, γ1- or γ3-hordein. The Uniprot accession number is given in the legend (e.g. F2EGD5 for first example).

KEY TO THE SEQUENCE LISTING

SEQ ID NOs: 1 and 4—Wheat α-gliadin peptides.

SEQ ID NOs 2, 3, 6 to 11, 16 to 59 and 85—Barley hordein peptides.

SEQ ID NO: 5—Wheat avenin-like A peptide.

SEQ ID NOs 12 to 15—Rye prolamin peptides.

SEQ ID NOs 60 to 71—Oligonucleotide primers.

SEQ ID NO: 72—Genomic region encoding barley cv. Sloop D-hordein.

SEQ ID NO: 73—Genomic region encoding barley cv. Ethiopia 8118 D-hordein (null).

SEQ ID NO: 74—Barley cv. Sloop D-hordein.

SEQ ID NO: 75—Barley cv. Ethiopia R1118 D-hordein.

SEQ ID NO: 74—Barley cv. Sloop D-hordein.

SEQ ID NO: 75—Barley cv. Ethiopia 8118 D-hordein.

SEQ ID NO: 76—Open reading frame encoding barley cv. Sloop D hordein.

SEQ ID NO: 77—Open reading frame encoding barley cv. Ethiopia R118 D hordein.

SEQ ID NO: 78—Example of wild type barley B1-hordein (Accession: Q40020).

SEQ ID NO: 79—Example of wild type barley B3-hordein (Accession: Q4G3S1).

SEQ ID NO: 80—Example of wild type barley C-hordein (Accession: Q40055).

SEQ ID NO: 81—Example of wild type barley γ1-hordein (Accession: P17990).

SEQ ID NO: 82—Example of wild type barley γ2-hordein (Accession: Q70IB4).

SEQ ID NO: 83—Example of wild type barley γ3-hordein (Accession: P80198).

SEQ ID NO: 84—Example of wild type barley avenin-like A protein (Accession: F2EGD5).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in plant breeding, food technology, cell culture, molecular genetics, immunology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

A used herein, the term "barley" refers to any species of the Genus Hordeum, including progenitors thereof, as well as progeny thereof produced by crosses with other species. A preferred form of barley is the species Hordeum vulgare. The grains of most cultivars of barley grown commercially in the world today have covered (hulled) caryopses in which the so-called hull, which is the outer lemma and inner palea, is joined to the pericarp epidermis at maturity. Other cultivars, termed hull-less or naked barleys, are free threshing and the hulls are easily removed in the threshing process. Naked barley grains are preferred for human consumption, although hulled grain can be used after pearling, whereas hulled barley grain is preferred for the brewing industry and for animal feed. The hull-less grain trait is controlled by a single, recessive gene designated nud located on the long arm of chromosome 7H (Kikuchi et al., 2003).

Coeliac disease or celiac disease is an autoimmune disorder of the small intestine that occurs in genetically predisposed individuals in all age groups after early infancy. It affects approximately 1% of Indo-European populations, though it is significantly underdiagnosed. Coeliac disease is caused by a reaction to gliadin, a gluten protein found in wheat (and similar proteins of Triticeae which includes other cultivars such as barley and rye). Upon exposure to gliadin, the enzyme tissue transglutaminase modifies the protein, and the immune system cross-reacts with the bowel tissue, causing an inflammatory reaction. This leads to flattening of the lining of the small intestine, which interferes with the absorption of nutrients. The only effective treatment is a lifelong gluten-free diet. This condition has several other names, including: coeliac disease (with ligature), c(o)eliac sprue, non-tropical sprue, endemic sprue, gluten enteropathy or gluten-sensitive enteropathy, and gluten intolerance. The symptoms of coeliac disease vary widely from person to person. Symptoms of coeliac's disease may include one or more of the following; gas, recurring abdominal bloating and pain, chronic diarrhea, constipation, pale, foul-smelling, or fatty stool, weight loss/weight gain, fatigue, unexplained anemia (a low count of red blood cells causing fatigue), bone or joint pain, osteoporosis, osteopenia, behavioral changes, tingling numbness in the legs (from nerve damage), muscle cramps, seizures, missed menstrual periods (often because of excessive weight loss), infertility, recurrent miscarriage, delayed growth, failure to thrive in infants, pale sores inside the mouth, called aphthous ulcers, tooth discoloration or loss of enamel, and itchy skin rash called dermatitis herpetiformis. Some of the more common symptoms include; tiredness, intermittent diarrhoea, abdominal pain or cramping, indigestion, flatulence, bloating; and weight loss. Ceoliac's disease can be diagnosed, for example, as described in WO 01/025793.

As used herein, the term "null allele of the gene encoding D-hordein at the Hor3 locus" refers to any allele of this locus which does not encode a D-hordein protein, or if a protein is encoded it is not immunogenic to a subject with coeliac's disease (such as the truncated D-hordein provided in FIG. 3).

As used herein, the term "lacking" as used herein in the context of a recited substance means that the substance is absent from the barley grain, or a product derived therefrom, of the invention, or that the substance is not detected in the grain or product of the invention when assays for the substance are performed using a method known in the art. That is, the substance may be present at a level that is insufficient for detection, or within the standard error for the assay for that substance. For example, in the context of a recited hordein, the term "lacking" means that the specific hordein is not detected in an assay such as, for example, an MRM MS assay, an ELISA assay or a 2D-gel electrophoresis assay, such as exemplified herein. The substance that is lacking may be undetected in one type of assay or in multiple types of assays. It would be appreciated that the substance that is said to be lacking in the grain or product of the invention is present, as readily determined by an assay known in the art, in the corresponding wild-type grain or product.

As used herein, the term "hordeins", for example when used in the phrase "about 50 ppm or less hordeins" and similar phrases refers to total hordeins including B-, C-, D- and γ-hordeins.

The terms "seed" and "grain" are used interchangeably herein. "Grain" generally refers to mature, harvested grain but can also refer to grain after processing such as, for example, milling or polishing, where most of the grain stays intact, or after imbibition or germination, according to the context. Mature grain commonly has a moisture content of less than about 18-20%. Wild-type barley grain (whole grain) generally contains 9-12% protein, and about 30-50% of this is prolamin, typically 35%, so wild-type barley grain has about 3-4% prolamin by weight. Prolamins are found almost exclusively in the endosperm, which is about 70% of the wholegrain weight.

As used herein, the term "havest index" refers to the weight of the harvested grain as a percentage of the total weight of the plant.

As used herein, the term "corresponding wild-type" barley plant refers to a plant which comprises at least 50%, more preferably at least 75%, more preferably at least 95%, more preferably at least 97%, more preferably at least 99%, and even more preferably 99.5% of the genotype of a plant of the invention, but produces grain with unmodified hordein levels. In one embodiment, the "corresponding wild-type" barley plant is a cultivar used in plant breeding experiments to introduce genetic variants that result in reduced hordein production in the grain. In another embodiment, the "corresponding wild-type" barley plant is a parental cultivar into which a transgene has been introduced which reduces hordein production in the grain. In a further embodiment, the "corresponding wild-type" barley plant is a cultivar that is used at the date of filing for the commercial production of barley grain such as, but not limited to, Bomi, Sloop, Carlsberg II, K8, L1, Vlamingh, Stirling, Hamelin, Schooner, Baudin, Commander, Gairdner, Buloke, WI3586-1747, WI3416, Flagship, Cowabbie, Franklin, SloopSA, SloopVic, Quasar, VB9104, Grimmett, Cameo*Arupo 31-04, Prior, Schooner, Unicorn, Harrington, Torrens, Galleon, Morex, Dhow, Capstan, Fleet, Keel, Maritime, Yarra, Dash, Doolup, Fitzgerald, Molloy, Mundah, Oxford, Onslow, Skiff, Unicorn, Yagan, Chebec, Hindmarsh, Chariot, Diamant, Korai, Rubin, Bonus, Zenit, Akcent, Forum, Amulet, Tolar, Heris, Maresi, Landora, Caruso, Miralix, Wikingett Brise, Caruso, Potter, Pasadena, Annabell, Maud, Extract, Saloon, Prestige, Astoria, Elo, Cork, Extract, Laura. In an embodiment, the "corresponding wild-type" barley plant produces grain with unmodified hordein levels due to it comprising a full complement of functional hordein genes encoding functional hordein proteins, including the B, C, D and γ-hordeins encoded by the Hor2, Hor1, Hor3, and Hor5 loci.

As used herein, the term "one or more barley grain proteins" refers to naturally occurring proteins produced by barley grain other than hordeins. Examples of such proteins are known to those skilled in the art. Specific examples include, but are not limited to, barley albumins such as the 9 kDa lipid transfer protein 1 (LTP1) (see Douliez et al. (2000) for a review and Swiss-prot Accession No. P07597 as an example), the α-amylase trypsin inhibitors (CMd, CMb, CMa), protein Z (see Brandt et al. (1990) and Genbank Accession No. P06293), and proteins identified in Colgrave et al. (2012), including processed (mature) forms thereof, as well as denatured forms and/or fragments thereof produced as a result of the production of malt, flour, wholemeal, food or malt-based beverage of the invention.

As used herein, "average weight of the grain" is preferably determined by obtaining at least 25, at least 50 or at least 100, more preferably about 100, individual grains from a plant (or genetically identical plants grown under the same conditions) and determining the average weight of the grain.

As used herein, the term "malt" is used to refer to barley malt, "flour" to refer to barley flour, "wholemeal" to refer to barley wholemeal, and "beer" to refer to beer which is produced using barley as its main ingredient providing fermentable carbohydrate, except where the malt, flour, wholemeal or beer is explicitly stated to come from a source other than barley. As used herein, "wort" refers to the liquid extracted from the mashing process during the brewing of beer or whisky. Wort contains the sugars that will be fermented by the brewing yeast to produce alcohol. More specifically, a source of malt, wort, flour, beer, wholemeal, food product etc of the invention is from the processing (for example, milling and/or fermentation) of barley grain. The grain, malt, wort, flour, wholemeal or beer of the invention may be mixed or blended with grain, malt, wort, flour, wholemeal or beer which is not derived from barley. These terms include malt, wort, flour, beer, wholemeal, food product etc produced from a mixture of grains including barley. In a preferred embodiment, at least 10% or at least 50% of the grain used to produce the malt, wort, flour, beer, wholemeal, food product etc is barley grain.

The term "plant" as used herein as a noun refers to a whole plant such as, for example, a plant growing in a field for commercial barley production. A "plant part" refers to plant vegetative structures (for example, leaves, stems), roots, floral organs/structures, seed (including embryo, endosperm, and seed coat), plant tissue (for example, vascular tissue, ground tissue, and the like), cells, starch granules or progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

"Nucleic acid molecule" refers to a polynucleotide such as, for example, DNA, RNA or oligonucleotides. It may be DNA or RNA of genomic or synthetic origin, double-stranded or single-stranded, and combined with carbohydrate, lipids, protein, or other materials to perform a particular activity defined herein.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "other food or beverage ingredient" refers to any substance suitable for consumption by an animal, preferably any substance suitable for consumption by a human, when provided as part of a food or beverage. Examples include, but are not limited to, grain from other plant species, sugar, etc, but excluding water.

Plants of the invention typically have one or more genetic variations which each result in reduced levels of at least one hordein, more preferably at least B, C and D-hordeins. As used herein, the term "genetic variation which each results in reduced levels of at least one hordein" refers to any polymorphism of a barley plant that reduces hordein production. The genetic variation may comprise, for example, a deletion of a hordein gene(s) or part thereof, or a mutation which reduce barley gene transcription. Examples of such genetic variations are present in Risø 56, Risø 527 and Risø 1508 and Ethiopia R118. Hence, such plants may be used as parental plants to produce the plants of the invention. A plant of the invention may result from the progeny from a cross between any of these barley mutants. In a preferred embodiment, a plant of the invention is not the progeny from a cross between Risø 56 and Risø 1508 comprising the hor2 and lys3 mutations present in these lines and which is wild-type for the gene encoding D-hordein. In an embodiment, the plant encodes γ3-hordein comprising amino acids whose sequence is provided as SEQ ID NO:58, such as a γ3-hordein comprising amino acids whose sequence is provided as SEQ ID NO:83. For instance, the plant may have a functional wild type γ3-hordein gene such as the γ3-hordein gene of barley cultivar Bomi, Sloop, Baudin, Yagan, Hindmarsh, or Commander. In an embodiment, the plant is not the progeny from a cross between Risø 527 and Rise 1508.

As used herein, unless stated to the contrary, the phrase "about" refers to any reasonable range in light of the value in question. In a preferred embodiment, the term "about" refers to +/−10%, more preferably +/−5%, more preferably +/−1%, the specified value.

Unless specified otherwise, when referring to weight and a percentage, the units are w/w.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Prolamins and Hordeins

Cereal prolamins (known as gliadins in wheat, hordeins in barley, secalins in rye, avenins in oats, and zeins in maize) are the main endosperm storage proteins in all cereal grains, with the exception of oats and rice (Shewry and Halford, 2002). Hordeins represent 35-50% of the total protein in barley seeds (Jaradat, 1991). They are classified into four groups, A (also known as γ hordein), B, C, and D, in order of decreasing mobility (Field et al., 1982). B, C, D and γ-hordeins are encoded by the Hor2, Hor1, Hor3, and Hor5 loci, respectively, on chromosome 1H which is schematically represented in FIG. 1.

The B hordeins are the main protein fraction, differing from C hordeins in their sulphur content (Kreis and Shewry, 1989). B hordeins account for 70-80% of the total and C hordeins for 10-20% (Davies et al., 1993). The A hordeins are not generally considered to be a storage fraction whereas D hordeins are homologous to the high-molecular-weight glutenins. Hordeins, along with the rest of the related cereal prolamins, are not expressed in the zygotic embryo itself, unlike other storage proteins such as napins; they are believed to be expressed exclusively in the starchy endosperm during the middle-to-late stages of seed development.

Examples of barley hordein amino acid sequences and genes encoding them are provided in WO 2009/021285.

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the barley grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain of a barley plant of the invention, (ii) steeping said grain, (iii) germinating the steeped grains under predetermined conditions and (iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of speciality malts, including, but limited to, methods of roasting the malt. One non-limiting example is described in Example 6.

Malt may be prepared using only grain produced from barley plants of the invention or in mixtures comprising other grains.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

In another embodiment, wort compositions can be prepared from the malt. Said wort may be first and/or second and/or further wort. In general a wort composition will have a high content of amino nitrogen and fermentable carbohydrates, mainly maltose. Typically, wort is prepared by incubating malt with water, i.e. by mashing. During mashing, the malt/water composition may be supplemented with additional carbohydrate-rich compositions, for example barley, maize or rice adjuncts. Unmalted cereal adjuncts usually contain no active enzymes, and therefore rely on malt or exogenous enzymes to provide enzymes necessary for sugar conversion.

In general, the first step in the wort production process is the milling of malt in order that water may gain access to grain particles in the mashing phase, which is fundamentally an extension of the malting process with enzymatic depolymerization of substrates. During mashing, milled malt is incubated with a liquid fraction such as water. The temperature is either kept constant (isothermal mashing) or gradually increased. In either case, soluble substances produced in malting and mashing are extracted into said liquid fraction before it is separated by filtration into wort and residual solid particles denoted spent grains. This wort may also be denoted first wort. After filtration, a second wort is obtained. Further worts may be prepared by repeating the procedure. Non-limiting examples of suitable procedures for preparation of wort is described in Hoseney (supra).

The wort composition may also be prepared by incubating barley plants of the invention or parts thereof with one or more suitable enzyme, such as enzyme compositions or enzyme mixture compositions, for example Ultraflo or Cereflo (Novozymes). The wort composition may also be prepared using a mixture of malt and unmalted barley plants or parts thereof, optionally adding one or more suitable enzymes during said preparation. In addition, prolyl-endopeptidase enzymes which specifically destroy the toxic amino linkages involved in coeliac disease could be added during the fermentation of the wort to reduce the toxicity of the residual hordeins (De Angelis et al., 2007; Marti et al., 2005; Stepniak et al., 2006).

Grain Processing

Barley grain of the invention can be processed to produce a food ingredient, beverage ingredient, food or beverage, or non-food product using any technique known in the art.

In one embodiment, the product is whole grain flour (an ultrafine-milled whole grain flour, such as an ultrafine-milled whole grain flour; a whole grain flour, or a flour made from about 100% of the grain). The whole grain flour includes a refined flour constituent (refined flour or refined flour) and a coarse fraction (an ultrafine-milled coarse fraction).

Refined flour may be flour which is prepared, for example, by grinding and bolting cleaned barley. The Food and Drug Administration (FDA) requires flour to meet certain particle size standards in order to be included in the category of refined barley flour. The particle size of refined flour is described as flour in which not less than 98% passes through a cloth having openings not larger than those of woven wire cloth designated "212 micrometers (U.S. Wire 70)".

The coarse fraction includes at least one of: bran and germ. For instance, the germ is an embryonic plant found within the barley kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. Preferably, the coarse fraction is homogenously blended with the refined flour constituent. Homogenously blending the coarse fraction and refined flour constituent may help reduce stratification of the particles by size during shipping. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. It is contemplated by the present invention that inactivated may also mean inhibited, denatured, or the like. Stabilization is a process that uses steam, heat, radiation, or other treatments to inactivate the enzymes found in the bran and germ layer. Naturally occurring enzymes in the bran and germ will catalyze changes to compounds in the flour, adversely affecting the cooking characteristics of the flour and the shelf life. Inactivated enzymes do not catalyze changes to compounds found in the flour, therefore, flour that has been stabilized retains its cooking characteristics and has a longer shelf life. For example, the present invention may implement a two-stream milling technique to grind the coarse fraction. Once the coarse fraction is separated and stabilized, the coarse fraction is then ground through a grinder, preferably a gap mill, to form a coarse fraction having a particle size distribution less than or equal to about 500 micrometers. In an exemplary embodiment, the gap mill tip speed normally operates between 115 m/s to 144 m/s, the high tip speed generates heat. The heat generated during the process and the airflow lead to a decrease in the microbial load of the coarse fraction. In further embodiments, prior to grinding in a gap mill, the coarse fraction may have an average aerobic plate count of 95,000 colony forming units/gram (cfu/g) and an average coliform count of 1,200 cfu/g. After passing through the gap mill the coarse fraction may have an average aerobic plate count of 10,000 cfu/g and an average coliform count of 900 cfu/g. Thus, the microbial load may be noticeably decreased in the coarse fraction of the present invention. After sifting, any ground coarse fraction having a particle size greater than 500 micrometers may be returned to the process for further milling.

In additional embodiments, the whole grain flour or the coarse fraction may be a component of a food product. For example, the food product may be a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour or coarse fraction may be a component of a nutritional supplement. For instance, the nutritional supplement may be a product that is added to the diet containing one or more ingredients, typically including: vitamins, minerals, herbs, amino acids, enzymes, antioxidants, herbs, spices, probiotics, extracts, prebiotics and fiber. The whole grain flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. Further, 14 grams is all that is needed to deliver 20% of an individuals daily recommend consumption of fiber. Thus, the coarse fraction is an excellent supplemental source for consumption of an individual's fiber requirement. Therefore, in a present embodiment, the whole grain flour or coarse fraction may be a component of a nutritional supplement. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients.

In additional embodiments, the whole grain flour or coarse fraction may be a fiber supplement or a component thereof. Many current fiber supplements such as psyllium husks, cellulose derivatives, and hydrolyzed guar gum have limited nutritional value beyond their fiber content. Additionally, many fiber supplements have a undesirable texture and poor taste. Fiber supplements made from the whole grain flour or coarse fraction may help deliver fiber as well as protein, and antioxidants. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour, multi-barley flour, or a multi-grain coarse fraction. For example, bran and germ from one type of barley may be ground and blended with ground endosperm or whole grain barley flour of another type of barley. Alternatively bran and germ of one type of grain may be ground and blended with ground endosperm or whole grain flour of another type of grain. In an additional embodiment, bran and germ from a first type of barley or grain may be blended with bran and germ from a second type of barley or grain to produce a multi-grain coarse fraction. It is contemplated that the present invention encompasses mixing any combination of one or more of bran, germ, endosperm, and whole grain flour of one or more grains. This multi-grain, multi-barley approach may be used to make custom flour and capitalize on the qualities and nutritional contents of multiple types of grains or barleys to make one flour.

The whole grain flour of the present invention may be produced via a variety of milling processes. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. In one embodiment, the grinder may be a gap mill. After grinding, the grain is discharged and conveyed to a sifter. Any sifter known in the art for sifting a ground particle may be used. Material passing through the screen of the sifter is the whole grain flour of the present invention and requires no further processing. Material that remains on the screen is referred to as a second fraction. The second fraction requires additional particle reduction. Thus, this second fraction may be conveyed to a second passage grinder. After grinding, the second fraction may be conveyed to a second sifter. Material passing through the screen of the second sifter is the whole grain flour of the present invention. The material that remains on the screen is referred to as the fourth fraction and requires further processing to reduce the particle size. The fourth fraction on the screen of the second sifter is conveyed back into either the first passage grinder or the second passage grinder for further processing via a feedback loop. In an alternative embodiment of the invention, the process may include a plurality of first pass grinders to provide a higher system capacity.

It is contemplated that the whole grain flour, coarse fraction and/or grain products of the present invention may be produced by any milling process known in the art. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Polynucleotides which Down-Regulate the Production of a Hordein

In one embodiment, grain of the invention, and/or used in the methods of the invention, is from a transgenic barley plant which comprises a transgene which encodes a polynucleotide which down-regulates the production of at least one hordein in the grain. Examples of such polynucleotides include, but are not limited to, antisense polynucleotide, a sense polynucleotide, a catalytic polynucleotide, an artificial microRNA or a duplex RNA molecule. When present in the grain, each of these polynucleotides result in a reduction in hordein mRNA available for translation.

Antisense Polynucleotides

The term "antisense polynucletoide" shall be taken to mean a DNA or RNA, or combination thereof, molecule that is complementary to at least a portion of a specific mRNA molecule encoding a hordein and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque (1995) and Senior (1998). Senior (1998) states that antisense methods are now a very well established technique for manipulating gene expression.

An antisense polynucleotide in a barley plant of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as a barley hordein under normal conditions in a barley cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al., 1992) and the hairpin ribozyme (Shippy et al., 1999).

The ribozymes in barley plants of the invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example an mRNA encoding a barley hordein) under "physiological conditions", namely those conditions within a barley cell.

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and antisense sequences are flanked by an unrelated sequence which enables the sense and antisense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Constructs

Nucleic acid constructs useful for producing transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the seed.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of Arabidopsis, the rice actin I gene promoter, the mannopine synthase and octopine synthase promoters, the Adh promoter, the sucrose synthase promoter, the R gene complex promoter, and the chlorophyll $\alpha/\beta$ binding protein gene promoter. These promoters have been used to create DNA vectors that have been expressed in plants; see, e.g., WO 84/02913. All of these promoters have been used to create various types of plant-expressible recombinant DNA vectors.

The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to the use of constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of Agrobacterium tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the barley cells, or allow the utilization of substrates such as mannose. The selectable marker preferably confers hygromycin resistance to the barley cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes the use of a recombinant vector, which includes at least transgene outlined herein, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Transgenic Plants

Transgenic barley plants, as defined in the context of the present invention include plants (as well as parts and cells of said plants) and their progeny which have been genetically modified using recombinant techniques to cause production of at least one polynucleotide and/or polypeptide in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) rogeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art. Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of Agrobacterium infection are required. An illustrative embodiment of a method for delivering DNA into Zea mays cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

Modern Agrobacterium transformation vectors are capable of replication in E. coli as well as Agrobacterium, allowing for convenient manipulations as described (Klee et al., In: Plant DNA Infectious Agents, Hohn and Schell, eds., Springer-Verlag, New York, pp. 179-203 (1985). Moreover, technological advances in vectors for Agrobacterium-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant varieties where Agrobacterium-mediated transformation is efficient, it is the method of choice because of the facile and defined nature of the gene transfer.

A transgenic plant formed using Agrobacterium transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of Agrobacterium tumefaciens, and obtaining transgenic plants have been published for cotton (U.S. Pat. Nos. 5,004,863, 5,159,135, 5,518,908); soybean (U.S. Pat. Nos. 5,569,834, 5,416,011); Brassica (U.S. Pat. No. 5,463,174); peanut (Cheng et al., 1996); and pea (Grant et al., 1995).

Methods for transformation of cereal plants such as barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, PCT/US97/10621, U.S. Pat. Nos. 5,589,617, 6,541,257, and WO 99/14314. Preferably, transgenic barley plants are produced by Agrobacterium tumefaciens mediated transformation procedures. Vectors carrying the desired nucleic acid construct may be introduced into regenerable barley cells of tissue cultured plants or explants, or suitable plant systems such as protoplasts.

The regenerable barley cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Production of Mutant Plants

There are many techniques known in the art which can be used to produce barley with reduced levels of hordeins by mutating endogenous hordeins genes, including, but not limited to, TILLING, zinc finger nuclease, TAL effector nuclease (TALEN), and Clustered Regularly Interspaced Short Palindromic Repeats (CRSPR).

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005) and Henikoff et al., (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Genome Editing Using Site-Specific Nucleases

Genome editing uses engineered nucleases composed of sequence specific DNA binding domains fused to a non-specific DNA cleavage module. These chimeric nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes.

In the absence of donor plasmid, NHEJ-mediated repair yields small insertion or deletion mutations of the target that cause gene disruption.

Engineered nucleases useful in the methods of the present invention include zinc finger nucleases (ZFNs) and transcription activator-like (TAL) effector nucleases (TALEN).

Typically nuclease encoded genes are delivered into cells by plasmid DNA, viral vectors or in vitro transcribed mRNA. The use of fluorescent surrogate reporter vectors also allows for enrichment of ZFN- and TALEN-modified cells. As an alternative to ZFN gene-delivery systems, cells can be contacted with purified ZFN proteins which are capable of crossing cell membranes and inducing endogenous gene disruption.

Complex genomes often contain multiple copies of sequences that are identical or highly homologous to the intended DNA target, potentially leading to off-target activity and cellular toxicity. To address this, structure (Miller et al., 2007; Szczepek et al., 2007) and selection based (Doyon et al., 2011; Guo et al., 2010) approaches can be used to generate improved ZFN and TALEN heterodimers with optimized cleavage specificity and reduced toxicity.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the $Cis_2His_2$ type of zinc finger that is very generally represented, for example, by the zinc finger transcription factors TFIIIA or Sp1. In a preferred embodiment, the zinc finger domain comprises three $Cis_2His_2$ type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques. (see, for example, Bibikova et al., 2002).

The ZFN DNA-cleavage domain is derived from a class of non-specific DNA cleavage domains, for example the DNA-cleavage domain of a Type II restriction enzyme such as FokI (Kim et al., 1996). Other useful endonucleases may include, for example, HhaI, HindIII, Nod, BbvCI, EcoRI, BglI, and AlwI.

A linker, if present, between the cleavage and recognition domains of the ZFN comprises a sequence of amino acid residues selected so that the resulting linker is flexible. Or, for maximum target site specificity, linkerless constructs are made. A linkerless construct has a strong preference for binding to and then cleaving between recognition sites that are 6 bp apart. However, with linker lengths of between 0 and 18 amino acids in length, ZFN-mediated cleavage occurs between recognition sites that are between 5 and 35 bp apart. For a given linker length, there will be a limit to the distance between recognition sites that is consistent with both binding and dimerization. (Bibikova et al., 2001). In a preferred embodiment, there is no linker between the cleavage and recognition domains, and the target locus comprises two nine nucleotide recognition sites in inverted orientation with respect to one another, separated by a six nucleotide spacer.

In order to target genetic recombination or mutation according to a preferred embodiment of the present invention, two 9 bp zinc finger DNA recognition sequences must be identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a DNA cleavage domain.

ZFN activity can be improved through the use of transient hypothermic culture conditions to increase nuclease expression levels (Doyon et al., 2010) and co-delivery of site-specific nucleases with DNA end-processing enzymes (Certo et al., 2012). The specificity of ZFN-mediated genome editing can be improved by use of zinc finger nickases (ZFNickases) which stimulate HDR without activation the error-prone NHE-J repair pathway (Kim et al., 2012; Wang et al., 2012; Ramirez et al., 2012; McConnell Smith et al., 2009).

A transcription activator-like (TAL) effector nuclease (TALEN) comprises a TAL effector DNA binding domain and an endonuclease domain.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Genome Editing Using Programmable RNA-Guided DNA Endonucleases

Distinct from the site-specific nucleases described above, the clustered regulatory interspaced short palindromic repeats (CRISPR)/Cas system provides an alternative to ZFNs and TALENs for inducing targeted genetic alterations. In bacteria, the CRISPR system provides acquired immunity against invading foreign DNA via RNA-guided DNA cleavage.

CRISPR systems rely on CRISPR RNA (crRNA) and transactivating chimeric RNA (tracrRNA) for sequence-specific silencing of invading foreign DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPR loci are a distinct class of interspersed short sequence repeats (SSRs) that were first recognized in E. coli (Ishino et al., 1987; Nakata et al., 1989). Similar interspersed SSRs have, been identified in Haloferax mediterranei, Streptococcus pyogenes, Anabaena, and Mycobacterium tuberculosis (Groenen et al., 1993; Hoe et al., 1999; Masepohl et al., 1996; Mojica et al., 1995).

The CRISPR loci differ from other SSRs by the structure of the repeats, which have been termed short regularly spaced repeats (SRSRs) (Janssen et al., 2002; Mojica et al., 2000). The repeats are short elements that occur in clusters, that are always regularly spaced by unique intervening sequences with a constant length (Mojica et al., 2000). Although the repeat sequences are highly conserved between strains, the number of interspersed repeats and the sequences of the spacer regions differ from strain to strain (van Embden et al., 2000).

The common structural characteristics of CRISPR loci are described in Jansen et al., (2002) as (i) the presence of multiple short direct repeats, which show no or very little sequence variation within a given locus; (ii) the presence of non-repetitive spacer sequences between the repeats of similar size; (iii) the presence of a common leader sequence of a few hundred basepairs in most species harbouring multiple CRISPR loci; (iv) the absence of long open reading frames within the locus; and (v) the presence of one or more cas genes.

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

As used herein, the term "cas gene" refers to one or more cas genes that are generally coupled associated or close to or in the vicinity of flanking CRISPR loci. A comprehensive review of the Cas protein family is presented in Haft et al. (2005). The number of cas genes at a given CRISPR locus can vary between species.

EXAMPLES

Example 1. Materials and Methods

Plant Material

Barley line cv Sloop (wild-type) was obtained from the Australian Winter Cereals Collection (Tamworth, Australia). Risø 56 (expressing no B-hordeins) and Rise 1508 (expressing no C-hordeins and decreased D- and B-hordeins) (Doll, 1973; Doll, 1983) were obtained from the Nordic Germplasm Bank (Alnarp, Sweden). Risø 1508 was an ethyleneimine induced mutant carrying a mutation in the lys3a gene on chromosome 5H which reduced accumulation of C-hordeins. Each of these lines are publically available. Plants were grown in glasshouse conditions at 25° C. days and 20° C. nights and harvested seeds inspected to exclude contamination. For malting and brewing experiments, plants of cultivars Sloop, Risø 56 and Risø 1508 were grown side by side at CSIRO Ginninderra Experimental Station, Canberra, in the field, and 10 kg grain of each harvested. The grains were malted and 20 L batches of beer brewed using standard techniques.

Prolamin Extraction from Flour

To extract prolamins (alcohol-soluble proteins), grain was milled to wholemeal flour using standard techniques. Prolamins in aqueous washed wholemeal flour (10 g) were dissolved in 55% (v/v) propan-2-ol (HPLC grade), 2% (w/v) dithiothreitol (DTT) by incubation at 65° C. for 45 min, and precipitated with two volumes of propan-2-ol at −20° C. overnight. The precipitated prolamins were dissolved in 8 M urea, 1% DTT, 25 mM triethanolamine-HCl (pH 6), and purified by fast protein liquid chromatography (FPLC) on a 4 mL Resource RPC column (GE Healthcare, Sydney, NSW, Australia) eluted with a 30 mL linear gradient (at 2 mL/min) from 3% to 60% acetonitrile in 1% (v/v) trifluoroacetic acid (TFA).

Filter-Aided Sample Preparation (FASP) Method

Fifty μL of hordein extract was transferred to a PALL Nanosep 10 MWCO filter. 200 μL of 8 M urea (Sigma) in 0.1 M Tris/HCl pH 8.5 (UA) was added and the mixture centrifuged at 14000 rpm for 15 min at about 20° C. The flow-through from the tube was discarded. A further 200 μl of UA was added to the filter unit and re-centrifuged at 14,000 rpm for 15 min. 100 μIAA solution (0.05 M iodoacetamide in UA) was added and the sample mixed at 600 rpm in a thermo-mixer set at 20° C. for 1 min and then incubated without mixing for 20 min. 100 μl of UA was added to the filter unit and centrifuged at 14,000×g for 15 min. This step was repeated twice. 100 μl of 0.05M $NH_4HCO_3$ (ammonium bicarbonate, ABC) in water was added to the filter unit and centrifuged at 14,000×g for 10 min. This step was repeated twice. 40 μl ABC with 15 μL of trypsin stock (1.5 μg/μ1, Sigma) was added and each sample mixed at 600 rpm in a thermo-mixer for 1 min. The filter units were incubated in a wet chamber at 37° C. for 4-18 h for enzyme digestion. The filter units were transferred to new collection tubes and centrifuged at 14,000 rpm, for 10 min. 40 μl ABC was added and the filter units centrifuged again at 14,000 rpm for 10 min. This step was repeated once. The flow through fraction was acidified by adding 15 μL of 5% formic acid and lyophilised. The extracted, dried peptides were resuspended in 30 μL 0.5% formic acid for analysis by MRM.

Preparation of Wort and Beer

Barley was malted in a Joe White Micromalting System in several 800 g tins.

The steeping regime involved: 8 h soaking, 9 h rest, 5 h soaking at 17° C. (Sloop); 8 h soaking, 10 h rest, 5 h soaking at 17° C. (Risø 56); and 7 h soaking, 8 h rest, 3 h soaking at 17° C. (Risø 1508). Germination occurred over 94 h at 16° C. for Sloop and 15° C. for the two hordein deletion mutants. The kiln program was over 21 h between 50-80° C. The kilned malt was mashed as detailed in Colgrave et al. (2012). After the indicated amylase rest time, the mash was bought to the boil and boiled for 1 h to produce the wort. During boiling, the boiling wort was bittered with Tettnang hops to achieve 21-22 IBUs. The wort was cooled overnight to 20° C. and then fermented with Fermentis US-05 yeast at 18-20° C. to completion after about 2 weeks. The unfiltered beer was kegged, and force carbonated before bottling.

Analysis of Beer

A selection of 60 commercial beers were obtained as listed in Supplementary Table 1 of Colgrave et al. (2012). Triplicate samples (1 mL) were taken from two different bottles of each and degassed to remove $CO_2$ under reduced pressure. Aliquots (100 μL) of degassed beer were taken and were reduced by addition of 20 μL of 50 mM DTT under $N_2$ for 30 min at 60° C. To these solutions, 20 μL of 100 mM iodoacetamide (IAM) was added and the samples were incubated for 15 min at room temperature. To each solution 5 μL of 1 mg/mL trypsin (Sigma) or chymotrypsin (Sigma) was added and the samples incubated at 37° C. overnight. The digested peptide solution was acidified by addition of 10 μL of 5% formic acid and passed through a 10 kDa MW filter (Pall, Australia). The filtrate was lyophilized and reconstituted in 1% formic acid and stored at 4° C. until analysis.

Analysis of Undigested Wort and Beer

Wort and beer (0.1 mL) derived from the wild-type (Sloop) barley and hordein deletion mutants were passed through a 10 kDa molecular weight cut-off filter (Pall) by centrifugation at 14,000 rpm for 30 min to produce a peptide fraction amenable to LC-MS/MS. The peptide fraction (10 μL) was analysed on the QStar Elite mass spectrometer.

Q-TOF MS

Samples were chromatographically separated on a Shimadzu nano HPLC system (Shimadzu Scientific, Rydalmere, Australia) using a Vydac MS C18 300 Å, column (150 mm×0.3 mm) with a particle size of 5 μm (Grace Davison, Deerfield, USA) using a linear gradient of 2-42% solvent B over 20 min at a flow rate of 3 μL/min. The mobile phases consisted of solvent A (0.1% formic acid) and solvent B (0.1% formic acid/90% acetonitrile/10% water). A QStar Elite QqTOF mass spectrometer (Applied Biosystems) was used in standard MS/MS data-dependent acquisition mode with a nano-electrospray ionization source. Survey MS spectra were collected (m/z 400-1800) for 1 s followed by three MS/MS measurements on the most intense parent ions (10 counts/second threshold, 2+ to 5+ charge state, and m/z 100-1600 mass range for MS/MS), using the manufacturer's 'Smart Exit'. Parent ions previously targeted were excluded from repetitive MS/MS acquisition for 30 seconds (mass tolerance of 100 mDa).

Linear Ion Trap (Triple Quadrupole) MS

Reduced and alkylated tryptic peptides were analyzed on an Applied Biosystems 4000 QTRAP mass spectrometer (Applied Biosystems, Framingham, Mass., USA) equipped with a TurboV ionization source operated in positive ion mode. Samples were chromatographically separated on a Shimadzu Nexera UHPLC (Shimadzu) using a Phenomenex Kinetex C18 (2.1 mm×10 cm) column with a linear gradient of 5-45% acetonitrile (ACN) over 15 min with a flow rate of 400 μL/min. The eluent from the HPLC was directly coupled to the mass spectrometer. Data were acquired and processed using Analyst 1.5 Software™. Information Dependent Acquisition (IDA) analyses were performed using an enhanced MS (EMS) scan over the mass range 350-1500 as the survey scan and triggered the acquisition of tandem mass spectra. The top two ions of charge state 2-5 that exceeded a defined threshold value (100,000 counts) were selected and first subjected to an enhanced resolution (ER) scan prior to acquiring an enhanced product scan (EPI) over the mass range 125-1600.

Analysis of Mass Spectra and Database Searching

ProteinPilot™ 4.0 software (Applied Biosystems) with the Paragon Algorithm was used for the identification of proteins. Tandem mass spectrometry data was searched against in silico tryptic or chymotryptic digests of Triticeae proteins of the Uniprot (version 2011/05) and NCBI (version 2011/05) databases. All search parameters were defined as iodoacetamide modified with cysteine alkylation, with either trypsin or chymotrypsin as the digestion enzyme. Modifications were set to the "generic workup" and "biological" modification sets provided with this software package, which consisted of 126 possible modifications, for example, acetylation, methylation and phosphorylation. The generic workup modifications set contains 51 potential modifications that may occur as a result of sample handling, for example, oxidation, dehydration and deamidation. Peptides with one missed cleavage were included in the analysis.

Construction and Application of a Custom-Built Cereal Database

A non-redundant custom cereal seed storage protein database was constructed by including all reported protein sequences from nucleotide entries in NCBI, TIGR Gene Indices, or TIGR Plant Transcript Assemblies belonging to Triticum, Hordeum, Avena, Secale and Triticosecale species. The nucleotide sequences, for the above species, were translated in six frames, trimmed to keep only the longest open reading frame. The resulting protein sequence set was then made non-redundant. Only sequences with 100% match from start to finish were collapsed together, to maintain all variations. Lastly, these files were filtered to retain only entries containing the words gluten, gliadin, glutenin, hordein, avenin or secalin. Tandem mass spectrometry data was searched against the custom cereal database.

Protein Alignment and Identification of Prototypic Peptides

All known hordein proteins in the Uniprot database and predicted hordein proteins in the TIGR database were aligned. Within each family (B, C, D or γ), peptides that were common were selected as representative of the family. MRM transitions were determined for each peptide where the precursor ion (Q1) m/z was based on the size and expected charge and the fragment ion (Q3) m/z values were predicted using known fragmentation patterns and/or the data collected in the characterization workflows. Up to six transitions were used in the preliminary analyses and the MRM transitions were refined and the top two MRM transitions were selected per peptide for use in the final method, wherein the most intense MRM transition was used as a quantifier and the second most intense transition was used as a qualifier.

MRM Mass Spectrometry

MRM experiments were used for quantification of the hordein-derived tryptic peptides. For both IDA- and MRM-triggered MS/MS experiments, the scan speed was set to 1000 Da/s and peptides were fragmented in the collision cell with nitrogen gas using rolling collision energy dependent on the size and charge of the precursor ion. Quantification of hordein peptides was achieved using scheduled MRM scanning experiments using a 120 s detection window for each MRM transition and a is cycle time. The first quadrupole was used to select the mass-to-charge ratio (m/z) of the analyte, the so-called precursor ion. The precursor ion was then transmitted to the collision cell (the second quadrupole). Collision-induced dissociation (CID) occurs resulting in the production of fragment ions that were transmitted to the third quadrupole. A second stage of mass selection occurs specifically targeting the m/z values of the known fragment ions. The two stages of mass selection are known as Q1 and Q3 referring to the quadrupole in which they occur. The Q1 to Q3 transition is thus known as the MRM transition and is highly specific and selective for the analyte of choice.

Relative Quantification of Hordeins

The relative quantification of each hordein was performed by integrating the peak area of the most intense MRM transition for each peptide. The average peak area was determined by taking the mean of two replicate injections (on different days) from bottles A and B (representing the biological replicates). The results are presented as the percentage of each hordein protein relative to the average hordein content of all gluten-containing beers.

Example 2. Characterization of Hordeins in Barley Flour

Hordeins extracted from barley flour (wild-type cv Sloop) by solubilisation into an alcohol solution were purified by FPLC as described in Example 1. The purified hordein fractions were reduced, alkylated and subjected to either trypsin or chymotrypsin digestion. Following enzymatic digestion, the sub-10 kDa fraction was analyzed by LC-MS/MS to identify the hordeins present in the purified prolamin fraction from flour to provide the complete suite of hordein proteins that might be expected to be found in beer brewed from this flour. Using a 1% false discovery rate (FDR), a total of 144 proteins were identified after trypsin digestion and a total of 55 proteins were identified after chymotrypsin digestion.

Table 1 lists the hordein protein products detected from flour following tryptic digestion. Among the most abundant proteins detected were the previously reported B3-hordein (Accession No. P06471, Kristoffersen et al., 2000), γ-3-hordein (P80198, Fasoli et al., 2010) and the predicted γ-1-hordein (P17990, Cameron-Mills et al., 1988). Likewise, D-hordein (Uniprot: Q84LE9, Gu et al., 2003) was detected in abundance. Other proteins of lesser abundance were detected including two γ-hordeins and a B1-hordein that were not present in either the NCBI or Uniprot databases (Table 1). These proteins were identified by searching a custom-built database comprising translated cereal proteins from nucleotide entries in NCBI, TIGR Gene Indices, or TIGR Plant Transcript Assemblies. Several peptides matching to predicted γ-gliadins and glutenins (from wheat) and avenin-like protein-A (from wheat and goat-grass) were detected. The avenin-like A proteins were reported to be present in beer (Picariello et al., 2011) based on the detection of a 15 amino acid peptide (QQCCQPLAQISEQAR, SEQ ID NO: 5) resulting from tryptic digestion of a 16-17 kDa protein band isolated by SDS-PAGE. The peptide sequence matched a sequence in a single protein from barley as determined by BLASTp searching, along with an additional 13 amino acid (aa) peptide matching to the same predicted protein sequence (Uniprot: F2EGD5). An 11 aa (MVLQTLPSMCR, SEQ ID NO: 6) peptide mapping to an avenin-like A protein (Uniprot: Q2A782) from Aegilops cylindrica (jointed goatgrass) was also detected. A subsequent search of the translated EST database (TIGR) revealed a H. vulgare protein that explained the 11 aa peptide. Based on the homology between the predicted avenin-like protein-A and γ-hordein proteins, these were included in subsequent analyses.

Single peptide identifications hinted at the presence of C-hordeins within the hordein fraction, however, sequence alignment of known C-hordein proteins revealed an absence of tryptic cleavage sites within these glutamine-rich proteins. Consequently, chymotryptic digest of the hordein fraction yielded identification of C-hordeins with up to 80% sequence coverage (Table 2), highlighting the need for an alternative digestion strategy to characterize this class of hordeins.

TABLE 1

Prolamin proteins identified in FPLC purified fraction of barley flour after trypsin digestion.

| Uniprot Accession | NCBI Accession | TIGR Accession | Name | Score | Coverage | Peptides |
|---|---|---|---|---|---|---|
| — | — | BE454297 | B3-hordein *** | 57.03 | 87.1 | 52 |
| P80198 | 1708280 | TA29416_4513 | γ-hordein-3 | 38.40 | 54.0 | 32 |
| Q84LE9 | 75147012 | TA30219_4513 | D-hordein ** | 34.70 | 55.6 | 41 |
| P17990 | 123464 | — | γ-hordein-1 | 27.70 | 74.7 | 23 |
| — | — | TA30139_4513 | γ-hordein *** | 18.95 | 45.5 | 24 |
| Q40026 | 75220903 | TA29493_4513 | B1-hordein ** | 8.58 | 46.6 | 19 |

TABLE 1-continued

Prolamin proteins identified in FPLC purified fraction of barley flour after trypsin digestion.

| Uniprot Accession | NCBI Accession | TIGR Accession | Name | Score | Coverage | Peptides |
|---|---|---|---|---|---|---|
| Q4G3S1 | 122220129 | — | B3-hordein * | 5.55 | 15.7 | 10 |
| P06472 | 123460 | — | C-hordein * | 4.56 | 23.9 | 4 |
| C7FB16 | 255348358 | — | B-hordein ** | 4.00 | 22.4 | 22 |
| Q2A782 | 122238432 | — | Avenin-like A * | 4.00 | 14.4 | 2 |
| F2XAR6 | 327365751 | — | γ-gliadin ** | 3.89 | 9.5 | 3 |
| — | — | TA29452_4513 | B1-hordein *** | 3.87 | 52.2 | 18 |
| P17991 | 123461 | — | C-hordein * | 3.87 | 95.8 | 3 |
| — | — | AJ433315 | γ-hordein *** | 3.53 | 99.1 | 19 |
| P06471 | 123459 | HVB3HORD | B3-hordein | 2.00 | 73.1 | 42 |
| B9VSH7 | 222538169 | — | D-hordein (similar to HMW glutenin) ** | 2.00 | 16.1 | 9 |
| Q3YAF9 | 122217636 | — | B-hordein ** | 2.00 | 21.7 | 8 |
| B5A818 | — | — | B-hordein (similar to LMW glutenin) ** | 2.00 | 27.2 | 7 |
| D4HNB5 | — | — | B-hordein (similar to LMW glutenin) ** | 2.00 | 13.2 | 4 |
| Q8S3W0 | 75159492 | — | D-hordein (similar to HMW glutenin) ** | 2.00 | 5.0 | 6 |
| F2EGD5 | 326501830 | — | Avenin-like A * | 2.00 | 16.2 | 2 |

Accession numbers for each protein are listed:
* indicates protein identification supporting annotated transcript evidence (Uniprot);
** indicates protein identification supporting genome-derived predicted protein (Uniprot);
*** indicates novel protein identified in database search against unannotated TIGR ESTs.

TABLE 2

Prolamin proteins identified in FPLC purified fraction of barley flour after chymotrypsin digestion.

| Uniprot Accession | NCBI Accession | TIGR Accession | Name | Score | Coverage | Peptides |
|---|---|---|---|---|---|---|
| P06471 | 123459 | HVB3HORD | B3-hordein | 85.95 | 86.4 | 51 |
| Q84LE9 | 75147012 | TA30219_4513 | D-hordein ** | 54.28 | 36.2 | 28 |
| Q41210 | 75102504 | — | C-hordein ** | 50.10 | 88.7 | 44 |
| P80198 | 1708280 | TA29416_4513 | γ-hordein-3 | 36.38 | 69.9 | 19 |
| Q40053 | 19001 | — | C-hordein (Hor1-17) ** | 28.93 | 83.9 | 41 |
| — | — | TA30139_4153 | γ-hordein *** | 21.31 | 59.2 | 11 |
| P06470 | 123458 | — | B1-hordein | 10.13 | 25.1 | 14 |
| Q0PIV6 | 110832715 | — | B-hordein ** | 10.00 | 62.4 | 22 |
| P17990 | 123464 | — | γ-hordein-1 * | 8.00 | 50.9 | 7 |
| P17992 | 123462 | — | C-hordein * | 6.02 | 65.1 | 7 |
| Q571R2 | 75271341 | — | C-hordein (similar to σ-gliadin) * | 4.00 | 61.3 | 3 |
| — | — | TA29452_4513 | B1-hordein *** | 2.13 | 59.4 | 14 |
| C7FB16 | 255348358 | — | B-hordein ** | 2.02 | 61.9 | 15 |
| — | — | TA28105_4153 | Similar to C-hordein *** | 2.01 | 53.4 | 1 |
| — | — | BG416634_F0 | B3-hordein *** | 2.00 | 81.5 | 32 |
| | | BI950745_F1 | B3-hordein *** | 2.00 | 33.6 | 15 |
| — | — | TA29459_4513 | B-hordein (similar to GBSS Wx-TmA) *** | 2.00 | 60.9 | 12 |
| Q5PU42 | 56126405 | — | B-hordein (similar to LMW glutenin) ** | 2.00 | 22.6 | 6 |
| Q4G3S5 | 57118089 | — | B3-hordein * | 2.00 | 24.0 | 6 |

Accession numbers for each protein are listed:
* indicates protein identification supporting annotated transcript evidence (Uniprot);
** indicates protein identification supporting genome-derived predicted protein (Uniprot);
*** indicates novel protein identified in database search against unannotated TIGR ESTs.

Example 3. Characterization of Hordeins in Wort and Beer

Analysis of wort, the liquid extracted from the mashing process during brewing, and beer were then conducted and a similar suite of prolamins were identified (Table 3). A total of 27 proteins were identified in wort and 79 in beer, with the most abundant proteins being non-specific lipid transfer protein 1 (LTP1) and the α-amylase trypsin inhibitors (CMd, CMb, CMa). The gluten proteins identified in wort included the avenin-like A protein (18 peptides), γ-hordein-3 (10 peptides) and D-hordein (4 peptides) that were previously observed in the enriched hordein fraction. It was interesting to note, however, that >50% of the peptides were semi-tryptic (cleaved at one end at a site other than Lys/Arg), suggesting that significant degradation of the proteins had occurred during the brewing process. The avenin-like A protein (GenBank Accession No. BE195337) identified from the EST database search was detected with >60% sequence coverage (12 peptides) increasing the confidence of this protein identification.

C-hordein proteins were noticeably absent in beer, but to ensure this was not a false positive owing to the low number of tryptic sites, a chymotryptic digest was performed which affirmed the absence of C-hordeins in beer (Table 3). The absence of C-hordeins was presumably related to their insolubility in water. C-hordeins consist of multiple octapeptide repeats with a consensus sequence of PQQPFPQQ (SEQ ID NO: 7) rendering them highly insoluble. Many of the C-hordein degradation products are identified in wort but did not survive the brewing and filtration steps leading to the production of beer.

In order to characterize peptide fragments, the wort and beer were passed through a 10 kDa molecular weight cut-off filter and analyzed without enzymatic digestion. 1D-PAGE analysis revealed that the filtration step was efficient in removing proteins from beer. MS analysis revealed the presence of several truncated or degraded hordein products. Table 4 lists the peptide fragments identified. In addition to hordein peptides, peptides derived from a large number of barley proteins including serpin-Z4, non-specific lipid transfer protein 1, α-amylase, β-amylase, hordoindoles (B1, B2) and GAPDH were identified in wort and beer (listed Table 4 and Supplementary Table 2 of Colgrave et al., 2012). Of interest, was the large number of C-hordein fragments observed in wort with only trace levels of C-hordein peptides detected in beer.

The characterization of beer in the absence of enzymatic digestion clearly demonstrates that in addition to intact hordeins, a large number of partially degraded hordein fragments are present and these may also contribute to coeliac toxicity. Many of these peptide fragments contained runs of Gln and Pro that may elicit an immunological response in coeliacs. Examples of potential immunogenic peptides detected are FVQPQQQPFPLQPHQP (avenin-like A; GenBank: TA31086, SEQ ID NO: 8), YPEQPQQPFPWQQPT (γ-1-hordein; P17990, SEQ ID NO: 9), LERPQQLFPQWQPLPQQPP (γ-3-hordein; P80198, SEQ ID NO: 10) and LIIPQQPQQPFPLQPHQP (C-hordein; P17991, SEQ ID NO: 11), where the underlined sequence bears high homology with immunogenic peptides reported previously (Tye-Din et al., 2010; Kahlenberg et al., 2006).

TABLE 3

Prolamin proteins identified in wort and beer.

| Uniprot Accession | NCBI Accession | TIGR Accession | Name | Score | Coverage | Peptides |
|---|---|---|---|---|---|---|
| Prolamins identified in wort (trypsin digestion) | | | | | | |
| F2EGD5 | 326501830 | — | Avenin-like A * | 29.33 | 41.6 | 18 |
| P80198 | 1708280 | TA29416_4513 | γ-hordein-3 | 18.05 | 33.2 | 10 |
| — | — | BE195337 | Avenin-like A *** | 14.00 | 47.0 | 9 |
| Q84LE9 | 75147012 | TA30219_4513 | D-hordein ** | 8.08 | 8.9 | 4 |
| Prolamins identified in beer (trypsin digestion) | | | | | | |
| P80198 | 1708280 | TA29416_4513 | γ-hordein-3 | 55.62 | 53.6 | 33 |
| Q84LE9 | 75147012 | TA30219_4513 | D-hordein ** | 30.16 | 22.2 | 23 |
| P06471 | 18914 | HVB3HORD | B3-hordein | 17.81 | 24.6 | 9 |
| P17990 | 123464 | — | γ-hordein-1 * | 16.98 | 31.9 | 9 |
| — | — | BE195337 | Avenin-like A *** | 15.66 | 64.6 | 12 |
| F2EGD5 | 326501830 | — | Avenin-like A * | 8.06 | 35.3 | 8 |
| Q4G3S5 | 57118089 | — | B3-hordein * | 5.48 | 12.6 | 6 |
| Q40026 | 75220903 | TA29493_4513 | B1-hordein ** | 2.01 | 8.6 | 7 |
| Q94IL5 | 75250230 | — | D-hordein (similar to HMW glutenin) ** | 2.00 | 4.6 | 8 |
| Prolamins identified in beer (chymotryptic digestion) | | | | | | |
| P80198 | 1708280 | TA29416_4513 | γ-hordein-3 | 19.75 | 56.1 | 12 |
| Q40022 | 829269 | — | B1-hordein * | 13.80 | 51.4 | 9 |
| Q84LE9 | 75147012 | TA30219_4513 | D-hordein ** | 12.00 | 26.0 | 6 |
| P17990 | 123464 | — | γ-hordein-1 * | 5.59 | 22.5 | 3 |
| F5A7G6 | — | — | B-hordein (similar to LMW glutenin) ** | 2.00 | 23.2 | 5 |
| Q6EEZ0 | — | — | γ-hordein-3 ** | 2.00 | 25.8 | 2 |

Accession numbers for each protein are listed:

* indicates protein identification supporting annotated transcript evidence (Uniprot);

** indicates protein identification supporting genome-derived predicted protein (Uniprot);

*** indicates novel protein identified in database search against unannotated TIGR ESTs.

TABLE 4

Peptides derived from hordein proteins detected in the sub-10 kDa fraction of beer. Epitopes in bold show high sequence homology with the gluten epitopes recognised by the Mendez R4 MAb raised against rye prolamins (QQPFP (SEQ ID NO: 12), QQQFP (SEQ ID NO: 13), LQPFP (SEQ ID NO: 14), QLPFP (SEQ ID NO: 15))[a]. These peptides may elicit an immune response in CD patients.

| Name[b] | Conf | Peptide | m/z | Mass | Δm (ppm) |
|---|---|---|---|---|---|
| D-hordein (Q84LE9**) | 99 | RVVDQQLVGQLPWSTG (SEQ ID NO: 16) | 891.99 | 1781.97 | 13.41 |
| | 99 | VVDQQLVGQLPWSTGL (SEQ ID NO: 17) | 870.45 | 1738.89 | 19.72 |
| | 99 | VVDQQLVGQLPWSTG (SEQ ID NO: 18) | 813.93 | 1625.85 | 5.17 |
| | 99 | VVDQQLVGQLPW (SEQ ID NO: 19) | 691.38 | 1380.74 | 2.46 |
| | 99 | QLVGQLPWSTGL (SEQ ID NO: 20) | 649.85 | 1297.68 | 16.25 |
| | 99 | QLVGQLPWSTG (SEQ ID NO: 21) | 593.30 | 1184.59 | 22.03 |
| | 99 | LVGQLPWSTGLQM (SEQ ID NO: 22) | 715.37 | 1428.73 | 12.46 |
| | 99 | LVGQLPWSTGL (SEQ ID NO: 23) | 585.83 | 1169.65 | 5.55 |
| | 99 | LVGQLPWSTG (SEQ ID NO: 24) | 529.28 | 1056.54 | 14.86 |
| | 99 | VGQLPWSTGLQM (SEQ ID NO: 25) | 658.83 | 1315.64 | 14.06 |
| | 99 | VGQLPWSTGL (SEQ ID NO: 26) | 529.28 | 1056.54 | 16.75 |
| | 99 | (p)QLAAQLPAMCRLEGS[HexNAc] (SEQ ID NO: 27) | 887.41 | 1772.80 | 22.05 |
| | 99 | VVRQYEQQTEVPSKGGSFYPGGTAPP (SEQ ID NO: 28) | 927.12 | 2778.35 | 5.79 |
| γ-3-hordein (P80198) | 99 | FVLPQQQAQFKVVGS (SEQ ID NO: 29) | 838.46 | 1674.90 | 4.24 |
| | 99 | FVLPQQQAQF (SEQ ID NO: 30) | 603.31 | 1204.61 | 12.54 |
| | 99 | AIVMQQQVQQQVGHGF (SEQ ID NO: 31) | 899.43 | 1796.85 | 26.60 |
| | 99 | LERP**QQLFP**QWQPLPQQPP (SEQ ID NO: 32) | 776.41 | 2326.19 | 12.21 |
| | 99 | LFPQWQPLPQQPP (SEQ ID NO: 33) | 788.41 | 1574.82 | 6.03 |
| | 99 | LQQLGQGMPIQL (SEQ ID NO: 34) | 663.85 | 1325.69 | 16.98 |
| | 95 | VVGSLVIQT (SEQ ID NO: 35) | 458.27 | 914.53 | 9.84 |
| γ-3-hordein (P179999*) | 99 | LQQP**QHQFP**QPTQQFPQRPn (SEQ ID NO: 36) | 777.39 | 2329.15 | 8.16 |
| | 99 | YPEQP**QQPFP**WQQPT (SEQ ID NO: 37) | 935.93 | 1869.84 | 16.15 |
| | 99 | GVVQPQQLAQME (SEQ ID NO: 38) | 664.31 | 1326.61 | 41.08 |
| | 99 | [p]QP**QHQFP**QPTQQFPQRP (SEQ ID NO: 39) | 691.33 | 2070.98 | 9.90 |

TABLE 4-continued

Peptides derived from hordein proteins detected in the sub-10 kDa fraction of beer. Epitopes in bold show high sequence homology with the gluten epitopes recognised by the Mendez R4 MAb raised against rye prolamins (QQPFP (SEQ ID NO: 12), QQQFP (SEQ ID NO: 13), LQPFP (SEQ ID NO: 14), QLPFP (SEQ ID NO: 15))[a]. These peptides may elicit an immune response in CD patients.

| Name[b] | Conf | Peptide | m/z | Mass | Δm (ppm) |
|---|---|---|---|---|---|
| Avenin-like A (BE195337***) | 99 | FVQP**QQQVP**VEITR (SEQ ID NO: 40) | 834.94 | 1667.87 | 19.61 |
| | 99 | FVQP**QQQVP**VEI (SEQ ID NO: 41) | 706.37 | 1410.72 | 18.78 |
| C-hordein (P17991*) | 98.2 | LIIPQQP**QQPFP**LQPHQP (SEQ ID NO: 42) | 1053.59 | 2105.17 | 14.82 |
| | 99 | IIPQQP**QQPF**PLQPHQP (SEQ ID NO: 43) | 997.05 | 1992.08 | 13.40 |
| B3-hordein (P06471) | 98.4 | VQVQIPFVHPSI (SEQ ID NO: 44) | 682.38 | 1362.74 | 16.22 |
| Avenin-like A (F2EGD5*) | 99 | SFGQP**QQQVP**VEVMR (SEQ ID NO: 45) | 865.43 | 1728.84 | 13.0 |
| C-hordein (Q40053*) | 95.8 | IIP**QQPFP**LQ**PQPFP**QQP**QQPLP**QPQQP (SEQ ID NO: 46) | 1081.25 | 3240.73 | 11.08 |
| C-hordein (TA28105***) | 96.4 | IPLQPQ[**Dea**]**QPFP**QQPP (SEQ ID NO: 47) | 808.40 | 1614.79 | 30.53 |

[a]Kahlenberg et al. (2006).
[b]Accession numbers for each protein are listed: * indicates protein identification supporting annotated transcript evidence (Uniprot);  indicates protein identification supporting genome-derived predicted protein (Uniprot); * indicates novel protein identified in database search against unannotated TIGR ESTs.

Example 4. Relative Quantitation of Hordeins in Beer by MRM Mass Spectrometry The proteomic characterization of purified hordeins and beer in Examples 2 and 3 enabled the elucidation of the major hordein proteins present in barley. Multiple reaction monitoring (MRM) was identified as a useful tool for the quantitation of peptides and proteins. In this method, following tryptic digestion of the proteins, proteolytic fragments were chromatographically separated by HPLC and analysed by MRM mass spectrometry. The first quadrupole (Q1) selected the first peptide m/z value (precursor mass) and transmited this ion to the collision cell (Q2). Collision-induced dissociation resulted in the production of fragment ion series relating to the amino-acid sequence of the proteolytic fragments. Diagnostic fragment ions were then selected in the third quadrupole (Q3) and transmitted to the detector allowing quantitation of the peptides of interest. Typically three MRM transitions per peptide were used and at least two peptides per protein.

From each of the protein families, a single isoform was selected to monitor the gluten content of beers brewed from selectively-bred barley lines (see below). Multiple tryptic peptides (≥2 peptides/protein) were selected for development of a quantitative assay. Where these peptides had previously been detected in the discovery experiments, the peptide m/z and fragment ion information was used to determine the MRM transition to be used. A number of peptides that were not initially identified were included in the MRM assay so that a minimum of two peptides per protein were used. In these instances, the retention times were not known and the MRM transitions could not be scheduled in the first pass experiments. The peptide retention times were determined and subsequent experiments used scheduled MRM transitions.

Beer derived from a single elite Australian malting barley ("Sloop") was used for the development and refinement of the MRM method as it contained the full complement of hordein proteins, whereas the barley variants (Risø 56 and Risø 1508) were expected to be low in, or devoid of, B- and C-hordeins. When beers brewed from samples of wild-type and two hordein mutant barley grains (Risø 56 and Risø 1508) were analysed using MRM analysis, the eight selected peptides (three MRM transitions per peptide) were all clearly observed for wild-type barley beer. The Risø 56 beer showed an approximate three-fold decrease in the amount of the D-hordein peptides and the B-hordein peptides were noticeably absent. The Risø 1508 beer showed a further decrease in the amount of each peptide measured, but a trace amount of avenin-like A protein was observed.

The reproducibility of the analytical method was assessed by examining the single cultivar barley beer ("Sloop"). Firstly, the beer was subjected to multiple freeze-thaw cycles (either 1, 10, 20 or 50 cycles) and no significant change (co-efficient of variation, CV, of <15%) was observed in the peak area for each of the monitored MRM transitions even after 50 cycles. Secondly, the digestion efficiency was examined by six replicate digestions yielding a CV of <15%. The analytical reproducibility was assessed by performing four replicate injections of each digest with a CV of <15%. Finally, the variation in hordein content between two different bottles of beer was assessed and found to be <10%.

Analysis of Commercial Beers

Further validation of the MRM method of quantifying hordeins in beer was provided by analyzing the gluten content of a selection of 60 commercial beers, including labeled low gluten and gluten-free beers. Duplicate samples from separate bottles were treated by reduction, alkylation and digestion (Example 1) and were analyzed by MRM mass spectrometry. FIG. 2 shows the relative quantitation of the avenin-like A proteins (A), B-hordeins (B, C), D-hordeins (D) and γ-hordeins (E) in the commercial beers relative to Sloop. Relative to the average values for the non-gluten-free beers, the commercial beers were observed to vary in the type (hordein families present) and the amount (between 1-380% cf. average for any given hordein protein). Eight of the beers (Nos. 17, 47, 49, 50, 51, 52, 58 and 60) were labeled as gluten-free as they were brewed from sorghum malt, teff, rice, millet or maize. These cereals lack the gluten proteins present in barley and wheat. The MRM assay confirmed that they were devoid of the hordein proteins and hordein-related protein (avenin-like A) targeted.

Beers 17 and 50-52 were sorghum-based, beer 47 did not specify what it is made from, beer 49 was millet-based, beer 58 was brewed from sorghum malt, teff and rice and beer 60 was a non-cereal derived beer. In the examination of two beers (57 and 59) that have been classified as low-gluten (<10 ppm), the relative hordein content was not dissimilar to the average hordein content across the range of beers tested. Beer 57 showed low avenin-like A protein levels (~50% cf. average), but surprisingly showed significant levels of peptides derived from the B1- (>300% cf. average), D- (~105%) and γ3-hordeins (~62%). Beer 59, showed low, but significant levels of B1-, D- and γ-hordeins (55%, 42% and 92% respectively) and equivalent levels of the avenin-like A protein to those observed in the gluten-containing beers.

Conclusions

Beers made from barley contained gluten derived from the grain used in the brewing process. The gluten level in beer may be measured using ELISA, however, there are many limitations associated with accurate measurement of hordeins using current ELISA technology. In the Examples above, a mass spectrometric assay was developed to characterize the complete suite of hordeins in purified hordein preparations, wort and beer and to perform relative quantitation of the most abundant hordein proteins. The assay using mass spectrometry was robust and sensitive for the measurement of hordein (gluten) in flour, wort and beer and could readily be applied to malt.

Example 5. Identification of a Null Mutation in the Hor3 Gene of Barley

The barley D-hordein polypeptide of 105 kDa is encoded by the Hor3 gene on the long arm of chromosome 1H (Gu et al., 2003). A wild-race of barley designated Ethiopian R118 was identified as not accumulating D-hordeins (Brennan et al., 1998) and was obtained from a publicly available germplasm collection at The John Innes Centre Public Collections (Accession No. 3771). This line was a wild race of barley, highly unsuited for commercial production of grain.

Grains of Ethiopia R118 were sown in the greenhouse. The resultant plants were observed to be segregating for the 2-row and 6-row phenotypes and for black, pigmented seeds and green seeds. A two-row line which produced green seeds was selected and crossed to cv Sloop. F2 half-seeds that were negative for production of D-hordein were selected. Plants of this line were back-crossed to the wild-type Sloop and an F2 plant which was null for D-hordein was again selected. This plant was backcrossed to Sloop and a progeny plant backcrossed again to produce a $BC_2$ line which was negative for D-hordein production in a genetic background which had about 87.5% of the genome of Sloop.

The gene encoding D-hordein was amplified from genomic DNA isolated from each of the Sloop $BC_2$, D-hordein negative plants derived from Ethiopia R118 and the wild-type Sloop. This was by PCR with standard conditions and generated a series of 3 overlapping fragments. The primer pairs used in the amplifications were:

```
Fragment 1
                                        (SEQ ID NO: 60)
5' Dhor1        GACACATATTCTGCCAAAACCCC
and
                                        (SEQ ID NO: 61)
3' Dhor3        ACGAGGGCGACGATTACCGC

Fragment 2
                                        (SEQ ID NO: 62)
5' Dhor1b       GAGATCAATTCATTGACAGTCCACC,
and
                                        (SEQ ID NO: 63)
3' Dhor1        CTTGTCCTGACTGCTGCGGAGAAA

Fragment 3
                                        (SEQ ID NO: 64)
5'Dhor2         GCAACAAGGACACTACCCAAGTATG,
and
                                        (SEQ ID NO: 65)
3' Dhor2        GCTGACAATGAGCTGAGACATGTAG
```

The amplification products were purified and the nucleotide sequence of each was determined. The assembled sequence from Sloop was 2838 bp long (SEQ ID NO: 72) and the sequence derived from Ethiopia R118 was 2724 bp long (SEQ ID NO: 73). The predicted ATG translation start codon for both proteins was at position 398-400 of the respective sequences. For Sloop, the termination codon was at nucleotide position 2641-2643, encoding a protein of 747 amino acid residues. Analysis of the sequence from Ethiopia R118 revealed that when compared to Sloop there was a C to G change at position 848 (position 450 relative to the start codon) that introduced an in-frame TAG stop codon into the Hor3 gene that resulted in truncation of the polypeptide at position 150 in the protein (FIG. 3). This truncated the D-hordein polypeptide before the proline and glutamine rich domain that contains epitopes identified as immunogenic to coeliacs.

This nucleotide substitution abolished a KpnI site that was present in the wild-type nucleotide sequence in cultivar Sloop and allowed the development of a co-dominant CAPS marker. For this purpose, a DNA fragment of 272 bp was amplified using the primers 5' Dhor-marker (GGCAATACGAGCAGCAAAC, SEQ ID NO: 66) and 3' Dhor-marker (CCTCTGTCCTGGTTGTTGTC, SEQ ID NO: 67) (FIG. 4). The amplification products were then incubated with the restriction enzyme KpnI and electrophoresed on agarose gels. The fragment from wild-type barley Sloop was digested by KpnI to produce two fragments of 164 bp and 108 bp. In contrast, the 272 bp fragment from the D-null Ethiopia R118 was not digested. Therefore, this method clearly distinguished the wild-type and null alleles for the gene encoding D-hordein.

Example 6. Identification of a Molecular Marker for a Deletion Mutation at the Hor2 Locus of Barley The Hor2 locus on the short arm of chromosome 1H in barley comprises a family of about 20-30 genes, each encoding a B-hordein in the size range of about 36-kDa (Anderson et al., 2013). Riso 56 is a gamma-ray induced mutation which has a deletion of about 86 kb including all or nearly all of the B-hordein genes (Kreis et al., (1983). This mutation was used to generate a Hor2-lys3a double mutation as described previously by Tanner et al. (2010), expressing greatly reduced levels of total hordeins.

A molecular marker was designed and tested to detect the wild-type Hor2 locus and distinguish it from the Hor2-deleted locus, as follows using standard PCR conditions. The absence of a B1-hordein PCR band of 800 bp was diagnostic of the absence (deletion) of the Hor2 locus i.e. the presence of the mutant allele at Hor2. The primer pairs used in the amplifications were:

```
                                (SEQ ID NO: 68)
3' B1 Hor        TCGCAGGATCCTGTACAACG

                                (SEQ ID NO: 69)
5'B1 Hor         CAACAATGAAGACCTTCCTC
```

A control PCR reaction which produced a characteristic PCR band at 450 bp was also carried out on each DNA sample, indicating the presence of the gamma-hordein locus and ensured the quality of the sample DNA was sufficient for the Hor2 reaction, using primer pairs:

```
                                (SEQ ID NO: 70)
5' gamma Hor 3   CGAGAAGGTACCATTACTCCAG

                                (SEQ ID NO: 71)
3' gamma 3 full  AGTAACAATGAAGGTCCATCG
```

Example 7. Generation of a Triple Null Barley Mutant

F5 plants of the Hor2-lys3a double mutant barley line identified as G1* in WO2009/021285 were grown in the glasshouse to produce F6 progeny. F6 plants were then grown in the field to produce F7 progeny. To combine the Hor2-lys3a mutations with the Hor3 null mutation, plants of the F7 generation were crossed with the D-hordein negative $BC_2$ plants derived from Ethiopia R118 (Example 5) and the F1 progeny selfed to produce F2 seeds. F2 seeds were cut in half and the germ-half germinated and the seedlings screened by B- and D-hordein PCR as in Examples 5 and 6 and for gamma-hordein. The remaining half of each seed comprising the endosperm was ground in a solution containing 8M urea, 1% DTT and the extracted proteins separated by SDS-PAGE. The absence of characteristic protein bands at approximately 50 kDa indicating the absence of the C-hor proteins. Three hordein triple-nulls, designated T1, T2, and T3 were identified from about 300 F2 seeds. The expected frequency for the combination of three recessive mutations, each in the homozygous state, by Mendelian genetics was 1/64, presuming that the Hor2 (B-hordeins) and Hor3 (D-hordeins) loci are separated far enough on chromosome 1H to recombine readily.

The three plants which were homozygous for each of the three mutations (Hor2-lys3a-Hor2) designated T1, T2 and T3 were maintained and propagated through up to three generations of single-seed descent, selecting the 12 heaviest seeds in each generation. Average seed weights of F3 seeds from these lines were: T1, 38.2 mg; T2, 37.0 mg; T3, 39 mg. Seed yield per line (grams of seed per 20 heads) and plant heights were measured. Plants which produced poorly filled heads were discarded. Two F4 lines were selected: T2-4-8 and T2-6-A5 and further trialed in the field. Of these, T2-4-8 was selected as having slightly better grain yield and designated as barley ULG3.0.

An important phenotype for barley grain, related to grain size and shape and an indicator of grain yield, is the percentage of grains which do not pass through sieves with a mesh size of 2.8, 2.5, 2.2 and 2.0 mm, in particular the 2.8 mm sieve. Smaller grain makes the processing and malting less efficient relative to wild-type barley. This phenotype is referred to as "2.8 mm screenings" and is indicated as the percentage of grains that do not pass through the particular sieve. For wild-type cultivars such as Sloop, the 2.8 mm screening parameter is typically 95-98%. For hordein-deficient lines such as the Hor2-lys3a double mutant (ULG2.0), the 2.8 mm screening parameter was generally about 53%. Sometimes, depending on the growth conditions e.g. drought, it was less than 10% and the majority of grains could pass through the 2.5 mm sieve. For ULG3.0, the 2.8 mm screening parameter was about 54%. Average weights (mg) of field grown grains were: Sloop, 53.6+/−0.9, ULG2.0, 33.5+/−0.4; ULG3.0, 39.1+/−0.3. ULG3.0 therefore provided 69% of the grain yield compared to ULG2.0 at 50% relative to the wild-type Sloop (100%). ULG3.0 therefore represented a substantial improvement in grain yield compared to the ULG2.0 line. However, the 2.8 mm screening parameter remained a problem for barley ULG3.0.

Example 8. Generation of a Further Triple Null Barley Mutants with Increased Yield Although the ULG3.0 barley line produced increased grain yield compared to ULG2.0, it was still desirable to increase that further. Therefore, plants of ULG3.0 were crossed with plants of wild-type cultivars Sloop, Baudin and Yagan, and with plants of hordein triple null lines identified containing 50% of each parent germplasm. These hordein triple-null lines were intercrossed, and also crossed to wild-type cultivars Hindmarsh and Commander. Progeny comprising all three null mutations were backcrossed twice to plants of Sloop, Baudin, Hindmarsh and Commander and more homozygous lines produced by single-seed descent. One resultant line of the many that were produced was selected and designated as barley ULG3.1.

From the intercrosses with the Sloop, Yagan and Baudin plants, a second round of intercrosses was performed to combine the genetic backgrounds of all three parent cultivars starting with plants which each comprised the triple null mutations. From the intercrossed F1 plants, all of the progeny were expected to comprise all three mutations. About 1000 F2 seed per pedigree were planted in rows in the field, and F2 plants selected which were relatively shorter and produced F3 seed that were larger, with well-filled heads. Both early and late maturing plants were selected. In a following generation grown in the field, lines were selected which additionally exhibited relatively high grain amylase, relatively high harvest index and head length, optimal height (semi-dwarf), lack of lodging and disease resistance to powdery mildew. From the 1500 families, about 20 of the best were selected. Data for the 20 best lines is provided in Table 5. Individual seed weights (kernel weight) were improved beyond that of ULG 3.0 of 41.8 mg/seed with the highest seed weight of 48.4 mg/seed being observed for line P12072-2. This improvement in seed size was accompanied by increased harvest index, a measure of efficiency of seed formation, above 40% with the highest harvest index of 46.5% being measured in line P12124-1. Most importantly, the percentage 2.8 mm screenings also improved from 53.5% for ULG3.0 to over 80% with a high of 97.3% for line P12140-1.

One selected line was fixed by a single-seed generation to produce plants that were homozygous for the three null alleles at Hor2-lys3a-Hor3 and designated ULG3.2. The 2.8 mm screening parameter for ULG3.2 was in the range of 80-93% in several replications when grown in the field compared to about 97% for Sloop, 85% for Hindmarsh, 96% for wild-type cultivar Oxford, and 98% for Maratime.

Average seed weights and thicknesses were: ULG2.0, 33.4 mg, 2.4 mm; ULG3.0, 41.8 mg, 2.5 mm; ULG3.2, 47.2 mg, 2.8 mm.

TABLE 5

Second selection of ULG 3.2 lines June 2012.

| Plant ID No | Mean tiller | Mean head | Harvest index (%) | No of Tillers | Kernel weight | % 2.8 mm Screening |
|---|---|---|---|---|---|---|
| P12072-2 | 84.7 | 8.3 | 39.0% | 9 | 48.4 | 88.3 |
| P12132-1 | 83.0 | 8.2 | 43.9% | 5 | 47.5 | 92.7 |
| P12048-1 | 75.0 | 7.0 | 39.4% | 8 | 47.2 | 86.7 |
| P12122-2 | 74.3 | 6.7 | 35.0% | 5 | 47.2 | 96.5 |
| P12049-1 | 70.0 | 6.3 | 38.7% | 12 | 46.5 | 93.6 |
| P12125-1 | 78.0 | 7.7 | 42.0% | 10 | 46.2 | 95.3 |
| P12140-1 | 105.7 | 9.0 | 32.4% | 15 | 45.9 | 97.3 |
| P12055-2 | 57.0 | 5.8 | 36.3% | 5 | 45.7 | 91.9 |
| P12088-2 | 72.7 | 6.3 | 42.6% | 8 | 45.4 | 90.7 |
| P12125-2 | 71.7 | 5.3 | 45.3% | 8 | 45.0 | 95.0 |
| P12043-2 | 86.7 | 9.0 | 29.5% | 12 | 44.7 | 85.4 |
| P12050-1 | 64.3 | 6.0 | 36.5% | 4 | 44.4 | 93.6 |
| P12148-1 | 93.3 | 7.3 | 35.0% | 14 | 44.2 | 90.0 |
| P12149-1 | 103.3 | 8.0 | 34.7% | 15 | 44.0 | 91.2 |
| P12124-1 | 79.3 | 7.3 | 46.5% | 8 | 43.7 | 96.8 |
| P12152-2 | 98.3 | 9.0 | 34.8% | 9 | 43.5 | 91.5 |
| P12049-3 | 76.3 | 6.3 | 40.0% | 7 | 43.2 | 92.4 |
| P12100-2 | 79.3 | 6.3 | 46.5% | 15 | 43.2 | 88.3 |
| P12126-1 | 73.0 | 6.0 | 37.0% | 10 | 43.1 | 98.0 |
| P12122-1 | 64.7 | 6.0 | 45.4% | 5 | 42.8 | 90.8 |
| P12048-2 | 65.0 | 5.7 | 41.8% | 4 | 42.5 | 93.9 |
| P12148-2 | 90.3 | 6.3 | 33.3% | 7 | 42.5 | 94.9 |
| P12159-2 | 82.7 | 7.7 | 33.6% | 12 | 42.4 | 83.5 |
| P12139-1 | 113.7 | 8.3 | 33.9% | 8 | 42.2 | 88.1 |
| P12159-1 | 96.3 | 8.8 | 31.9% | 14 | 41.7 | 94.1 |
| P12139-2 | 89.3 | 7.7 | 34.4% | 5 | 41.3 | 96.8 |
| P12064-2 | 82.3 | 7.2 | 40.8% | 11 | 41.2 | 92.4 |
| P12120-2 | 75.0 | 6.8 | 39.6% | 18 | 41.0 | 84.0 |
| Selection criterion | | >4 < 10 | >35% | 5 > 20 | >40 | >80% |

Example 9. Measurement of Hordein Levels in Triple Null Barley Mutants

Determination of Hordein Content of ULG3.0 Flour by Multiple Reaction Monitoring Mass Spectrometry (MRM MS)

To measure the hordein content accurately, the MRM MS assay was used, as follows. Grains or half-grains were milled to produce flour which, as wholemeal flour, had the same composition as the entire grain. The prolamin polypeptides from 20 mg flour samples were extracted using 200 μL of a solution containing 55% (v/v) isopropanol and 2% (w/v) dithiothreitol (DTT). An aliquot of the extract, equivalent to 5 mg flour, was subjected to buffer exchange into 8M urea in 0.1 M Tris-HCl, pH 8.5, by centrifuging thrice, using a 10 kDa MW cut-off filter unit. The cysteines in the polypeptides were alkylated by addition of 100 μL of 50 mM iodoacetamide and incubation for 1 hr at room temperature. The buffer was exchanged to 100 μL of 50 mM ammonium bicarbonate, pH 8.5, and polypeptides digested with 10 μL (20 μg) of trypsin for 18 hr at 37° C. The peptides were collected by filtration through the 10 kDa filter, dried and reconstituted in 30 μL of 1% (v/v) formic acid. Peptides were separated by liquid chromatography on a Shimadzu Nexera HPLC with Phenomemenex column (Kinetex, 1.7 μm, C18, 100×2.1 mm) with a gradient from 5% B to 40% B over 10 min at a flow rate of 0.4 mL/min. Solvent A was 0.1% (v/v) aqueous formic acid, solvent B was 90% (v/v) acetonitrile containing 0.1% (v/v) formic acid. The HPLC eluate was directly coupled to the mass spectrometer and MRM analysis was performed on a 4000 QTRAP mass spectrometer targeting hordein-derived tryptic peptides. Data was analysed using Analyst v1.5 software and MultiQuant v2.0.2 software using (peak area integration).

FIG. 5 shows the data obtained for selected B-hordeins, C-hordein, D-hordein, gamma-3-hordein (G3) and gamma-1-hordein (G1). FIG. 5 presents the mean peak area for each peptide MRM transition normalized to the level in Sloop (100%), for four replicate injections from each half-grain from control barley (wild-type, cv Sloop), hordein single-null lines: Risø 56, Risø 1508 and the D-null line derived from Ethiopia R118, the hordein double-null line ULG2.0 and the triple-null lines T2-4-8 and T2-6-A5 (circled). One prototypic peptide was chosen to represent each hordein family, namely: for B-hordein, TLPTMCSVNVPLYR (SEQ ID NO: 48); for D-hordein, DVSPECRPVALSQVVR (SEQ ID NO: 49); for C-hordein, LPQKPFPVQQPF (SEQ ID NO: 50); for G3-hordein, QQCCQQLANINEQSR (SEQ ID NO: 50) and for G1-hordein, CTAIDSIVHAIFMQQGR (SEQ ID NO: 51). These peptides appear frequently and at relatively high abundance in wild-type barley, and were chosen on that basis.

It was seen that the triple-null ULG3.0 grain from line T2-4-8 and second triple-null line T2-6-A5 did not have detectable levels of B-, C-, D-, or, most surprisingly, gamma-1-hordein. That is, less than 1% of the level was observed relative to wild-type. In the same way, gamma-2-hordein was not detected in the ULG3.0 grain. There was a relatively low level of gamma-3-hordein (circled), present at a level of about 20% compared to the level of G3 in Sloop. Gamma-3 hordein is a minor hordein; the gamma-3 hordein content of Sloop is much less than 1% of the total hordein content. The single-null and double-null grains did not accumulate the appropriate hordein, e.g. RisØ56 and ULG2.0 did not accumulate B-hordeins as expected, and RisØ1508 and ULG2.0 did not accumulate C-hordeins as expected. The D-null grain exhibited wild-type levels of B- and C-hordeins but did not accumulate D-hordein.

When the analysis was repeated using several different peptide sequences, in particular the D-hordein peptide AQQLAAQLPAMCR (SEQ ID NO: 85) which is present in the wild-type D-hordein protein towards the C-terminus, well after the position of the stop codon in the B-hordein mutant, similar results were obtained (FIG. 6). The avenin-like A protein was also absent from the flour.

It was clear that grain obtained from the hordein triple nulls T2-4-8 and T2-6-A5 did not contain detectable levels of B-, C-, D-hordeins and selected gamma-1 (P17990) and gamma-2 hordeins. The observation for the gamma-1 and gamma-2 hordeins was most unexpected to the inventors, as the triple null mutant lines were not known to contain any mutations that would entirely silence the corresponding genes.

The low hordein content of the ULG3.0 grain as determined by MRM was confirmed by a two-dimensional gel electrophoresis method, as follows. Fifty μg of alcohol soluble protein from extracts of flour from each of hordein null lines T2-4-8 and T2-6-A5 as well as control barley cv Risø 56, each spiked with 1 μg of the landmark polypeptide standards BSA, soy trypsin inhibitor and horse myoglobin were stained with 0.006% (w/v) Colloidal Coomassie G250 according to Tanner et al. (2013) and compared to standard proteins of 20, 30, 40, 50, 60, 80, and kDa (M; Benchmark Protein Ladder, Invitrogen). Spots were cut out of the 2D gel and the following proteins from the control Risø 56 were identified by mass spectrometry of tryptic peptides: C-hordein, gamma-2-hordein (γ2), gamma-3-hordein (γ3) and gamma-1-hordein (γ1), The predicted positions of gamma-1-, gamma-2, and gamma-3-hordeins in the gels from the ULG3.0 grain were identified by comparison with the Risø 56 gel. Only gamma-3-hordein was observed in ULG3.0 flour, the other three polypeptides were not detected. The gamma-3 hordein concentration of each spot were measured by three methods: 1) As a percentage of all spot volumes from the 50 μg of protein: ULG3.0 average γ3 content was 13.5±1.6 ppm; 2) Relative to the spot intensity of 1 μg of BSA: ULG3.0 average γ3 content was 10.9±1.3 ppm; 3) Relative to the spot volume (intensity x area) of 1 μg of BSA: ULG3.0 average γ3 content was 3.4±0.41 ppm.

The low hordein content of the ULG3.0 grain as determined by MRM was further confirmed by an ELISA method, as follows. Twenty mg of wholemeal flour samples or the endosperm half of grains were crushed and washed thrice in 0.5 ml of MilliQ water by shaking at 30/sec for 3×30 sec in a 96 well Vibration Mill (Retsch Gmbh, Rheinische) and centrifuged at 14,000 rpm for 5 min. Prolamins in the flours were extracted into an alcoholic solution consisting of 0.5 ml of 50% (v/v) isopropanol/1% (w/v) DTT, for the control lines Sloop, Rise56, Risø1508, and for ULG2.0, the hordein triple-null lines T1, T2, and T3, and the single seed descent progeny from T2-4-8 and T2-6-A5. Protein concentrations were determined according to Bradford (1976) and 40 ng (1900 ng for the triple-null grains) of alcohol soluble protein diluted with a solution containing ELISA systems diluents with a constant excess of 0.2 mM $H_2O_2$ added to quench any DTT remaining from the initial extract. Diluted protein solutions were added to ELISA plate wells (ELISASystems, Windsor, Queensland, AUSTRALIA), washed and developed at 37° C. for 15 minutes according to the manufacturer's instructions. The amount of hordein in the control extracts was calibrated against a standard of 0-50 ng of Sloop total hordein. Hordein content of the triple-nulls was calibrated against a standard of 0-5 ng of ULG2.0 total hordein. The Sloop and ULG2.0 hordeins were prepared as described by Tanner et al. (2010).

By the ELISA method, the total hordein content of double-null flour samples was 2.9% relative to the wild-type cv Sloop, whereas the remaining hordein content of the two selected hordein triple-null lines, T2-4-8 and T2-6-A5 were 3.9 and 1.5 ug/g (parts per million, ppm; Table 6) both significantly below the FSANZ legislated level of 20 ppm for gluten in gluten free food and approximately 15,000 fold lower than in the wild-type cv Sloop grain.

Determination of Hordein Content of ULG3.0 Beer by Multiple Reaction Monitoring Mass Spectrometry (MRM MS)

The hordein content of beer brewed from barley ULG3.0 grain was measured by MRM MS, detecting specific peptide sequences, using the methods as described in Examples 3 and 4 with slight modifications. The data are presented in FIG. 7. The assays showed the lack of avenin-like A protein, B1- and B3-hordeins, D-hordein and reduced levels of gamma-1-hordein and gamma-3-hordein, in that these were not detected above the background noise in the mass spectrometry (FIG. 7). The assays also showed the absence of C-hordein.

TABLE 6

Summary of hordein content of hordein single-, double- and triple-null lines.

| Line | mg Hordein/gm flour | % of Sloop |
|---|---|---|
| Sloop | 56.6 ± 3.3 | 100% |
| Risø56 | 33.3 ± 1.1 | 58.8% |
| Risø1508 | 4.9 ± 0.26 | 8.7% |
| ULG2.0 | 1.67 ± 0.07 | 2.9% |
| T2-4-8 (ULG3.0) | 0.0039 ± 0.0017 | 0.007% |
| T2-6-A5 | 0.0015 ± 0.0004 | 0.0027% |

Determination of Hordein Content of ULG3.1 and ULG3.2 Flours by MRM MS

The hordein content of flour milled from grains of the ULG3.1 line and 10 candidate lines for ULG3.2 was determined by MRM MS as described for the ULG3.0 grain. Half-grains were milled to flour and the prolamin proteins from 20 mg flour (n=4 replicates) were extracted, alkylated, trypsin digested and analysed by MRM MS as described above. The data are plotted in FIG. 8, which show the mean peak area for each peptide (sum of three MRM transitions) from each half-grain of ULG3.1 and lines arising from the double parental intercross lines designated 043-2-148-2. These are plotted in comparison with control barley (wild-type cultivars Sloop, Baudin, Commander and Hindmarsh) and the triple-null line T2-4-8. The peak area is shown for a selected prototypic peptide, representative of each hordein family, Uniprot accession and amino acid sequences as follows:

```
A-F2EGD5_QQCCQPLAQISEQAR
(SEQ ID NO: 52; from F2EGD5, central to avenin-
like A protein)

B1-Q40020_VFLQQQCSPVR
(SEQ ID NO: 53; close to the N-terminus of
B1-hordein)

B3-Q4G3S1_VFLQQQCSPVPMPQR
(SEQ ID NO: 54)

C-Q40055_QLNPSHQELQSPQQPFLK
(SEQ ID NO: 55; close to the N-terminus of
C-hordein)

D-Q84LE9_ELQESSLEACR
(SEQ ID NO: 56; from Q84LE9, before the stop
codon at Y150)

G1-P17990_APFVGVVTGVGGQ
(SEQ ID NO: 57; from P17990, C-terminal
peptide),
and

G3-P80198_QQCCQQLANINEQSR
(SEQ ID NO: 58; from P80198, central to
γ3-hordein).
```

The level of D-hordein in the bi-parental intercross grains shown in FIG. 8 was similar to that in grain from ULG2.0 and the hordein triple null lines T2-4-8 and T2-6-A5, near zero, confirming the observation by 2D PAGE that D-hordein was not detected in grains from the T2-4-8 and T2-6-A5 lines. The level of gamma−1-hordein in these bi-parental intercrossed grain was also similar to that in ULG2.0 and the hordein triple null lines T2-4-8 and T2-6-A5. Several ULG3.2 lines had near zero level of the peptide APFVGVVTGVGGQ (SEQ ID NO: 59). Gamma−1-hordein was not detected by 2D PAGE of T2-4-8 and T2-6-A5 lines. The level of gamma-3-hordein in the bi-parental intercross grains was also similar to that in ULG2.0 and the hordein triple null lines except for line 124.1 (ULG3.2) in which it was very low. Gamma-3-hordein was also detected at reduced levels by 2D PAGE of the T2-4-8 and T2-6-A5 lines.

Interestingly, a synergistic effect was seen of the Hor2 and lys3a mutations in reducing the D-hordein content in ULG2.0 even though no Hor3 mutation (D-hordein) was present. In a similar fashion, the presence of all three mutations (Hor2-lys3a-Hor3) had a synergistic effect on reducing accumulation of the gamma-1- and gamma-2-hordeins as defined by the peptides above.

Example 10. Generation of Hull-Less Triple Null Barley Mutants

The barley grains for selections ULG3.0, ULG3.1 and ULG3.2 were all hulled, which is of benefit to the brewing industry as the spent husks form a filtration bed during the final stages of wort filtration (lautering). However, barley grain hulls have large numbers of tiny silica spikes and therefore the hulls need to be removed by pearling before human consumption. An alternative approach is to produce hull-less grains by genetic means. Therefore, plants of ULG3.0 were crossed with a hull-less barley variety designated Barleymax II (WO2011/011833) and a hull-less, hordein B-, C-, D- triple null mutant (Hor2-lys3a-Hor3) plant selected which was wild-type for the SSIIa gene.

Some F6 hordein triple-null hull-less selections (eg A7_1) contained less than 0.1 ppm total hordein in flour after three rounds of single seed descent.

Example 11. Mutagenesis of Barley

To isolate mutants in selected genes in barley, ethylmethanesulfonate (EMS) mutagenesis was carried out as described by Caldwell (2004). Approximately 45,000 (1.5 kg) grain of ULG3.0 were mutagenised as follows: the grain was imbibed in 2.5 L of distilled water for 4 hr at room temperature with aeration. The water was changed every hour for the duration of imbibition. The seeds were then incubated in 2.5 L of freshly prepared 30 mM EMS in 0.1 M phosphate buffer (pH7) for 16 h at room temperature with aeration. The seeds were then washed with 2.5 L of 100 mM sodium thiosulphate for 10 min at room temperature. The washing with thiosulphate was repeated, and the grains then rinsed thoroughly with 2×2 L of distilled water for 30 min at room temperature with aeration. The seeds were air-dried overnight on absorbent filter paper under a flowing air stream, prior to planting in the field the next day. Bulk M2 seeds were harvested, pooled and analysed for mutants. The mutational frequency after such treatment was approximately 1 mutant in a gene of interest per 1000 seeds. The seeds were screened for the loss of expression of the gamma-3 hordein by dot blot on half-grains using a gamma-3 hordein specific monoclonal antibody, and 40 grains which yielded a negative signal were identified from several tens of thousands of M2 grains. The lack of gamma-3 hordein in these grains was confirmed by Western blotting using the monoclonal antibody, and by mass spectrometry for a specific peptide (SEQ ID NO:58). The half-grains comprising the embryo from each negative grain were plated on media to allow for germination. The embryos in most of the half-grains did not germinate but a few did.

Example 12. Production of Beer from Low Hordein Barley

Brewing trials were carried out using malt produced from ULG2.0 grain by standard methods, and compared with the control wild-type barley cv. Gairdner. Gairdner is a high yielding mid to late maturing semi-dwarf 2-row barley variety grown widely throughout the Australian cereal growing regions. It produces good grain size under favourable conditions, producing moderate extract levels, fermentability and diastatic power, and therefore represents an industry "standard" so is ideal for its use as a control in brewing evaluation trials. The malt produced from ULG2.0 had a slightly higher moisture content of 5.7% compared to Gairdner malt (5.0%) and in appearance was significantly different to Gairdner malt, in that the grain appeared dented and shriveled. The Diastatic Power (DP) of the ULG2.0 malt was 54WK, much lower than the DP for Gairdner at 299WK. Malted barley generally has a DP of at least 250 KW. However, the ULG2.0 malt was negative for starch after 20 min mash time and achieved an LG result of 1.7° Plato.

The malt was milled by two passes through a 2-roller mill and achieved satisfactory cracking of the grain. The malt would be best suited for more complex milling in a six roller mill due to its grain morphology. Alternatively, a hammer mill in conjunction with a mash filter could be used, rather than a lauter tun for wort separation. The milled product was mashed by standard methods, at an initial temperature of 65° C. for 20 min, then 74° C. for 5 min, with the addition of extra sparge liquor. Overall, the shriveled morphology of the ULG2.0 malt made it difficult to mill and mash satisfactorily in comparison to regular malt. The mashed products were then lautered, where again the shriveled morphology of ULG2.0 caused difficulties. The lautering bed fell apart with chanelling so the run off needed to be stopped and the lautering bed re-raked. A considerable amount of potential extract was lost during the lautering process due to the inefficient milling, achieving an all in kettle value of 10.96° and 11.12° Plato when the target was to achieve 14° Plato. The pH, EBC colour and beta-glucan levels were acceptable. The milling deficiency also meant there was not an efficient formation of a bed of husks to act as a filter medium, contributing to a lower the expected extract. The clarity of run-off was initially very hazy, due to poor bed formation, although the wort clarity improved to be acceptable by 30 L of runoff.

The resultant wort was fermented with yeast strain Saccharomyces uvarum A at 18.5° C. for 120 hr. The fermentation profile was normal, there was no extended lag phase at the start of fermentation, although significant levels of diacetyl remained even after an extended diacetyl rest phase was given after the end of fermentation gravity was reached. Diacetyl rest is where the beer is left at higher fermentation temperatures prior to chilling the beer to 0° C. to allow the yeast to reabsorb and metabolise diacetyl. Generally 24 hr at end of fermentation is required to allow the yeast time to break this product down. This did not occur with both of the ULG2.0 trial brews. Isomerised hop extract was added at 30 mg/L and the liquor clarified with addition of Silica Hydrogel. The finished bright beer had a lower physical stability than the control brew. Initial chill haze was considered high and the forced chill haze results were outside of normal specifications. However, the chill haze did not form particulates.

The finished beer was subjected to sensory analysis by a panel of trained brewers, and despite the difficulties in the milling and lautering processes, the results were surprisingly good given the issues associated with the brewing performance of the malt. DMS (dimethyl sulphide) was the predominate flavour; however this was not seen as objectionable. The presence of DMS is often considered a flavour fault in Australian beer but is generally well accepted in European, particularly German beers. The brewers' comments were that the ULG2.0 beers were not too dissimilar to the control beers and that they were very passable as a beer, and reminiscent of German Beers. There was no overt "grainy" or "cereal" type flavours and no harshness or astringency with the ULG2.0 beer as can be typical of commercial beers marketed as "Gluten free". Overall the flavour profile was acceptable and reasonable.

Beer was made from barley grain of ULG3.0 by the same method as for ULG2.0, and is made from barley grain of ULG3.2. Malting of the ULG3.0 grain was improved relative to the ULG3.0 grain, mainly because the milling step was improved due to the grain being less shriveled. The beer made from ULG3.0 was of a good quality with an acceptable and reasonable flavor. The improved grain morphology (size and shape) of the grain from ULG3.2 provides for easier milling and lautering in the brewing process, providing beer with less than 1 ppm of total hordeins.

Example 13. Production of Food Using ULG Barley

Two small-scale (10 g) breads are baked using the ULG3.0 and ULG3.2 barley lines. Small-scale loaves are baked for test purposes, but the method can be readily scaled up to commercial quantities. One bread is made with 100% ULG barley flour as the flour ingredient, milled as described above, while the second bread is made with a blend of 30% flour and 70% commercial non-gluten flour such as rice flour as the flour ingredient. Flour (13.02 g) and the other ingredients are mixed into a dough, to peak dough development time in a 35-g mixograph. The recipe to be used, based on the 13.02 g of flour in each case is: flour 100%, salt 2%, dry yeast 1.5%, vegetable oil 2%, and improver 1.5%. The water addition level is based on the micro Z-arm water absorption values that are adjusted for the full formula. The moulding and panning are done in two-stage proofing steps at 40° C. and 85% room humidity. Baking is done in a Rotel oven for 14 min at 190° C.

The breads comprise a gluten content of less than 20 ppm and are suitable for human consumption by subjects having CD.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013902140 filed 13 Jun. 2013, and AU 2013902565 filed 11 Jul. 2013, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Almeida and Allshire (2005) TRENDS Cell Biol 15: 251-258. Anderson et al. (2000) Nature Medicine 6:337-342.
Anderson et al. (2013) Genome 56:179-185.
Bibikova et al. (2001) Mol. Cell. Biol. 21: 289-287.
Bibikova et al. (2002) Genetics 161:1169-1175.
Bourque (1995) Plant Sci. 105: 125-149. Brandt et al. (1990) Eur J Biochem 194:499-505.
Brennan et al. (1998) J Cereal Sci. 28:291-299.
Caldwell (2004) The Plant Journal 40:143-150.
Cameron-Mills et al., (1998). Plant Mol Biol 11: 449-461.
Capecchi (1980) Cell 22:479-488. Catassi et al. (1994) Lancet 343:200-203.
Certo et al. (2012) Nat Methods 8:941-943.
Cheng et al. (1996) Plant Cell Rep. 15:653-657.
Clapp (1993) Clin. Perinatol. 20:155-168.
Colgrave et al., (2012) J. Proteome Res. 11: 386-396.
Comai et al. (2004) Plant J 37: 778-786.
Curiel et al. (1992) Hum. Gen. Ther. 3:147-154.
Davies et al. (1993) Cell Biology International Reports 17:195-202.
De Anglis et al. (2007) J Food Protection 70:135-144.
Doll (1983) Barley seed proteins and possibilities for their improvement. In "Seed Proteins: Biochemistry, Genetics, Nutritional Value", Gottschalk W, Muller H P (eds).
Martinus Nijhoff, The Hague:207-223.
Doll et al (1973) Barley Genetics Newsletter 3:12-13.
Dostalek et al. (2006). Food Additives and Contaminants 23:1074-1078.
Doyon et al. (2010) Nat. Methods 7:459-460.
Doyon et al. (2011) Nat. Methods 8:74-79.
Eglitis et al. (1988) Biotechniques 6:608-614.
Fasoli et al., (2010). J. Proteome Res. 9: 5262-6269.
Field et al. (1982) Theoretical and Applied Genetics 62:329-336.
Fowell et al. (2006) Qjm-an International Journal of Medicine 99:453-460.
Fujimura et al. (1985) Plant Tissue Culture Letters 2:74.
Graham et al. (1973) Virology 54:536-539.
Grant et al. (1995) Plant Cell Rep. 15:254-258.
Green (2009) Journal of the American Medical Association 302:1225-1226.
Green and Jabri (2006) Annual Review of Medicine 57:207-221.
Groenen et al. (1993) Mol. Microbiol. 10:1057-1065.
Gu et al. (2003) Genome 46:1084-1097.
Guo et al. (2010) J. Mol. Biol. 400:96-107
Haft et al. (2005) Computational Biology 1(6):e60
Haseloff and Gerlach (1988) Nature 334:585-591.
Hausch et al. (2002) Gastroenterology 122:A180.
Henikoff et al. (2004) Plant Physiol 135: 630-636.
Hoe et al. (1999) Emerg. Infect. Dis. 5:254-263.
Ishino et al. (1987) J. Bacteriol. 169:5429-5433.
Janssen et al. (2002) OMICS J. Integ. Biol. 6:23-33.
Jaradat (1991) Theor Appl Genet 83:164-168.
Kahlenberg et al. (2006) European Food Research Technology. 222:78-82.
Kasarda et al. (1984) PNAS 81:4712-4716.
Kikuchi et al., (2003). Theor Appl Genetics 108: 73-78.
Kim et al. (1996) Proc. Natl. Acad. Sci. USA 93:1156-1160
Kim et al. (2012) Genome Res. 22:1327-1333.

Koziel et al. (1996) Plant Mol. Biol. 32:393-405.
Kreis and Shewry (1989) BioEssays 10:201-207.
Kreis et al. (1983) Cell: 34:161-167.
Kristoffersen et al., (2000) Electrophoresis 21: 3693-3700.
Kupper (2005) Gastroenterology 128:S121-127.
Lanzini et al. (2009) Alimentary Pharmacology & Therapeutics 29:1299-1308.
Lee et al. (2007). Journal of Human Nutrition and Dietetics 20:423-430.
Lu et al. (1993) J. Exp. Med. 178:2089-2096.
Marti et al. (2005) J Pharmacol Exp Therapeut 312:19-26.
Masepohl et al. (1996) Biochim. Biophys. Acta 1307:26-30.
McConnell Smith et al. (2009) PNAS 106:5099-5104.
Millar and Waterhouse (2005) Funct Integr Genomics 5:129-135.
Miller et al. (2007) Nat. Biotechnol. 25:778-785.
Mojica et al. (1995) Mol. Microbiol. 17:85-93.
Mojica et al. (2000) Mol. Microbiol. 36:244-246.
Moravcova et al. (2009). Journal of Chromatography a 1216:3629-3636.
Nakata et al. (1989) J. Bacteriol. 171:3553-3556.
Ohlund et al. (2010). Journal of Human Nutrition and Dietetics 23:294-300.
Pasquinelli et al. (2005) Cuff Opin Genet Develop 15: 200-205.
Perriman et al. (1992) Gene 113: 157-163.
Picariello et al. (2011). Food Chemistry 124:1718-1726.
Ramirez et al. (2012) Nucleic Acids Res. 40:5560-5568.
Rubio-Tapia et al. (2010). American Journal of Gastroenterology 105:1412-1420.
Senior (1998) Biotech. Genet. Engin. Revs. 15: 79-119.
Shan et al. (2002). Science 297:2275-2279.
Shewry (1995) Biological Reviews of the Cambridge Philosophical Society 70:375-426.
Shewry and Halford (2002) Journal of Experimental Botany 53:947-958.
Shewry and Tatham (1990) Biochemical Journal 267:1-12.
Shewry, et al., (1999) The prolamins of the Triticeae. In Seed Proteins, Klewer: London, 1999; pp 35-78.
Shippy et al. (1999) Mol. Biotech. 12: 117-129.
Skovbjerg et al. (2005) Diabetologia 48:1416-1417.
Skovbjerg et al., (2004). Biochim. et Biophys. Acta—Mol. Bas. of Dis. 1690:220-230.
Slade and Knauf (2005) Transgenic Res 14: 109-115.
Smith et al. (2000) Nature 407: 319-320.
Stepniak et al. (2006) Am J Physiol-Gastrointest Liver Physiol 291:621-629.
Szczepek et al. (2007) Nat. Biotechnol. 25:786-793.
Tanner et al. (2013) Plos One: 8: e56456.
Tanner et al., (2010). Aliment Pharmacol Ther. 32: 1184-1191.
Tjon et al. (2010) Immunogenetics 62:641-651.
Toriyama et al. (1986) Theor. Appl. Genet. 205:34.
Tye-Din et al. (2010) Science Translational Medicine 2:41-51.
van Embden et al. (2000) J. Bacteriol. 182:2393-2401.
Wagner et al. (1992) Proc. Natl. Acad. Sci. USA 89:6099-6103.
Wang et al. (2012) Genome Res. 22:1316-1326.
Waterhouse et al. (1998) Proc. Natl. Acad. Sci. USA 95: 13959-13964.
Wijngaard and Arendt (2007) Brewer & Distiller International 3: 31-32.
Wild et al. (2010). Alimentary Pharmacology & Therapeutics 32:573-581.

SEQUENCE LISTING

```
Sequence total quantity: 85
SEQ ID NO: 1            moltype = AA  length = 16
FEATURE                 Location/Qualifiers
source                  1..16
                        mol_type = protein
                        organism = Triticum aestivum
SEQUENCE: 1
ELQPFPQPEL PYPQPQ                                                   16

SEQ ID NO: 2            moltype = AA  length = 15
FEATURE                 Location/Qualifiers
source                  1..15
                        mol_type = protein
                        organism = Hordeum vulgare
SEQUENCE: 2
EQPFPQPEQP FPWQP                                                    15

SEQ ID NO: 3            moltype = AA  length = 16
FEATURE                 Location/Qualifiers
source                  1..16
                        mol_type = protein
                        organism = Hordeum vulgare
SEQUENCE: 3
EPEQPIPEQP QPYPQQ                                                   16

SEQ ID NO: 4            moltype = AA  length = 17
FEATURE                 Location/Qualifiers
source                  1..17
                        mol_type = protein
                        organism = Triticum aestivum
SEQUENCE: 4
QLQPFPQPQL PYPQPQS                                                  17

SEQ ID NO: 5            moltype = AA  length = 15
FEATURE                 Location/Qualifiers
source                  1..15
```

```
                        mol_type = protein
                        organism = Triticum aestivum
SEQUENCE: 5
QQCCQPLAQI SEQAR                                                    15

SEQ ID NO: 6            moltype = AA  length = 11
FEATURE                 Location/Qualifiers
source                  1..11
                        mol_type = protein
                        organism = Hordeum vulgare
SEQUENCE: 6
MVLQTLPSMC R                                                        11

SEQ ID NO: 7            moltype = AA  length = 8
FEATURE                 Location/Qualifiers
source                  1..8
                        mol_type = protein
                        organism = Hordeum vulgare
SEQUENCE: 7
PQQPFPQQ                                                            8

SEQ ID NO: 8            moltype = AA  length = 16
FEATURE                 Location/Qualifiers
source                  1..16
                        mol_type = protein
                        organism = Hordeum vulgare
SEQUENCE: 8
FVQPQQQPFP LQPHQP                                                   16

SEQ ID NO: 9            moltype = AA  length = 15
FEATURE                 Location/Qualifiers
source                  1..15
                        mol_type = protein
                        organism = Hordeum vulgare
SEQUENCE: 9
YPEQPQQPFP WQQPT                                                    15

SEQ ID NO: 10           moltype = AA  length = 19
FEATURE                 Location/Qualifiers
source                  1..19
                        mol_type = protein
                        organism = Hordeum vulgare
SEQUENCE: 10
LERPQQLFPQ WQPLPQQPP                                                19

SEQ ID NO: 11           moltype = AA  length = 18
FEATURE                 Location/Qualifiers
source                  1..18
                        mol_type = protein
                        organism = Hordeum vulgare
SEQUENCE: 11
LIIPQQPQQP FPLQPHQP                                                 18

SEQ ID NO: 12           moltype = AA  length = 5
FEATURE                 Location/Qualifiers
source                  1..5
                        mol_type = protein
                        organism = Secale cereale
SEQUENCE: 12
QQPFP                                                               5

SEQ ID NO: 13           moltype = AA  length = 5
FEATURE                 Location/Qualifiers
source                  1..5
                        mol_type = protein
                        organism = Secale cereale
SEQUENCE: 13
QQQFP                                                               5

SEQ ID NO: 14           moltype = AA  length = 5
FEATURE                 Location/Qualifiers
source                  1..5
                        mol_type = protein
                        organism = Secale cereale
SEQUENCE: 14
LQPFP                                                               5

SEQ ID NO: 15           moltype = AA  length = 5
FEATURE                 Location/Qualifiers
```

```
source                  1..5
                        mol_type = protein
                        organism = Secale cereale
SEQUENCE: 15
QLPFP                                                           5

SEQ ID NO: 16           moltype = AA  length = 16
FEATURE                 Location/Qualifiers
source                  1..16
                        mol_type = protein
                        organism = Hordeum vulgare
SEQUENCE: 16
RVVDQQLVGQ LPWSTG                                               16

SEQ ID NO: 17           moltype = AA  length = 16
FEATURE                 Location/Qualifiers
source                  1..16
                        mol_type = protein
                        organism = Hordeum vulgare
SEQUENCE: 17
VVDQQLVGQL PWSTGL                                               16

SEQ ID NO: 18           moltype = AA  length = 15
FEATURE                 Location/Qualifiers
source                  1..15
                        mol_type = protein
                        organism = Hordeum vulgare
SEQUENCE: 18
VVDQQLVGQL PWSTG                                                15

SEQ ID NO: 19           moltype = AA  length = 12
FEATURE                 Location/Qualifiers
source                  1..12
                        mol_type = protein
                        organism = Hordeum vulgare
SEQUENCE: 19
VVDQQLVGQL PW                                                   12

SEQ ID NO: 20           moltype = AA  length = 12
FEATURE                 Location/Qualifiers
source                  1..12
                        mol_type = protein
                        organism = Hordeum vulgare
SEQUENCE: 20
QLVGQLPWST GL                                                   12

SEQ ID NO: 21           moltype = AA  length = 11
FEATURE                 Location/Qualifiers
source                  1..11
                        mol_type = protein
                        organism = Hordeum vulgare
SEQUENCE: 21
QLVGQLPWST G                                                    11

SEQ ID NO: 22           moltype = AA  length = 13
FEATURE                 Location/Qualifiers
source                  1..13
                        mol_type = protein
                        organism = Hordeum vulgare
SEQUENCE: 22
LVGQLPWSTG LQM                                                  13

SEQ ID NO: 23           moltype = AA  length = 11
FEATURE                 Location/Qualifiers
source                  1..11
                        mol_type = protein
                        organism = Hordeum vulgare
SEQUENCE: 23
LVGQLPWSTG L                                                    11

SEQ ID NO: 24           moltype = AA  length = 10
FEATURE                 Location/Qualifiers
source                  1..10
                        mol_type = protein
                        organism = Hordeum vulgare
SEQUENCE: 24
LVGQLPWSTG                                                      10

SEQ ID NO: 25           moltype = AA  length = 12
```

```
FEATURE                 Location/Qualifiers
source                  1..12
                        mol_type = protein
                        organism = Hordeum vulgare
SEQUENCE: 25
VGQLPWSTGL QM                                                   12

SEQ ID NO: 26           moltype = AA  length = 10
FEATURE                 Location/Qualifiers
source                  1..10
                        mol_type = protein
                        organism = Hordeum vulgare
SEQUENCE: 26
VGQLPWSTGL                                                      10

SEQ ID NO: 27           moltype = AA  length = 15
FEATURE                 Location/Qualifiers
MOD_RES                 1
                        note = Pyroglutamic acid
MOD_RES                 15
                        note = HexNAc
source                  1..15
                        mol_type = protein
                        organism = Hordeum vulgare
SEQUENCE: 27
QLAAQLPAMC RLEGS                                                15

SEQ ID NO: 28           moltype = AA  length = 26
FEATURE                 Location/Qualifiers
source                  1..26
                        mol_type = protein
                        organism = Hordeum vulgare
SEQUENCE: 28
VVRQYEQQTE VPSKGGSFYP GGTAPP                                    26

SEQ ID NO: 29           moltype = AA  length = 15
FEATURE                 Location/Qualifiers
source                  1..15
                        mol_type = protein
                        organism = Hordeum vulgare
SEQUENCE: 29
FVLPQQQAQF KVVGS                                                15

SEQ ID NO: 30           moltype = AA  length = 10
FEATURE                 Location/Qualifiers
source                  1..10
                        mol_type = protein
                        organism = Hordeum vulgare
SEQUENCE: 30
FVLPQQQAQF                                                      10

SEQ ID NO: 31           moltype = AA  length = 16
FEATURE                 Location/Qualifiers
source                  1..16
                        mol_type = protein
                        organism = Hordeum vulgare
SEQUENCE: 31
AIVMQQQVQQ QVGHGF                                               16

SEQ ID NO: 32           moltype = AA  length = 19
FEATURE                 Location/Qualifiers
source                  1..19
                        mol_type = protein
                        organism = Hordeum vulgare
SEQUENCE: 32
LERPQQLFPQ WQPLPQQPP                                            19

SEQ ID NO: 33           moltype = AA  length = 13
FEATURE                 Location/Qualifiers
source                  1..13
                        mol_type = protein
                        organism = Hordeum vulgare
SEQUENCE: 33
LFPQWQPLPQ QPP                                                  13

SEQ ID NO: 34           moltype = AA  length = 12
FEATURE                 Location/Qualifiers
source                  1..12
                        mol_type = protein
```

```
                        organism = Hordeum vulgare
SEQUENCE: 34
LQQLGQGMPI QL                                                   12

SEQ ID NO: 35           moltype = AA  length = 9
FEATURE                 Location/Qualifiers
source                  1..9
                        mol_type = protein
                        organism = Hordeum vulgare
SEQUENCE: 35
VVGSLVIQT                                                       9

SEQ ID NO: 36           moltype = AA  length = 19
FEATURE                 Location/Qualifiers
source                  1..19
                        mol_type = protein
                        organism = Hordeum vulgare
SEQUENCE: 36
LQQPQHQFPQ PTQQFPQRP                                            19

SEQ ID NO: 37           moltype = AA  length = 15
FEATURE                 Location/Qualifiers
source                  1..15
                        mol_type = protein
                        organism = Hordeum vulgare
SEQUENCE: 37
YPEQPQQPFP WQQPT                                                15

SEQ ID NO: 38           moltype = AA  length = 12
FEATURE                 Location/Qualifiers
source                  1..12
                        mol_type = protein
                        organism = Hordeum vulgare
SEQUENCE: 38
GVVQPQQLAQ ME                                                   12

SEQ ID NO: 39           moltype = AA  length = 17
FEATURE                 Location/Qualifiers
MOD_RES                 1
                        note = Pyroglutamic acid
source                  1..17
                        mol_type = protein
                        organism = Hordeum vulgare
SEQUENCE: 39
QPQHQFPQPT QQFPQRP                                              17

SEQ ID NO: 40           moltype = AA  length = 14
FEATURE                 Location/Qualifiers
source                  1..14
                        mol_type = protein
                        organism = Hordeum vulgare
SEQUENCE: 40
FVQPQQQVPV EITR                                                 14

SEQ ID NO: 41           moltype = AA  length = 12
FEATURE                 Location/Qualifiers
source                  1..12
                        mol_type = protein
                        organism = Hordeum vulgare
SEQUENCE: 41
FVQPQQQVPV EI                                                   12

SEQ ID NO: 42           moltype = AA  length = 18
FEATURE                 Location/Qualifiers
source                  1..18
                        mol_type = protein
                        organism = Hordeum vulgare
SEQUENCE: 42
LIIPQQPQQP FPLQPHQP                                             18

SEQ ID NO: 43           moltype = AA  length = 17
FEATURE                 Location/Qualifiers
source                  1..17
                        mol_type = protein
                        organism = Hordeum vulgare
SEQUENCE: 43
IIPQQPQQPF PLQPHQP                                              17

SEQ ID NO: 44           moltype = AA  length = 12
```

```
FEATURE                 Location/Qualifiers
source                  1..12
                        mol_type = protein
                        organism = Hordeum vulgare
SEQUENCE: 44
VQVQIPFVHP SI                                                   12

SEQ ID NO: 45           moltype = AA  length = 15
FEATURE                 Location/Qualifiers
source                  1..15
                        mol_type = protein
                        organism = Hordeum vulgare
SEQUENCE: 45
SFGQPQQQVP VEVMR                                                15

SEQ ID NO: 46           moltype = AA  length = 28
FEATURE                 Location/Qualifiers
source                  1..28
                        mol_type = protein
                        organism = Hordeum vulgare
SEQUENCE: 46
IIPQQPFPLQ PQPFPQQPQQ PLPQPQQP                                  28

SEQ ID NO: 47           moltype = AA  length = 14
FEATURE                 Location/Qualifiers
MOD_RES                 6
                        note = dansyl-glutamic acid (DEA)
source                  1..14
                        mol_type = protein
                        organism = Hordeum vulgare
SEQUENCE: 47
IPLQPQQPFP QQPP                                                 14

SEQ ID NO: 48           moltype = AA  length = 14
FEATURE                 Location/Qualifiers
source                  1..14
                        mol_type = protein
                        organism = Hordeum vulgare
SEQUENCE: 48
TLPTMCSVNV PLYR                                                 14

SEQ ID NO: 49           moltype = AA  length = 16
FEATURE                 Location/Qualifiers
source                  1..16
                        mol_type = protein
                        organism = Hordeum vulgare
SEQUENCE: 49
DVSPECRPVA LSQVVR                                               16

SEQ ID NO: 50           moltype = AA  length = 15
FEATURE                 Location/Qualifiers
source                  1..15
                        mol_type = protein
                        organism = Hordeum vulgare
SEQUENCE: 50
QQCCQQLANI NEQSR                                                15

SEQ ID NO: 51           moltype = AA  length = 17
FEATURE                 Location/Qualifiers
source                  1..17
                        mol_type = protein
                        organism = Hordeum vulgare
SEQUENCE: 51
CTAIDSIVHA IFMQQGR                                              17

SEQ ID NO: 52           moltype = AA  length = 15
FEATURE                 Location/Qualifiers
source                  1..15
                        mol_type = protein
                        organism = Hordeum vulgare
SEQUENCE: 52
QQCCQPLAQI SEQAR                                                15

SEQ ID NO: 53           moltype = AA  length = 11
FEATURE                 Location/Qualifiers
source                  1..11
                        mol_type = protein
                        organism = Hordeum vulgare
SEQUENCE: 53
```

```
VFLQQQCSPV R                                                    11

SEQ ID NO: 54          moltype = AA  length = 15
FEATURE                Location/Qualifiers
source                 1..15
                       mol_type = protein
                       organism = Hordeum vulgare
SEQUENCE: 54
VFLQQQCSPV PMPQR                                                15

SEQ ID NO: 55          moltype = AA  length = 18
FEATURE                Location/Qualifiers
source                 1..18
                       mol_type = protein
                       organism = Hordeum vulgare
SEQUENCE: 55
QLNPSHQELQ SPQQPFLK                                             18

SEQ ID NO: 56          moltype = AA  length = 11
FEATURE                Location/Qualifiers
source                 1..11
                       mol_type = protein
                       organism = Hordeum vulgare
SEQUENCE: 56
ELQESSLEAC R                                                    11

SEQ ID NO: 57          moltype = AA  length = 13
FEATURE                Location/Qualifiers
source                 1..13
                       mol_type = protein
                       organism = Hordeum vulgare
SEQUENCE: 57
APFVGVVTGV GGQ                                                  13

SEQ ID NO: 58          moltype = AA  length = 15
FEATURE                Location/Qualifiers
source                 1..15
                       mol_type = protein
                       organism = Hordeum vulgare
SEQUENCE: 58
QQCCQQLANI NEQSR                                                15

SEQ ID NO: 59          moltype = AA  length = 13
FEATURE                Location/Qualifiers
source                 1..13
                       mol_type = protein
                       organism = Hordeum vulgare
SEQUENCE: 59
APFVGVVTGV GGQ                                                  13

SEQ ID NO: 60          moltype = DNA  length = 23
FEATURE                Location/Qualifiers
source                 1..23
                       mol_type = other DNA
                       note = Oligonucleotide primer
                       organism = synthetic construct
SEQUENCE: 60
gacacatatt ctgccaaaac ccc                                       23

SEQ ID NO: 61          moltype = DNA  length = 20
FEATURE                Location/Qualifiers
source                 1..20
                       mol_type = other DNA
                       note = Oligonucleotide primer
                       organism = synthetic construct
SEQUENCE: 61
acgagggcga cgattaccgc                                           20

SEQ ID NO: 62          moltype = DNA  length = 25
FEATURE                Location/Qualifiers
misc_feature           1..25
                       note = Oligonucleotide primer
source                 1..25
                       mol_type = other DNA
                       organism = synthetic construct
SEQUENCE: 62
gagatcaatt cattgacagt ccacc                                     25

SEQ ID NO: 63          moltype = DNA  length = 24
```

```
FEATURE                 Location/Qualifiers
source                  1..24
                        mol_type = other DNA
                        note = Oligonucleotide primer
                        organism = synthetic construct
SEQUENCE: 63
cttgtcctga ctgctgcgga gaaa                                          24

SEQ ID NO: 64           moltype = DNA  length = 25
FEATURE                 Location/Qualifiers
source                  1..25
                        mol_type = other DNA
                        note = Oligonucleotide primer
                        organism = synthetic construct
SEQUENCE: 64
gcaacaagga cactacccaa gtatg                                         25

SEQ ID NO: 65           moltype = DNA  length = 25
FEATURE                 Location/Qualifiers
source                  1..25
                        mol_type = other DNA
                        note = Oligonucleotide primer
                        organism = synthetic construct
SEQUENCE: 65
gctgacaatg agctgagaca tgtag                                         25

SEQ ID NO: 66           moltype = DNA  length = 19
FEATURE                 Location/Qualifiers
source                  1..19
                        mol_type = other DNA
                        note = Oligonucleotide primer
                        organism = synthetic construct
SEQUENCE: 66
ggcaatacga gcagcaaac                                                19

SEQ ID NO: 67           moltype = DNA  length = 20
FEATURE                 Location/Qualifiers
source                  1..20
                        mol_type = other DNA
                        note = Oligonucleotide primer
                        organism = synthetic construct
SEQUENCE: 67
cctctgtcct ggttgttgtc                                               20

SEQ ID NO: 68           moltype = DNA  length = 20
FEATURE                 Location/Qualifiers
source                  1..20
                        mol_type = other DNA
                        note = Oligonucleotide primer
                        organism = synthetic construct
SEQUENCE: 68
tcgcaggatc ctgtacaacg                                               20

SEQ ID NO: 69           moltype = DNA  length = 20
FEATURE                 Location/Qualifiers
source                  1..20
                        mol_type = other DNA
                        note = Oligonucleotide primer
                        organism = synthetic construct
SEQUENCE: 69
caacaatgaa gaccttcctc                                               20

SEQ ID NO: 70           moltype = DNA  length = 22
FEATURE                 Location/Qualifiers
source                  1..22
                        mol_type = other DNA
                        note = Oligonucleotide primer
                        organism = synthetic construct
SEQUENCE: 70
cgagaaggta ccattactcc ag                                            22

SEQ ID NO: 71           moltype = DNA  length = 21
FEATURE                 Location/Qualifiers
source                  1..21
                        mol_type = other DNA
                        note = Oligonucleotide primer
                        organism = synthetic construct
SEQUENCE: 71
agtaacaatg aaggtccatc g                                             21
```

```
SEQ ID NO: 72          moltype = DNA  length = 2838
FEATURE                Location/Qualifiers
source                 1..2838
                       mol_type = genomic DNA
                       organism = Hordeum vulgare
SEQUENCE: 72
gacacatatt ctgccaaaac cccagaacaa taatcacttc tcgtagatga agagaacaga  60
ccaagataca aacgtccacg cttcagcaaa cagtacccca gaactaggat taagccgatt  120
acgcggcttt agcagaccgt ccaaaaaaac tgttttgcaa agctccaatt cctccttgct  180
tatccaattt cttttgtgtt ggcaaactgc acttgtccaa ccgattttgt tcttcccgtg  240
tttcttctta ggctaactaa cacagccgtg cacatagcca tggtccggaa tcttcacctc  300
gtccctataa aagcccagcc aatctccaca atctcatcat caccgagaac accgagaacc  360
acaaaactag agatcaattc attgacagtc caccgagatg gctaagcggc tggtcctctt  420
tgtggcggta atcgtcgccc tcgtggctct caccaccgct gaacgtgaga tcaatgggaa  480
caacattttc cttgatagcc gctctaggca gctacagtgt gagcgcgagc tccaggagag  540
ctcgctcgag gcgtgccggc gggtcgtgga ccaacagctg gttggccagc tgccatggag  600
cacggggctc cagatgcagt gctgccagca gcttcgggac gtcagccccg agtgccgccc  660
cgtcgccctc agccaggtcg tgaggcaata cgagcagcaa accgaggtgc catccaaggg  720
aggatccttc tacccgggcg ggaccgcacc gccgctgcag caaggaggat ggtggggaac  780
ctctgtaaaa tggtactacc cagaccaaac ttcttcgcaa cagtcatggc aagggcaaca  840
agggtaccac caaagcgtaa cttcttccca gcagccagga caagggcagc aagggtccta  900
cccaggttca actttcccgc agcagccagg acaaggacaa caaccaggac agaggcagcc  960
atggtcctat ccaagtgcaa ctttcccaca acagccaggg caagggcaag ggcaacaagg  1020
gtactaccca ggcgcaactt ccctgctgca gccaggacaa gggcaacaag ggccctacca  1080
gagtgcaact tctccacagc agccaggaca aggacaggga caccaagaga cctatcaatt  1140
tgcaacttcc ccgcatcagc caggacaatg gcaacaacca ggacaagggc aacaagggta  1200
ctacccaagt gtaacttctc cacaacagtc gggacaaggg caaacagggt acccaagtac  1260
aacttctcca caacaatcgg ggcaagggca acagctggga caagggcaac aaccaggaca  1320
agggcaacaa gggtacccaa gtgcaacttt tccacaacag ccaggacaat ggcaacaagg  1380
gtcctaccca agtacaactt ctccgcagca gtcaggacaa gggcaacaag ggtacaaccc  1440
aagtggaact tctacgcagc agccgggaca agtgcaacag ttgggacaag ggcaacaagg  1500
gtactaccca attgcaactt ctccgcagca gccaggacaa gggcaacagc taggacaagg  1560
gcaacaacca ggacatgggc aacagctagt gcaagggcaa caacaaggac aagggcaaca  1620
aggacactac ccaagtatga cttctccgca ccaaacagga caagggcaaa aaggatacta  1680
cccaagtgca atttctccgc agcagtcagg acaaggacaa caaggatacc agcctagtgg  1740
agcttcttca caggggtcgg tgcaaggggc gtgccagcac agcacatctt ctccgcagca  1800
gcaagcacaa gggtgccaag cttcttcacc aaagcaaggg ctagggtcgt tgtactaccc  1860
gagtggagct tatacacaac agaaaccagg gcaagggtac aacccaggtg gaacttctcc  1920
gctgcaccag caagggggag ggttcggcgg cgggttaacg acggagcaac cgcagggagg  1980
aaagcagcca ttccattgcc agcaaaccac tgtctcccct caccagggtc agcaaaccac  2040
tgtttcccct catcagggtc agcaaaccac tgtctcccct catcagggtc agcaaaccac  2100
tgtctcccct caccagggtc agcaaaccac cgtctcccct caccagggtc agcaaaccac  2160
cgtctcccct catcagggtc agcaaaccac tgtctcccct catccgggtc agcaaaccac  2220
tgtctcccct catcagggtc agcaaaccac tgtctcccct catccgggtc agcaaaccac  2280
tgtctcccct catcagggtc agcaaaccac tgtctcccct catcagggtc agcaaaccac  2340
cgtctcccct catcagggtc agcaaaccac cgtctcccct catcagggtc agcaaaccac  2400
cgtctcccct catcagggtc agcagcccgg cgagcagcct tgcggtttcc ctggccagca  2460
aaccaccgtg tctctgcacc atggtcagca gtccaacgag ttgtactacg gcagcccata  2520
ccatgttagc gtggagcagc cgtcggccag cctaaaggta gcaaaggcgc agcagctcgc  2580
ggcgcagctg ccggcaatgt gtcggctgga gggcggcggc ggcctgttgg ccagccagta  2640
gtagaactct ggcagctcgc atggtgcttg ggcatgcatg catcttagct atacaataaa  2700
cgtgacgtgt gcttgcagtt tttcatgtaa ctagggtaaa acccaacaat aatgcaaaac  2760
ggaaagcttc tccatccaaa aaaagaacaa aactggtgct atatatagta tgcgctacat  2820
gtctcagctc attgtcag                                                2838

SEQ ID NO: 73          moltype = DNA  length = 2724
FEATURE                Location/Qualifiers
source                 1..2724
                       mol_type = genomic DNA
                       organism = Hordeum vulgare
SEQUENCE: 73
gacacatatt ctgccaaaac cccagaacaa taatcacttc tcgtagatga agagaacaga  60
ccaagataca aacgtccacg cttcagcaaa cagtacccca gaactaggat taagccgatt  120
acgcggcttt agcagaccgt ccaaaaaaac tgttttgcaa agctccaatt cctccttgct  180
tatccaattt cttttgtgtt ggcaaactgc acttctccaa ccgattttgt tcttcccatg  240
tttcttctta ggctaactaa cacagccgtg cacatagcca tggtccggaa ccttcacctc  300
gtccctataa aagcccagcc aatctccaca atctcatcat caccgagaac accgagaacc  360
acaaaactag agatcaattc attgacagtc caccgagatg gctaagcggc tggtcctctt  420
tgtggcggta atcgtcgccc tcgtggctct caccaccgct gaacctgaga tcaatgggaa  480
caacattttc cttgatagcc gctctgggca gctacagtgt gagcgcgagc tccaggagag  540
ctcgctcgag gcgtgccggc gggtcgtgga ccaacagctg gttggccagc tgccatggag  600
cacggggctc cagatgcagt gctgccagca gcttcgggac gtcagccccg agtgccgccc  660
cgtcgccctc agccaggtcg tgaggcaata cgagcagcaa accgaggtgc catccaaggg  720
aggatccttc tacccgggcg ggaccgcacc gccgctgcag caaggaggat ggtggggaac  780
ctctgtaaaa tggtactacc cagaccaaac ttcttcgcaa cagtcatggc aagggcaaca  840
agggtagcac caaagcgtaa cttcttccca gcagccagga caagggcagc aagggtccta  900
cccaggttca actttcccgc agcagccagg acaaggacaa caaccaggac agaggcagcc  960
atggtcctat ccaagtgcaa ctttcccaca acagccaggg caagggcaag ggcaagggca  1020
```

```
acaagggtac tacccaggcg caacttccct gctgcagcca ggacaagggc aacaagggcc  1080
ctaccaaagt gcaacttctc cacagcagcc aggacaagga cagggacaac aagagcccta  1140
tccaattgca acttccccgc atcagccagg acaatggcaa caaccaggac aagggcaaca  1200
agggtactac ccaagtgtaa cttctccaca acagtcggga caagggcaac aagggtaccc  1260
aagtacaact tctccacaac aatcggggca agggcaacag ctgggacaag ggcaacaacc  1320
aggacaaggg caacaagggt acccaagtgc aacttttcca caacagccag gacaatggca  1380
acaagggtcc tacccaagta caacttctcc gcagcagtca ggacaagggc aacaagggta  1440
caacccaagt ggaacttcta cgcagcagcc gggacaagtg caacagttgg gacaagggca  1500
acaagggtac tacccaattg caacttctcc gcagcagcca ggacaagggc aacagctagg  1560
acaagggcaa caaccaggac atgggcaaca gctagtgcaa gggcaacaac aaggacaagg  1620
gcaacaagga cactacccaa gtatgacttc tccgcaccaa acaggacaag ggcaaaaagg  1680
atactaccca agtgcaattt ctccgcagca gtcaggacaa ggacaacaag gataccagcc  1740
tagtggagct tcttcacagg ggtcggtgca aggggcgtac cagcacagca catcttctcc  1800
gcagcagcaa gcacaagggt gccaagcttc ttcaccaaag caagggctag ggtcgttgta  1860
ctacccgagt ggagcttata cacaacagaa accagggcaa gggtacaacc caggtggaac  1920
ttctccgctg caccagcaag ggggagggtt cggcggcggg ttaacgacgg agcaaccgca  1980
gggaggaaag cagccattcc attgccagca aaccactgtc tcccctcacc agggtcagca  2040
aaccactgtc tcccctcatc agggtcagca aaccactgtc tcccctcatc agggtcagca  2100
aaccactgtc tcccctcacc agggtcagca aaccactgtc tcccctcatc cgggtcagca  2160
aaccactgtc tcccctcatc agggtcagca aaccactgtc tcccctcatc cgggtcagca  2220
aaccaccgtc tcccctcatc agggtcagca aaccaccgtc tcccctcatc agggtcagca  2280
aaccaccgtc tcccctcacc agggtcagca gcccggcgag cagccttgcg gtttccctgg  2340
ccagcaaacc accgtgtctc tgcaccatgg tcagcagtcc aacgagttgt actacggcag  2400
cccataccat gttagcgtgg agcagccgtc ggccagccta aaggtagcaa aggcgcagca  2460
gctcgcggca cagctgccgg caatgtgtcg gctggagggc ggcggcggcc tgttggccag  2520
ccagtagtag aactctggca gctcgcatgg tgcttgggca tgcatgcacc ttagctatac  2580
aataaacgtg acgtgtgctt gcagtttttc atgtaactag ggtaaaaccc aacaataatg  2640
caaaacggaa agcttctcca tccaaaaaaa gaacaaaact ggtgctatat atagtatgcg  2700
ctacatgtct cagctcattg tcag                                         2724
```

```
SEQ ID NO: 74          moltype = AA  length = 747
FEATURE                Location/Qualifiers
source                 1..747
                       mol_type = protein
                       organism = Hordeum vulgare
SEQUENCE: 74
MAKRLVLFVA VIVALVALTT AEREINGNNI FLDSRSRQLQ CERELQESSL EACRRVVDQQ  60
LVGQLPWSTG LQMQCCQQLR DVSPECRPVA LSQVVRQYEQ QTEVPSKGGS FYPGGTAPPL  120
QQGGWWGTSV KWYYPDQTSS QQSWQGQQGY HQSVTSSQQP GQGQQGSYPG STFPQQPGQG  180
QQPGQRQPWS YPSATFPQQP GQGQGQQGYY PGATSLLQPG QGQQGPYQSA TSPQQPGQGQ  240
GHQETYQFAT SPHQPGQWQQ PGQGQQGYYP SVTSPQQSGQ GQTGYPSTTS PQQSGQGQQL  300
GQGQQPGQGQ QGYPSATFPQ QPGQWQQGSY PSTTSPQQSG QGQQGYNPSG TSTQQPGQVQ  360
QLGQGQQGYY PIATSPQQPG QGQQLGQGQQ PGHGQQLVQG QQQGQGQQGH YPSMTSPHQT  420
GQGQKGYYPS AISPQQSGQG QQGYQPSGAS SQGSVQGACQ HSTSSPQQQA QGCQASSPKQ  480
GLGSLYYPSG AYTQQKPGQG YNPGGTSPLH QQGGGFGGGL TTEQPQGGKQ PFHCQQTTVS  540
PHQGQQTTVS PHQGQQTTVS PHQGQQTTVS PHQGQQTTVS PHQGQQTTVS PHQGQQTTVS  600
PHPGQQTTVS PHQGQQTTVS PHPGQQTTVS PHQGQQTTVS PHQGQQTTVS PHQGQQTTVS  660
PHQGQQTTVS PHQGQQPGEQ PCGFPGQQTT VSLHHGQQSN ELYYGSPYHV SVEQPSASLK  720
VAKAQQLAAQ LPAMCRLEGG GGLLASQ                                      747
```

```
SEQ ID NO: 75          moltype = AA  length = 149
FEATURE                Location/Qualifiers
source                 1..149
                       mol_type = protein
                       organism = Hordeum vulgare
SEQUENCE: 75
MAKRLVLFVA VIVALVALTT AEPEINGNNI FLDSRSGQLQ CERELQESSL EACRRVVDQQ  60
LVGQLPWSTG LQMQCCQQLR DVSPECRPVA LSQVVRQYEQ QTEVPSKGGS FYPGGTAPPL  120
QQGGWWGTSV KWYYPDQTSS QQSWQGQQG                                    149
```

```
SEQ ID NO: 76          moltype = DNA  length = 2244
FEATURE                Location/Qualifiers
source                 1..2244
                       mol_type = genomic DNA
                       organism = Hordeum vulgare
SEQUENCE: 76
atggctaagc ggctggtcct ctttgtggcg gtaatcgtcg ccctcgtggc tctcaccacc  60
gctgaacgtg agatcaatgg gaacaacatt ttccttgata gccgctctag gcagctacag  120
tgtgagcgcg agctccagga gagctcgctc gaggcgtgcc ggcgggtcgt ggaccaacag  180
ctggttggcc agctgccatg gagcacgggg ctccagatgc agtgctgcca gcagcttcgg  240
gacgtcagcc ccgagtgccg ccccgtcgcc ctcagccagg tcgtgaggca atacgagcag  300
caaaccgagg tgccatccaa gggaggatcc ttctacccgg gcgggaccgc accgccgctg  360
cagcaaggag gatggtgggg aacctctgta aaatggtact acccagacca aacttcttcg  420
caacagtcat ggcaagggca acaagggtac caccaaagcg taacttcttc ccagcagcca  480
ggacaagggc agcaagggtc ctacccaggt tcaactttcc cgcagcagcc aggacaagga  540
caacaaccag gacagaggca gccatggtcc tatccaagtg caactttccc acaacagcca  600
gggcaagggc aagggcaaca agggtactac ccaggcgcaa cttccctgct gcagccagga  660
caagggcaac aagggcccta ccagagtgca acttctccac agcagccagg acaaggacag  720
ggacaccaag agacctatca atttgcaact tccccgcatc agccaggaca atggcaacaa  780
```

```
ccaggacaag ggcaacaagg gtactaccca agtgtaactt ctccacaaca gtcgggacaa  840
gggcaaacag ggtacccaag tacaacttct ccacaacaat cggggcaagg gcaacagctg  900
ggacaagggc aacaaccagg acaagggcaa caagggtacc caagtgcaac ttttccacaa  960
cagccaggac aatggcaaca agggtcctac ccaagtacaa cttctccgca gcagtcagga  1020
caagggcaac aagggtacaa cccaagtgga acttctacgc agcagccggg acaagtgcaa  1080
cagttgggac aagggcaaca agggtactac ccaattgcaa cttctccgca gcagccagga  1140
caagggcaac agctaggaca agggcaacaa ccaggacatg ggcaacagct agtgcaaggg  1200
caacaacaag gacaagggca acaaggacac tacccaagta tgacttctcc gcaccaaaca  1260
ggacaagggc aaaaaggata ctacccaagt gcaatttctc cgcagcagtc aggacaagga  1320
caacaaggat accagcctag tggagcttct tcacaggggt cggtgcaagg ggcgtgccag  1380
cacagcacat cttctccgca gcagcaagca caagggtgcc aagcttcttc accaaagcaa  1440
gggctagggt cgttgtacta cccgagtgga gcttatacac aacagaaacc agggcaaggg  1500
tacaacccag gtggaacttc tccgctgcac cagcaagggg gagggttcgg cggcgggtta  1560
acgacggagc aaccgcaggg aggaaagcag ccattccatt gccagcaaac cactgtctcc  1620
cctcaccagg gtcagcaaac cactgtttcc cctcatcagg gtcagcaaac cactgtctcc  1680
cctcatcagg gtcagcaaac cactgtctcc cctcaccagg gtcagcaaac caccgtctcc  1740
cctcaccagg gtcagcaaac caccgtctcc cctcatcagg gtcagcaaac cactgtctcc  1800
cctcatccgg gtcagcaaac cactgtctcc cctcatcagg gtcagcaaac cactgtctcc  1860
cctcatccgg gtcagcaaac cactgtctcc cctcatcagg gtcagcaaac cactgtctcc  1920
cctcatcagg gtcagcaaac caccgtctcc cctcatcagg gtcagcaaac caccgtctcc  1980
cctcatcagg gtcagcaaac caccgtctcc cctcatcagg gtcagcagcc cggcgagcag  2040
ccttgcggtt tccctggcca gcaaaccacc gtgtctctgc accatggtca gcagtccaac  2100
gagttgtact acggcagccc ataccatgtt agcgtggagc agccgtcggc cagcctaaag  2160
gtagcaaagg cgcagcagct cgcggcgcag ctgccggcaa tgtgtcggct ggagggcggc  2220
ggcggcctgt tggccagcca gtag                                         2244

SEQ ID NO: 77          moltype = DNA  length = 450
FEATURE                Location/Qualifiers
source                 1..450
                       mol_type = genomic DNA
                       organism = Hordeum vulgare
SEQUENCE: 77
atggctaagc ggctggtcct ctttgtggcg gtaatcgtcg ccctcgtggc tctcaccacc  60
gctgaacctg agatcaatgg gaacaacatt ttccttgata gccgctctgg gcagctacag  120
tgtgagcgcg agctccagga gagctcgctc gaggcgtgcc ggcgggtcgt ggaccaacag  180
ctggttggcc agctgccatg gagcacgggg ctccagatgc agtgctgcca gcagcttcgg  240
gacgtcagcc ccgagtgccg ccccgtcgcc ctcagccagg tcgtgaggca atacgagcag  300
caaaccgagg tgccatccaa gggaggatcc ttctacccgg gcgggaccgc accgccgctg  360
cagcaaggag gatggtgggg aacctctgta aaatggtact acccagacca aacttcttcg  420
caacagtcat ggcaagggca acaagggtag                                   450

SEQ ID NO: 78          moltype = AA  length = 181
FEATURE                Location/Qualifiers
source                 1..181
                       mol_type = protein
                       organism = Hordeum vulgare
SEQUENCE: 78
LACEVLKERS VCILQLHYVQ PSILQQLNPC KVFLQQQCSP VRMPQLIARS QMLQQSSCHV  60
LQQQCCQQLP QIPEQFRHEA IRAIVYSIFL QEQPQQSVQG ASQPQQQLQE EQVGQCYFQQ  120
PQPQQLGQPQ QVPQSVFLQP HQIAQLEATN SIALRTLPTM CNVNVPLYDI MPFGVGTRVG  180
V                                                                  181

SEQ ID NO: 79          moltype = AA  length = 274
FEATURE                Location/Qualifiers
source                 1..274
                       mol_type = protein
                       organism = Hordeum vulgare
SEQUENCE: 79
MKTFLIFALL AIAATNTIAQ QQPFPQQPQP YPQQPQPYPQ QPFPPQQPFP QQPPFWWQQP  60
VQSQQQPCQQ QQTPLPQGQQ YQPLLQQQIP FVHPSVLQQL NPCKVFLQQQ CSPVPMPQRI  120
ARSQMLQQSS CHVLQQQCCK QLPQIPEQFR HEAIRAIIYS IILQEQQQVQ DFVQPQQQQP  180
QQSVQGVSQS QQQSQQPQLG QCSFQQPQLQ QLGQQPQQQQ VPLWAFLQPQ QMAQLEVMTS  240
VALRTLPTMC NVNVPLYGIT TSVPLSVGTG VGPY                              274

SEQ ID NO: 80          moltype = AA  length = 347
FEATURE                Location/Qualifiers
SITE                   161
                       note = misc_feature - Xaa can be any naturally occurring
                        amino acid
source                 1..347
                       mol_type = protein
                       organism = Hordeum vulgare
SEQUENCE: 80
MKTFLTFVLL AMAMSIVTTA RQLNPSHQEL QSPQQPFLKQ QSYLQQPYPQ QPYLPQQPFP  60
TPQQFFPYLP QQTFPPSQQP NPLQPQQPFP LQPQPPQQPF PQPQQPNPQQ PQQPFPRQPQ  120
QIVPQQPQQP FPQQPQQPFP QPQQPFSWQP QQPFLQPLQL XPLQAQQPFP LQPQLPFPQP  180
QQPIGQQPKQ PLLQQPQQTI PQQPQQPFPL QPQQPFPQQP QQPLPQQPQQ IISQQPQQPF  240
PLQPQQPFPQ PQPFPQEQPQ QAFPLQPQQP FPEESEQIIT QQPFPLQPQQ LFPQQPQQPL  300
PQPQQPFRQL PKYIIPQQPQ QPFLLQPHQP QQPYAQQDIW SDIALLG                347
```

```
SEQ ID NO: 81          moltype = AA  length = 305
FEATURE                Location/Qualifiers
source                 1..305
                       mol_type = protein
                       organism = Hordeum vulgare
SEQUENCE: 81
MKILIILTIL AMATTFATSE MQVNPSVQVQ PTQQQPYPES QQPFISQSQQ QFPQPQQPFP  60
QQPQQPFPQS QQQCLQQPQH QFPQPTQQFP QRPLLPFTHP FLTFPDQLLP QPPHQSFPQP  120
PQSYPQPPLQ PFPQPPQQKY PEQPQQPFPW QQPTIQLYLQ QQLNPCKEFL LQQCRPVSLL  180
SYIWSKIVQQ SSCRVMQQQC CLQLAQIPEQ YKCTAIDSIV HAIFMQQGQR QGVQIVQQQP  240
QPQQVGQCVL VQGQGVVQPQ QLAQMEAIRT LVLQSVPSMC NFNVPPNCST IKAPFVGVVT  300
GVGGQ                                                              305

SEQ ID NO: 82          moltype = AA  length = 255
FEATURE                Location/Qualifiers
source                 1..255
                       mol_type = protein
                       organism = Hordeum vulgare
SEQUENCE: 82
MQVNPSVQVQ PTQQQPYPES QQPFISQSQQ QFPQPQQPFP QRPLLPFTHP FLTFPDQLLP  60
QPPHQSFPQP PQSYPQPPLQ PFPQPPQQKY PEQPQQPFPW QQPTIQLYLQ QQLNPYKEFL  120
LQQCRPVSLL SYLWSKIVQQ SSCRVMLQQC CLQLAQIPEQ YKCTAIDSIV HAIFMQQGQR  180
QGVQIVQQQP QPQQVGQCVL VQGQGVVQPQ QLAQMEAIRT LVLQSVPSMC NFNVPPNCST  240
IKAPFVGVVT GVGGQ                                                   255

SEQ ID NO: 83          moltype = AA  length = 289
FEATURE                Location/Qualifiers
source                 1..289
                       mol_type = protein
                       organism = Hordeum vulgare
SEQUENCE: 83
ITTTTMQFNP SGLELERPQQ LFPQWQPLPQ QPPFLQQEPE QPYPQQQPLP QQQPFPQQPQ  60
LPHQHQFPQQ LPQQQFPQQM PLQPQQQFPQ QMPLQPQQQP QFPQQKPFGQ YQQPLTQQPY  120
PQQQPLAQQQ PSIEEQHQLN LCKEFLLQQC TLDEKVPLLQ SVISFLRPHI SQQNSCQLKR  180
QQCCQQLANI NEQSRCPAIQ TIVHAIVMQQ QVQQQVGHGF VQSQLQQLGQ GMPIQLQQQP  240
GQAFVLPQQQ AQFKVVGSLV IQTLPMLCNV HVPPYCSPFG SMATGSGGQ              289

SEQ ID NO: 84          moltype = AA  length = 173
FEATURE                Location/Qualifiers
source                 1..173
                       mol_type = protein
                       organism = Hordeum vulgare
SEQUENCE: 84
MKTMLILALI AFAATSAVAQ LDTTCSQGYG QCQQQPQQQM NTCAAFLQQC SRTPYVQSQM  60
WQASGCQLMR QQCCQPLAQI SEQARCQAVC SMAQVIMRQQ QGQSFTQPQQ QQSQSFGQPQ  120
QQVPVEVMRM VLQTLPSMCS VNIPQYCTTT PCSTITPTIY SIPMAATCAG GVC         173

SEQ ID NO: 85          moltype = AA  length = 13
FEATURE                Location/Qualifiers
source                 1..13
                       mol_type = protein
                       organism = Hordeum vulgare
SEQUENCE: 85
AQQLAAQLPA MCR                                                     13
```

The invention claimed is:

1. A method of producing a food or malt-based beverage ingredient, or a food or a malt-based beverage, from barley grain comprising 50 ppm or less hordeins *as measured by enzyme-linked immunosorbent assay* (*ELISA*), the method comprising:

(i) processing barley grain comprising 50 ppm or less hordeins *as measured by ELISA* to produce malt, wort, flour or wholemeal, and/or (ii) mixing barley grain comprising 50 ppm or less hordeins *as measured by ELISA*, or malt, wort, flour or wholemeal produced from said grain, with at least one other food or beverage ingredient, wherein:

a) the barley grain is homozygous for a genetic variation of the Hor2 locus where most or all of the B-hordein encoding genes in the Hor2 locus have been deleted relative to the Hor2 locus of wild-type barley grain, or wherein the malt, wort, flour or wholemeal produced from said grain comprises DNA which comprises the genetic variation of the Hor2 locus where most or all of the B-hordein encoding genes in the Hor2 locus have been deleted relative to the Hor2 locus of wild-type barley grain, b) the barley grain is homozygous for a genetic variation at the Hor3 locus of barley which results in the grain lacking [D-Hordein] *D-hordein*, or wherein the malt, wort, flour or wholemeal produced from said grain comprises DNA which comprises the genetic variation at the Hor3 locus of barley which results in the grain lacking D-hordein, and c) the barley grain is homozygous for a genetic variation at the Lys3 locus of barley which results in the grain lacking C-hordeins, or wherein the malt, wort, flour or wholemeal produced from said grain comprises DNA which comprises the genetic variation at the Lys3 locus which results in the grain lacking C-hordeins, thereby producing the food or malt-based beverage ingredient, or food or malt-based beverage.

2. The method of claim 1, wherein the grain, malt, wort, flour or wholemeal comprises 20 ppm or less hordeins *as measured by ELISA*.

3. The method of claim 1, wherein the average weight of the grain is at least 35 mg.

4. The method according to claim 1, wherein at least 80% of the grain do not pass through a 2.8 mm sieve.

5. The method according to claim 1, wherein the grain is from a plant which has a harvest index of about 40% to about 60%.

6. The method according to claim 1, wherein the grain has a length to thickness ratio of less than 5.

7. The method according to claim 1, wherein the flour or wholemeal produced from the grain comprises 10 ppm or less hordeins *as measured by ELISA*.

8. The method according to claim 1, wherein the grain, or malt, wort, flour or wholemeal produced from said grain lacks:

i) B-hordeins comprising a sequence of amino acids provided as SEQ ID NO:53, and ii) B-hordeins comprising a sequence of amino acids provided as SEQ ID NO:54.

9. The method according to claim 1, wherein the genetic variation at the Hor3 locus of barley which results in the grain lacking [D-Hordein] *D-hordein* is a null allele of the gene encoding D-hordein which comprises a stop codon, splice site mutation, frame-shift mutation, insertion, deletion or encoding a truncated D-hordein, or where most or all of the D-hordein encoding gene has been deleted.

10. The method according to claim 1, wherein the grain, malt, wort, flour or wholemeal comprises 1% or less, of the level of hordeins when compared to grain from a corresponding wild-type barley plant or malt, wort, flour or wholemeal produced in the same manner from grain from a corresponding wild-type barley plant.

11. The method according to claim 1, wherein the [coeliac] *celiac* toxicity of flour produced from the grain is less than about 5% of flour produced from grain of a corresponding wild-type barley plant.

12. The method according to claim 1, wherein at least 50% of the grain germinates within 3 days following imbibition.

13. The method according to claim 1, wherein the food ingredient or malt-based beverage ingredient is flour, starch, malt, or wort, or wherein the food is leavened or unleavened breads, pasta, noodles, breakfast cereals, snack foods, cakes, pastries or foods containing flour-based sauces.

14. The method according to claim 1, wherein the malt-based beverage is beer or whiskey.

15. The method according to claim 1, wherein following consumption of the food or drink at least one symptom of [coeliac's] *celiac* disease is not developed by a subject with said disease.

16. A barley grain comprising about 50 ppm or less hordeins *as measured by ELISA*, or a barley plant which produces grain comprising about 50 ppm or less hordeins *as measured by ELISA*, wherein:

a) the grain is homozygous for a genetic variation of the Hor2 locus where most or all of the B-hordein encoding genes in the Hor2 locus have been deleted relative to the Hor2 locus of wild-type barley grain, b) the grain is homozygous for a genetic variation at the Hor3 locus which results in the grain lacking D-hordeins, and c) the grain is homozygous for a genetic variation at the Lys3 locus of barley which results in the grain lacking C-hordeins.

17. A method of producing barley grain comprising about 50 ppm or less hordeins *as measured by ELISA*, the method comprising;

a) growing a barley plant of claim 16, and b) harvesting the grain of the barley plant.

18. The method of claim 1, wherein the barley grain, or malt, wort, flour or wholemeal produced from said grain, further has a level of less than 2% of a wild-type level of γ-hordeins comprising a sequence of amino acids provided as SEQ ID NO:57, wherein the level of less than 2% is relative to a wild-type barley grain, or malt, wort, flour or wholemeal produced from said grain, of the barley variety Bomi, Sloop, Baudin, Yagan, Hindmarsh, or Commander.

*19. The barley grain of claim 16.*

*20. The barley plant of claim 16.*

*21. A method of producing flour, wholemeal, starch, malt, wort or other product obtained from grain, the method comprising:*

*a) obtaining grain of claim 19, and*

*b) processing the grain. to produce the flour, wholemeal, starch, malt, wort or other product.*

*22. A food or malt-based beverage produced using the method of claim 1, wherein the food or malt-based beverage comprises DNA which has:*

*a) the genetic variation of the Hor2 locus where most or all of the B-hordein encoding genes in the Hor2 locus have been deleted relative to the Hor2 locus of wild-type barley grain,*

*b) the genetic variation at the Hor3 locus of barley which results in the grain lacking D-hordein, and*

*c) the genetic variation at the Lys3 locus which results in the grain lacking C-hordeins.*

*23. A method of avoiding or reducing the incidence or severity of celiac disease in a subject, the method comprising feeding to the subject the food or malt-based beverage of claim 22, wherein the reduction of the incidence or severity of celiac disease is relative to when the subject is fed the same amount of a corresponding food or malt-based beverage made from wild-type barley grain.*

*24. The barley plant of claim 20, wherein the average weight of the grain of the barley plant is 35 mg to 60 mg.*

*25. The barley plant of claim 20, wherein the average weight of the grain of the barley plant is 40 mg to 60 mg.*

*26. The barley plant of claim 20, wherein the average weight of the grain of the barley plant is 45 mg to 60 mg.*

*27. The barley plant of claim 20, wherein 80% to 98% of the grain does not pass through a 2.8mm sieve.*

*28. The barley plant of claim 20, wherein the grain of the barley plant comprises 0.05 ppm to 50 ppm hordeins as measured by ELISA.*

*29. The barley plant of claim 20, wherein the grain of the barley plant comprises 0.05 ppm to 20 ppm hordeins as measured by ELISA.*

*30. The barley plant of claim 20, wherein the grain of the barley plant comprises 0.05 ppm to 10 ppm hordeins as measured by ELISA.*

*31. The food or malt-based beverage of claim 22, wherein the food or malt-based beverage is beer.*

*32. The beer of claim 31, wherein the beer comprises one or more barley grain proteins and less than 0.9 ppm hordeins as measured by ELISA.*

*33. A food ingredient or malt-based beverage ingredient produced using the method of claim 1, wherein the food ingredient or malt-based beverage ingredient comprises DNA which has:*

*a) the genetic variation of the Hor2 locus where most or all of the B-hordein encoding genes in the Hor2 locus have been deleted relative to the Hor2 locus of wild-type barley grain,*

*b) the genetic variation at the Hor3 locus of barley which results in the grain lacking D-hordein, and*

*c) the genetic variation at the Lys3 locus which results in the grain lacking C-hordeins.*

*34. The food ingredient or malt-based beverage ingredient of claim 33, wherein the food or malt-based beverage ingredient is flour or wholemeal.*

*35. The flour or wholemeal of claim 34, wherein the flour or wholemeal comprises less than 20 ppm hordeins as measured by ELISA.*

*36. The food ingredient or malt-based beverage ingredient of claim 33, wherein the food or malt-based beverage ingredient is malt or wort.*

*37. The malt or wort of claim 36, wherein the malt or wort comprises less than 20 ppm hordeins as measured by ELISA.*

* * * * *